(12) United States Patent
Ghandehari et al.

(10) Patent No.: US 10,849,914 B2
(45) Date of Patent: *Dec. 1, 2020

(54) METHODS FOR PRODUCING CHEMOEMBOLIC AGENTS FOR THE DELIVERY OF ANTI-CANCER AGENTS

(71) Applicant: UNIVERSITY OF UTAH RESEARCH FOUNDATION, Salt Lake City, UT (US)

(72) Inventors: Hamid Ghandehari, Salt Lake City, UT (US); Joseph Cappello, Salt Lake City, UT (US); Azadeh Poursaid, Salt Lake City, UT (US); Mark Martin Jensen, Salt Lake City, UT (US)

(73) Assignee: UNIVERSITY OF UTAH RESEARCH FOUNDATION, Salt Lake City ( * ) Notice: Subject to any disclaimer, the term of this patent is extended or adjusted under 35 U.S.C. 154(b) by 5 days.

This patent is subject to a terminal disclaimer.

(21) Appl. No.: 16/006,015

(22) Filed: Jun. 12, 2018

(65) Prior Publication Data

US 2018/0353522 A1 Dec. 13, 2018

Related U.S. Application Data

(60) Provisional application No. 62/518,118, filed on Jun. 12, 2017.

(51) Int. Cl.
| | |
|---|---|
| *A61K 31/65* | (2006.01) |
| *A61K 9/06* | (2006.01) |
| *A61K 47/42* | (2017.01) |
| *A61K 31/44* | (2006.01) |
| *A61K 9/14* | (2006.01) |
| *A61K 9/00* | (2006.01) |

(52) U.S. Cl.
CPC ............ *A61K 31/65* (2013.01); *A61K 9/0024* (2013.01); *A61K 9/06* (2013.01); *A61K 9/146* (2013.01); *A61K 31/44* (2013.01); *A61K 47/42* (2013.01)

(58) Field of Classification Search
CPC ...... A61K 31/65; A61K 9/0024; A61K 9/146; A61K 31/44; A61K 47/42; A61K 9/06
See application file for complete search history.

(56) References Cited

U.S. PATENT DOCUMENTS

| | | | |
|---|---|---|---|
| 9,932,389 | B2 | 4/2018 | Cappello et al. |
| 2001/0018445 | A1 | 8/2001 | Huang et al. |
| 2003/0176355 | A1 | 9/2003 | Cappello et al. |
| 2005/0227910 | A1 | 10/2005 | Yang et al. |
| 2006/0009840 | A1 | 1/2006 | Hossainy |
| 2007/0054878 | A1 | 3/2007 | Venbrocks et al. |
| 2009/0246283 | A1 | 10/2009 | Kumar |
| 2010/0143304 | A1 | 6/2010 | Lowenstein |
| 2011/0129531 | A1 | 6/2011 | Collette et al. |
| 2011/0287517 | A1 | 11/2011 | Steward |
| 2012/0149032 | A1 | 6/2012 | Davis |
| 2012/0282300 | A1 | 11/2012 | Masters et al. |
| 2013/0011467 | A1 | 1/2013 | Zhang et al. |
| 2013/0022545 | A1 | 1/2013 | Lee et al. |
| 2013/0059772 | A1 | 3/2013 | Kumar |
| 2013/0195988 | A1 | 8/2013 | Duan et al. |
| 2014/0086976 | A1 | 3/2014 | Szalay |
| 2014/0194370 | A1 | 7/2014 | Cappello et al. |
| 2014/0206022 | A1 | 7/2014 | Nuti |
| 2014/0343011 | A1 | 11/2014 | Prestwich et al. |
| 2015/0152165 | A1 | 6/2015 | Ghandehari et al. |
| 2015/0209385 | A1 | 7/2015 | Prestwich et al. |

FOREIGN PATENT DOCUMENTS

| | | |
|---|---|---|
| WO | 2009158704 | 12/2009 |
| WO | 2011140024 | 11/2011 |
| WO | 2013181471 | 12/2013 |
| WO | 2014031693 | 2/2014 |

OTHER PUBLICATIONS

Anumolu et al., "Fabrication of highly uniform nanoparticles from recombinant silk-elastin-like protein polymers for therapeutic agent delivery," ACS Nano, 2011, 5:5374-5382.

Cappello et al., "In-situ self-assembling protein polymer gel systems for administration, delivery, and release of drugs," J. Controlled Release, 1998, 53:105-117.

Chang et al., "Nanochemical stimulus accelerates and directs the self-assembly of silk-elastinlike nanofibers," J. Am. Chem. Soc., 2011, 133:1745-1747.

Dinerman et al., "Swelling behavior of a genetically engineered silk-elastinlike protein polymer hydrogel," Biomaterials, 2002, 23:4203-4210.

Dubbini et al., "Injectable hyaluronic acid/PEG-p(HPMAm-lac)-based hydrogels dually cross-linked by thermal gelling and Michael addition," European Polymer J., 2015, 72:423-437.

Extended European Search Report for 13795353.6 dated Nov. 13, 2015.

Greish et al., "Silk-elastinlike protein polymers improve the efficacy of adenovirus thymidine kinase enzyme prodrug therapy of head and neck tumors," J. Gene Med., 2010, 12:572-579.

(Continued)

*Primary Examiner* — Robert S Cabral
(74) *Attorney, Agent, or Firm* — Ballard Spahr LLP

(57) ABSTRACT

Described herein are chemoembolic compositions and agents. The compositions include one or more anti-cancer agents and a silk-elastinlike protein polymer, wherein the compositions are liquids prior to administration to a subject but convert to hydrogels upon administration to the subject. Administration of the chemoembolic compositions to tumor and/or tumor vasculature in a subject having cancer can result in reduced or inhibited blood flow to the tumor as well as localized, sustained release of the anti-cancer agent in the vicinity of the tumor. Reduction in blood flow, in turn, results in a reduction of tumor volume and/or inhibition of tumor growth, while localized release of the anti-cancer agent results in reduced systemic effects and lower overall toxicity of treatment with the compositions.

22 Claims, 9 Drawing Sheets

Specification includes a Sequence Listing.

(56) References Cited

OTHER PUBLICATIONS

Gustafson et al., "Silk-elastinlike hydrogel improves the safety of adenovirus-mediated gene-directed enzyme-prodrug therapy," Mol. Pharm., 2010, 7:1050-1056.
Gustafson et al., "Silk-elastinlike protein polymers for adenoviral cancer gene therapy," PhD Dissertation, University of Utah, 2012, 266pp.
Gustafson et al., "Silk-elastinlike protein polymers for matrix-mediated cancer gene therapy," Adv. Drug Delivery Rev., 2010, 62:1590-1523.
Gustafson et al., "Silk-elastinlike recombinant polymers for gene therapy of head and neck cancer: from molecular definition to controlled gene expression," J. Controlled Release, 2009, 140:256-261.
Gustafson et al., "Synthesis and characterization of a matrix metalloproteinase responsive silk-elastinlike protein polymer," Biomacromolecules, 2013, 14:618-625.
Hu et al., "Biomaterials derived from silk-tropoelastin protein systems," Biomaterials, 2010, 31:8121-8131.
International Preliminary Report on Patentability for PCT/US2013/043487 dated Dec. 2, 2014.
International Search Report for PCT/US2013/043487 dated Jan. 7, 2014.
Llovet et al., "Systematic review of randomized trials for unresectable hepatocellular carcinoma: chemoembolization improves survival," Hepatology, 2003, 37:429-442.
Mecham et al., "Elastin degreation by matrix metalloproteinases," J. Biol. Chem., 1997, 272:18071-18076.
Megeed et al.. "Genetically engineered silk-elastinlike protein polymers for controlled drug delivery," Adv. Drug Delivery Rev., 2002 54:1075-1091.
Megeed et al., "In vitro and in vivo evaluation of recombinant silk-elastinike hydrogels for cancer gene therapy," J. Controlled Release, 2004, 94:433-445.
Netzel-Arnett et al., "Comparative sequence specificities of human 72- and 92-kDa gelatinases (type IV collagenases) and PUMP (matrilysin)," Biochemistry, 1993, 32:6427-6432.
Numata et al., "Silk-baed delivery systems of bioactive molecules," Adv. Drug Delivery Rev., 2010, 62:1497-1508.
Office Action for U.S. Appl. No. 14/150,652 dated Mar. 25, 2015.
Office Action for U.S. Appl. No. 14/150,652 dated Sep. 8, 2015.
Poursaid et al., "In situ gelling silk-elastinlike protein polymer for transarterial chemoembolization," Biomaterials, 2015, 57:142-152.
Poursaid et al., "Silk-elastinlike protein polymer liquid chemoembolic for localized release of doxorubicin and sorafenib," Molecular Pharmaceutics, 2016, 13:2730-2748.
Poursaid, A. "Design and Development of Silk-Elastinlike Protein Polymer Liquid Embolics for Treatment of Hepatocellular Carcinoma," Dissertation (partial), University of Utah, 2016, 43pp.
Price, "Effect of shear on physiochemical properties of matrix metalloproteinase responsive silk-elastinlike hydrogels," J. Controlled Release, 2014, 195:92-98.
Response to Office Action for U.S. Appl. No. 14/150,652 dated Aug. 25, 2015.
Skjot-Arkil et al., "Measurement of MMP-9 and -12 degraded elastin (ELM) provides unique information on lung tissue degradation," BMC Pulmonary Medicine, 2012, 12:1-12.
Varela et al., "Chemoembolization of hepatocellular carcinoma with drug eluting bead: efficacy and doxorubicin pharmacokinetics," J. Hepatology, 2007, 474-481.
Vartak et al., "Matrix metalloproteinases: underutilized targets for drug delivery," J. Drug Targeting, 2007, 15:1-20.
Vemula et al., "Self-assembled prodrugs: an enzymatically triggered drug-delivery platform," Biomaterials, 2009, 30:383-393.
Wirostko et al., "Ophthalmic uses of a thiol-modified hyaluronan-baed hydrogel," Adv. Wound Care, 2014, 3:708-716.
Written Opinion for PCT/US2013/043487 dated Jan. 7, 2014.

```
SEQUENCE LISTING

<160> NUMBER OF SEQ ID NOS: 34

<210> SEQ ID NO 1
<211> LENGTH: 936
<212> TYPE: PRT
<213> ORGANISM: Artificial sequence
<220> FEATURE:
<223> OTHER INFORMATION: Synthetic construct

<400> SEQUENCE: 1

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Gly Ala Gly Ala Gly Ser Gly Ala
        35                  40                  45

Gly Ala Gly Ser Val Pro Gly Val Gly Val Pro Gly Val Gly Val Pro
    50                  55                  60

Gly Val Gly Val Pro Gly Val Gly Val Pro Gly Val Gly Val Pro Gly
65                  70                  75                  80

Val Gly Val Pro Gly Val Gly Val Pro Gly Val Gly Gly Ala Gly Ala
                85                  90                  95

Gly Ser Gly Ala Gly Ala Gly Ser Val Pro Gly Val Gly Val Pro Gly
            100                 105                 110

Val Gly Val Pro Gly Val Gly Val Pro Gly Val Gly Val Pro Gly Val
        115                 120                 125

Gly Val Pro Gly Val Gly Val Pro Gly Val Gly Val Pro Gly Val Gly
    130                 135                 140

Gly Ala Gly Ala Gly Ser Gly Ala Gly Ala Gly Ser Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Gly Ala Gly Ala Gly Ser Gly Ala Gly Ala Gly Ser
        195                 200                 205

Val Pro Gly Val Gly Val Pro Gly Val Gly Val Pro Gly Val Gly Val
    210                 215                 220
```

```
Pro Gly Val Gly Val Pro Gly Val Gly Val Pro Gly Val Gly Val Pro
225                 230                 235                 240

Gly Val Gly Val Pro Gly Val Gly Gly Ala Gly Ala Gly Ser Gly Ala
                245                 250                 255

Gly Ala Gly Ser Val Pro Gly Val Gly Val Pro Gly Val Gly Val Pro
            260                 265                 270

Gly Val Gly Val Pro Gly Val Gly Val Pro Gly Val Gly Val Pro Gly
        275                 280                 285

Val Gly Val Pro Gly Val Gly Val Pro Gly Val Gly Gly Ala Gly Ala
    290                 295                 300

Gly Ser Gly Ala Gly Ala Gly Ser Val Pro Gly Val Gly Val Pro Gly
305                 310                 315                 320

Val Gly Val Pro Gly Val Gly Val Pro Gly Val Gly Val Pro Gly Val
                325                 330                 335

Gly Val Pro Gly Val Gly Val Pro Gly Val Gly Val Pro Gly Val Gly
            340                 345                 350

Gly Ala Gly Ala Gly Ser Gly Ala Gly Ala Gly Ser Val Pro Gly Val
        355                 360                 365

Gly Val Pro Gly Val Gly Val Pro Gly Val Gly Val Pro Gly Val Gly
    370                 375                 380

Val Pro Gly Val Gly Val Pro Gly Val Gly Val Pro Gly Val Gly Val
385                 390                 395                 400

Pro Gly Val Gly Gly Ala Gly Ala Gly Ser Gly Ala Gly Ala Gly Ser
                405                 410                 415

Val Pro Gly Val Gly Val Pro Gly Val Gly Val Pro Gly Val Gly Val
            420                 425                 430

Pro Gly Val Gly Val Pro Gly Val Gly Val Pro Gly Val Gly Val Pro
        435                 440                 445

Gly Val Gly Val Pro Gly Val Gly Gly Ala Gly Ala Gly Ser Gly Ala
    450                 455                 460

Gly Ala Gly Ser Val Pro Gly Val Gly Val Pro Gly Val Gly Val Pro
465                 470                 475                 480

Gly Val Gly Val Pro Gly Val Gly Val Pro Gly Val Gly Val Pro Gly
                485                 490                 495

Val Gly Val Pro Gly Val Gly Val Pro Gly Val Gly Gly Ala Gly Ala
            500                 505                 510

Gly Ser Gly Ala Gly Ala Gly Ser Val Pro Gly Val Gly Val Pro Gly
        515                 520                 525

Val Gly Val Pro Gly Val Gly Val Pro Gly Val Gly Val Pro Gly Val
    530                 535                 540

Gly Val Pro Gly Val Gly Val Pro Gly Val Gly Val Pro Gly Val Gly
545                 550                 555                 560

Gly Ala Gly Ala Gly Ser Gly Ala Gly Ala Gly Ser Val Pro Gly Val
                565                 570                 575

Gly Val Pro Gly Val Gly Val Pro Gly Val Gly Val Pro Gly Val Gly
            580                 585                 590

Val Pro Gly Val Gly Val Pro Gly Val Gly Val Pro Gly Val Gly Val
        595                 600                 605

Pro Gly Val Gly Gly Ala Gly Ala Gly Ser Gly Ala Gly Ala Gly Ser
    610                 615                 620

Val Pro Gly Val Gly Val Pro Gly Val Gly Val Pro Gly Val Gly Val
625                 630                 635                 640
```

-continued

Pro Gly Val Gly Val Pro Gly Val Gly Val Pro Gly Val Gly Val Pro
                     645                 650                 655

Gly Val Gly Val Pro Gly Val Gly Ala Gly Ala Gly Ser Gly Ala
            660                 665                 670

Gly Ala Gly Ser Val Pro Gly Val Gly Val Pro Gly Val Gly Val Pro
            675                 680                 685

Gly Val Gly Val Pro Gly Val Gly Val Pro Gly Val Gly Val Pro Gly
        690                 695                 700

Val Gly Val Pro Gly Val Gly Val Pro Gly Val Gly Ala Gly Ala
705                 710                 715                 720

Gly Ser Gly Ala Gly Ala Gly Ser Val Pro Gly Val Gly Val Pro Gly
            725                 730                 735

Val Gly Val Pro Gly Val Gly Val Pro Gly Val Gly Val Pro Gly Val
            740                 745                 750

Gly Val Pro Gly Val Gly Val Pro Gly Val Gly Val Pro Gly Val Gly
            755                 760                 765

Gly Ala Gly Ala Gly Ser Gly Ala Gly Ala Gly Ser Val Pro Gly Val
        770                 775                 780

Gly Val Pro Gly Val Gly Val Pro Gly Val Gly Val Pro Gly Val Gly
785                 790                 795                 800

Val Pro Gly Val Gly Val Pro Gly Val Gly Val Pro Gly Val Gly Val
            805                 810                 815

Pro Gly Val Gly Gly Ala Gly Ala Gly Ser Gly Ala Gly Ala Gly Ser
            820                 825                 830

Val Pro Gly Val Gly Val Pro Gly Val Gly Val Pro Gly Val Gly Val
            835                 840                 845

Pro Gly Val Gly Val Pro Gly Val Gly Val Pro Gly Val Gly Val Pro
        850                 855                 860

Gly Val Gly Val Pro Gly Val Gly Ala Gly Ala Gly Ser Gly Ala
865                 870                 875                 880

Gly Ala Gly Ser Val Pro Gly Val Gly Val Pro Gly Val Gly Val Pro
            885                 890                 895

Gly Val Gly Val Pro Gly Val Gly Val Pro Gly Val Gly Val Pro Gly
            900                 905                 910

Val Gly Val Pro Gly Val Gly Val Pro Gly Val Gly Gly Ala Gly Ala
        915                 920                 925

Gly Ser Gly Ala Gly Ala Gly Ser
    930                 935

<210> SEQ ID NO 2
<211> LENGTH: 962
<212> TYPE: PRT
<213> ORGANISM: Artificial sequence
<220> FEATURE:
<223> OTHER INFORMATION: Synthetic construct

<400> SEQUENCE: 2

Gly Val Gly Val Pro Gly Val Gly Val Pro Gly Val Gly Val Pro Gly
1               5                   10                  15

Val Gly Val Pro Gly Ala Gly Ala Gly Ser Gly Ala Gly Ala Gly Ser
            20                  25                  30

Gly Ala Gly Ala Gly Ser Gly Ala Gly Ala Gly Ser Gly Ala Gly Ala
        35                  40                  45

Gly Ser Gly Ala Gly Ala Gly Ser Gly Ala Gly Ala Gly Ser Gly Ala
    50                  55                  60

```
Gly Ala Gly Ser Gly Ala Gly Ala Gly Ser Gly Val Gly Val Pro Gly
 65                  70                  75                  80

Val Gly Val Pro Gly Val Gly Val Pro Gly Val Gly Val Pro Gly Ala
                 85                  90                  95

Gly Ala Gly Ser Gly Ala Gly Ala Gly Ser Gly Ala Gly Ala Gly Ser
            100                 105                 110

Gly Ala Gly Ala Gly Ser Gly Ala Gly Ala Gly Ser Gly Ala Gly Ala
        115                 120                 125

Gly Ser Gly Ala Gly Ala Gly Ser Gly Ala Gly Ala Gly Ser Gly Ala
    130                 135                 140

Gly Ala Gly Ser Gly Val Gly Val Pro Gly Val Gly Val Pro Gly Val
145                 150                 155                 160

Gly Val Pro Gly Val Gly Val Pro Gly Ala Gly Ala Gly Ser Gly Ala
            165                 170                 175

Gly Ala Gly Ser Gly Ala Gly Ala Gly Ser Gly Ala Gly Ala Gly Ser
        180                 185                 190

Gly Ala Gly Ala Gly Ser Gly Ala Gly Ala Gly Ser Gly Ala Gly Ala
    195                 200                 205

Gly Ser Gly Ala Gly Ala Gly Ser Gly Ala Gly Ala Gly Ser Gly Val
    210                 215                 220

Gly Val Pro Gly Val Gly Val Pro Gly Val Gly Val Pro Gly Val Gly
225                 230                 235                 240

Val Pro Gly Ala Gly Ala Gly Ser Gly Ala Gly Ala Gly Ser Gly Ala
            245                 250                 255

Gly Ala Gly Ser Gly Ala Gly Ala Gly Ser Gly Ala Gly Ala Gly Ser
        260                 265                 270

Gly Ala Gly Ala Gly Ser Gly Ala Gly Ala Gly Ser Gly Ala Gly Ala
    275                 280                 285

Gly Ser Gly Ala Gly Ala Gly Ser Val Gly Val Pro Gly Val Gly
    290                 295                 300

Val Pro Gly Val Gly Val Pro Gly Val Gly Val Pro Gly Ala Gly Ala
305                 310                 315                 320

Gly Ser Gly Ala Gly Ala Gly Ser Gly Ala Gly Ala Gly Ser Gly Ala
            325                 330                 335

Gly Ala Gly Ser Gly Ala Gly Ala Gly Ser Gly Ala Gly Ala Gly Ser
        340                 345                 350

Gly Ala Gly Ala Gly Ser Gly Ala Gly Ala Gly Ser Gly Ala Gly Ala
    355                 360                 365

Gly Ser Gly Val Gly Val Pro Gly Val Gly Val Pro Gly Val Gly Val
    370                 375                 380

Pro Gly Val Gly Val Pro Gly Ala Gly Ala Gly Ser Gly Ala Gly Ala
385                 390                 395                 400

Gly Ser Gly Ala Gly Ala Gly Ser Gly Ala Gly Ala Gly Ser Gly Ala
            405                 410                 415

Gly Ala Gly Ser Gly Ala Gly Ala Gly Ser Gly Ala Gly Ala Gly Ser
        420                 425                 430

Gly Ala Gly Ala Gly Ser Gly Ala Gly Ala Gly Ser Gly Val Gly Val
    435                 440                 445

Pro Gly Val Gly Val Pro Gly Val Gly Val Pro Gly Val Gly Val Pro
    450                 455                 460

Gly Ala Gly Ala Gly Ser Gly Ala Gly Ala Gly Ser Gly Ala Gly Ala
465                 470                 475                 480

Gly Ser Gly Ala Gly Ala Gly Ser Gly Ala Gly Ala Gly Ser Gly Ala
```

```
                485                 490                 495
Gly Ala Gly Ser Gly Ala Gly Ala Gly Ser Gly Ala Gly Ala Gly Ser
                500                 505                 510
Gly Ala Gly Ala Gly Ser Gly Val Gly Val Pro Gly Val Gly Val Pro
                515                 520                 525
Gly Val Gly Val Pro Gly Val Gly Val Pro Gly Ala Gly Ala Gly Ser
                530                 535                 540
Gly Ala Gly Ala Gly Ser Gly Ala Gly Ala Gly Ser Gly Ala Gly Ala
545                 550                 555                 560
Gly Ser Gly Ala Gly Ala Gly Ser Gly Ala Gly Ala Gly Ser Gly Ala
                565                 570                 575
Gly Ala Gly Ser Gly Ala Gly Ala Gly Ser Gly Ala Gly Ala Gly Ser
                580                 585                 590
Gly Val Gly Val Pro Gly Val Gly Val Pro Gly Val Gly Val Pro Gly
                595                 600                 605
Val Gly Val Pro Gly Ala Gly Ala Gly Ser Gly Ala Gly Ala Gly Ser
                610                 615                 620
Gly Ala Gly Ala Gly Ser Gly Ala Gly Ala Gly Ser Gly Ala Gly Ala
625                 630                 635                 640
Gly Ser Gly Ala Gly Ala Gly Ser Gly Ala Gly Ala Gly Ser Gly Ala
                645                 650                 655
Gly Ala Gly Ser Gly Ala Gly Ala Gly Ser Gly Val Gly Val Pro Gly
                660                 665                 670
Val Gly Val Pro Gly Val Gly Val Pro Gly Val Gly Val Pro Gly Ala
                675                 680                 685
Gly Ala Gly Ser Gly Ala Gly Ala Gly Ser Gly Ala Gly Ala Gly Ser
                690                 695                 700
Gly Ala Gly Ala Gly Ser Gly Ala Gly Ala Gly Ser Gly Ala Gly Ala
705                 710                 715                 720
Gly Ser Gly Ala Gly Ala Gly Ser Gly Ala Gly Ala Gly Ser Gly Ala
                725                 730                 735
Gly Ala Gly Ser Gly Val Gly Val Pro Gly Val Gly Val Pro Gly Val
                740                 745                 750
Gly Val Pro Gly Val Gly Val Pro Gly Ala Gly Ala Gly Ser Gly Ala
                755                 760                 765
Gly Ala Gly Ser Gly Ala Gly Ala Gly Ser Gly Ala Gly Ala Gly Ser
                770                 775                 780
Gly Ala Gly Ala Gly Ser Gly Ala Gly Ala Gly Ser Gly Ala Gly Ala
785                 790                 795                 800
Gly Ser Gly Ala Gly Ala Gly Ser Gly Ala Gly Ala Gly Ser Gly Val
                805                 810                 815
Gly Val Pro Gly Val Gly Val Pro Gly Val Gly Val Pro Gly Val Gly
                820                 825                 830
Val Pro Gly Ala Gly Ala Gly Ser Gly Ala Gly Ala Gly Ser Gly Ala
                835                 840                 845
Gly Ala Gly Ser Gly Ala Gly Ala Gly Ser Gly Ala Gly Ala Gly Ser
                850                 855                 860
Gly Ala Gly Ala Gly Ser Gly Ala Gly Ala Gly Ser Gly Ala Gly Ala
865                 870                 875                 880
Gly Ser Gly Ala Gly Ala Gly Ser Gly Val Gly Val Pro Gly Val Gly
                885                 890                 895
Val Pro Gly Val Gly Val Pro Gly Val Gly Val Pro Gly Ala Gly Ala
                900                 905                 910
```

```
Gly Ser Gly Ala Gly Ala Gly Ser Gly Ala Gly Ala Gly Ser Gly Ala
        915                 920                 925

Gly Ala Gly Ser Gly Ala Gly Ala Gly Ser Gly Ala Gly Ala Gly Ser
    930                 935                 940

Gly Ala Gly Ala Gly Ser Gly Ala Gly Ala Gly Ser Gly Ala Gly Ala
945                 950                 955                 960

Gly Ser

<210> SEQ ID NO 3
<211> LENGTH: 768
<212> TYPE: PRT
<213> ORGANISM: Artificial sequence
<220> FEATURE:
<223> OTHER INFORMATION: Synthetic construct

<400> SEQUENCE: 3

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Val Pro Gly Val Gly Val Pro Gly Val Gly Val Pro Gly Val Gly Val
65              70                  75                  80

Pro Gly Val Gly Val Pro Gly Val Gly Val Pro Gly Val Gly Val Pro
            85                  90                  95

Gly Val Gly Val Pro Gly Val Gly Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Gly Ala Gly Ala Gly Ser Gly Ala
                165                 170                 175

Gly Ala Gly Ser Gly Ala Gly Ala Gly Ser Gly Ala Gly Ala Gly Ser
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Gly Ala Gly Ala Gly Ser Gly Ala
225                 230                 235                 240

Gly Ala Gly Ser Gly Ala Gly Ala Gly Ser Gly Ala Gly Ala Gly Ser
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Gly Ala Gly Ala Gly Ser Gly Ala
    290                 295                 300
```

-continued

```
Gly Ala Gly Ser Gly Ala Gly Ala Gly Ser Gly Ala Gly Ala Gly Ser
305                 310                 315                 320

Val Pro Gly Val Gly Val Pro Gly Val Gly Val Pro Gly Val Gly Val
            325                 330                 335

Pro Gly Val Gly Val Pro Gly Val Gly Val Pro Gly Val Gly Val Pro
            340                 345                 350

Gly Val Gly Val Pro Gly Val Gly Ala Gly Ala Gly Ser Gly Ala
        355                 360                 365

Gly Ala Gly Ser Gly Ala Gly Ala Gly Ser Gly Ala Gly Ala Gly Ser
        370                 375                 380

Val Pro Gly Val Gly Val Pro Gly Val Gly Val Pro Gly Val Gly Val
385                 390                 395                 400

Pro Gly Val Gly Val Pro Gly Val Gly Val Pro Gly Val Gly Val Pro
            405                 410                 415

Gly Val Gly Val Pro Gly Val Gly Ala Gly Ala Gly Ser Gly Ala
            420                 425                 430

Gly Ala Gly Ser Gly Ala Gly Ala Gly Ser Gly Ala Gly Ala Gly Ser
        435                 440                 445

Val Pro Gly Val Gly Val Pro Gly Val Gly Val Pro Gly Val Gly Val
450                 455                 460

Pro Gly Val Gly Val Pro Gly Val Gly Val Pro Gly Val Gly Val Pro
465                 470                 475                 480

Gly Val Gly Val Pro Gly Val Gly Ala Gly Ala Gly Ser Gly Ala
            485                 490                 495

Gly Ala Gly Ser Gly Ala Gly Ala Gly Ser Gly Ala Gly Ala Gly Ser
        500                 505                 510

Val Pro Gly Val Gly Val Pro Gly Val Gly Val Pro Gly Val Gly Val
        515                 520                 525

Pro Gly Val Gly Val Pro Gly Val Gly Val Pro Gly Val Gly Val Pro
530                 535                 540

Gly Val Gly Val Pro Gly Val Gly Ala Gly Ala Gly Ser Gly Ala
545                 550                 555                 560

Gly Ala Gly Ser Gly Ala Gly Ala Gly Ser Gly Ala Gly Ala Gly Ser
            565                 570                 575

Val Pro Gly Val Gly Val Pro Gly Val Gly Val Pro Gly Val Gly Val
            580                 585                 590

Pro Gly Val Gly Val Pro Gly Val Gly Val Pro Gly Val Gly Val Pro
        595                 600                 605

Gly Val Gly Val Pro Gly Val Gly Ala Gly Ala Gly Ser Gly Ala
        610                 615                 620

Gly Ala Gly Ser Gly Ala Gly Ala Gly Ser Gly Ala Gly Ala Gly Ser
625                 630                 635                 640

Val Pro Gly Val Gly Val Pro Gly Val Gly Val Pro Gly Val Gly Val
            645                 650                 655

Pro Gly Val Gly Val Pro Gly Val Gly Val Pro Gly Val Gly Val Pro
            660                 665                 670

Gly Val Gly Val Pro Gly Val Gly Ala Gly Ala Gly Ser Gly Ala
            675                 680                 685

Gly Ala Gly Ser Gly Ala Gly Ala Gly Ser Gly Ala Gly Ala Gly Ser
        690                 695                 700

Val Pro Gly Val Gly Val Pro Gly Val Gly Val Pro Gly Val Gly Val
        705                 710                 715                 720

Pro Gly Val Gly Val Pro Gly Val Gly Val Pro Gly Val Gly Val Pro
```

```
                    725                 730                 735
Gly Val Gly Val Pro Gly Val Gly Ala Gly Ala Gly Ser Gly Ala
                740                 745                 750
Gly Ala Gly Ser Gly Ala Gly Ala Gly Ser Gly Ala Gly Ala Gly Ser
                755                 760                 765

<210> SEQ ID NO 4
<211> LENGTH: 912
<212> TYPE: PRT
<213> ORGANISM: Artificial sequence
<220> FEATURE:
<223> OTHER INFORMATION: Synthetic construct

<400> SEQUENCE: 4

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
                20                  25                  30
Gly Val Gly Val Pro Gly Val Gly Ala Gly Ala Gly Ser Gly Ala
            35                  40                  45
Gly Ala Gly Ser Gly Ala Gly Ala Gly Ser Gly Ala Gly Ala Gly Ser
        50                  55                  60
Gly Ala Gly Ala Gly Ser Gly Ala Gly Ala Gly Ser Val Pro Gly Val
65                  70                  75                  80
Gly Val Pro Gly Val Gly Val Pro Gly Val Gly Val Pro Gly Val Gly
                85                  90                  95
Val Pro Gly Val Gly Val Pro Gly Val Gly Val Pro Gly Val Gly Val
                100                 105                 110
Pro Gly Val Gly Gly Ala Gly Ala Gly Ser Gly Ala Gly Ala Gly Ser
            115                 120                 125
Gly Ala Gly Ala Gly Ser Gly Ala Gly Ala Gly Ser Gly Ala Gly Ala
        130                 135                 140
Gly Ser Gly Ala Gly Ala Gly Ser Val Pro Gly Val Gly Val Pro Gly
145                 150                 155                 160
Val Gly Val Pro Gly Val Gly Val Pro Gly Val Gly Val Pro Gly Val
                165                 170                 175
Gly Val Pro Gly Val Gly Val Pro Gly Val Gly Val Pro Gly Val Gly
                180                 185                 190
Gly Ala Gly Ala Gly Ser Gly Ala Gly Ala Gly Ser Gly Ala Gly Ala
            195                 200                 205
Gly Ser Gly Ala Gly Ala Gly Ser Gly Ala Gly Ala Gly Ser Gly Ala
        210                 215                 220
Gly Ala Gly Ser Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Gly Ala Gly Ala
                260                 265                 270
Gly Ser Gly Ala Gly Ala Gly Ser Gly Ala Gly Ala Gly Ser Gly Ala
            275                 280                 285
Gly Ala Gly Ser Gly Ala Gly Ala Gly Ser Gly Ala Gly Ala Gly Ser
        290                 295                 300
Val Pro Gly Val Gly Val Pro Gly Val Gly Val Pro Gly Val Gly Val
305                 310                 315                 320
Pro Gly Val Gly Val Pro Gly Val Gly Val Pro Gly Val Gly Val Pro
```

```
                 325                 330                 335
Gly Val Gly Val Pro Gly Val Gly Ala Gly Ala Gly Ser Gly Ala
             340                 345                 350
Gly Ala Gly Ser Gly Ala Gly Ala Gly Ser Gly Ala Gly Ala Gly Ser
             355                 360                 365
Gly Ala Gly Ala Gly Ser Gly Ala Gly Ala Gly Ser Val Pro Gly Val
             370                 375                 380
Gly Val Pro Gly Val Gly Val Pro Gly Val Gly Val Pro Gly Val Gly
 385                 390                 395                 400
Val Pro Gly Val Gly Val Pro Gly Val Gly Val Pro Gly Val Gly Val
             405                 410                 415
Pro Gly Val Gly Gly Ala Gly Ala Gly Ser Gly Ala Gly Ala Gly Ser
             420                 425                 430
Gly Ala Gly Ala Gly Ser Gly Ala Gly Ala Gly Ser Gly Ala Gly Ala
             435                 440                 445
Gly Ser Gly Ala Gly Ala Gly Ser Val Pro Gly Val Gly Val Pro Gly
             450                 455                 460
Val Gly Val Pro Gly Val Gly Val Pro Gly Val Gly Val Pro Gly Val
 465                 470                 475                 480
Gly Val Pro Gly Val Gly Val Pro Gly Val Gly Val Pro Gly Val Gly
             485                 490                 495
Gly Ala Gly Ala Gly Ser Gly Ala Gly Ala Gly Ser Gly Ala Gly Ala
             500                 505                 510
Gly Ser Gly Ala Gly Ala Gly Ser Gly Ala Gly Ala Gly Ser Gly Ala
             515                 520                 525
Gly Ala Gly Ser Val Pro Gly Val Gly Val Pro Gly Val Gly Val Pro
             530                 535                 540
Gly Val Gly Val Pro Gly Val Gly Val Pro Gly Val Gly Val Pro Gly
 545                 550                 555                 560
Val Gly Val Pro Gly Val Gly Val Pro Gly Val Gly Gly Ala Gly Ala
                         565                 570                 575
Gly Ser Gly Ala Gly Ala Gly Ser Gly Ala Gly Ala Gly Ser Gly Ala
             580                 585                 590
Gly Ala Gly Ser Gly Ala Gly Ala Gly Ser Gly Ala Gly Ala Gly Ser
             595                 600                 605
Val Pro Gly Val Gly Val Pro Gly Val Gly Val Pro Gly Val Gly Val
             610                 615                 620
Pro Gly Val Gly Val Pro Gly Val Gly Val Pro Gly Val Gly Val Pro
 625                 630                 635                 640
Gly Val Gly Val Pro Gly Val Gly Gly Ala Gly Ala Gly Ser Gly Ala
                         645                 650                 655
Gly Ala Gly Ser Gly Ala Gly Ala Gly Ser Gly Ala Gly Ala Gly Ser
             660                 665                 670
Gly Ala Gly Ala Gly Ser Gly Ala Gly Ala Gly Ser Val Pro Gly Val
             675                 680                 685
Gly Val Pro Gly Val Gly Val Pro Gly Val Gly Val Pro Gly Val Gly
             690                 695                 700
Val Pro Gly Val Gly Val Pro Gly Val Gly Val Pro Gly Val Gly Val
 705                 710                 715                 720
Pro Gly Val Gly Gly Ala Gly Ala Gly Ser Gly Ala Gly Ala Gly Ser
                         725                 730                 735
Gly Ala Gly Ala Gly Ser Gly Ala Gly Ala Gly Ser Gly Ala Gly Ala
             740                 745                 750
```

```
Gly Ser Gly Ala Gly Ala Gly Ser Val Pro Gly Val Gly Val Pro Gly
        755                 760                 765

Val Gly Val Pro Gly Val Gly Val Pro Gly Val Gly Val Pro Gly Val
    770                 775                 780

Gly Val Pro Gly Val Gly Val Pro Gly Val Gly Val Pro Gly Val Gly
785                 790                 795                 800

Gly Ala Gly Ala Gly Ser Gly Ala Gly Ala Gly Ser Gly Ala Gly Ala
            805                 810                 815

Gly Ser Gly Ala Gly Ala Gly Ser Gly Ala Gly Ala Gly Ser Gly Ala
        820                 825                 830

Gly Ala Gly Ser Val Pro Gly Val Gly Val Pro Gly Val Gly Val Pro
            835                 840                 845

Gly Val Gly Val Pro Gly Val Gly Val Pro Gly Val Gly Val Pro Gly
        850                 855                 860

Val Gly Val Pro Gly Val Gly Val Pro Gly Val Gly Val Gly Ala Gly Ala
865                 870                 875                 880

Gly Ser Gly Ala Gly Ala Gly Ser Gly Ala Gly Ala Gly Ser Gly Ala
            885                 890                 895

Gly Ala Gly Ser Gly Ala Gly Ala Gly Ser Gly Ala Gly Ala Gly Ser
        900                 905                 910

<210> SEQ ID NO 5
<211> LENGTH: 968
<212> TYPE: PRT
<213> ORGANISM: Artificial sequence
<220> FEATURE:
<223> OTHER INFORMATION: Synthetic construct

<400> SEQUENCE: 5

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser Val Pro Gly Val Gly Val Pro Gly
            85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Gly Ala Gly Ala Gly Ser Gly Ala Gly Ala Gly Ser Gly Ala Gly Ala
    130                 135                 140

Gly Ser Gly Ala Gly Ala Gly Ser Gly Ala Gly Ala Gly Ser Gly Ala
145                 150                 155                 160

Gly Ala Gly Ser Gly Ala Gly Ala Gly Ser Gly Ala Gly Ala Gly Ser
            165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205
```

```
Gly Val Gly Val Pro Gly Val Gly Ala Gly Ala Gly Ser Gly Ala
    210             215             220
Gly Ala Gly Ser Gly Ala Gly Ala Gly Ser Gly Ala Gly Ala Gly Ser
225             230             235             240
Gly Ala Gly Ala Gly Ser Gly Ala Gly Ala Gly Ser Gly Ala Gly Ala
            245             250             255
Gly Ser Gly Ala Gly Ala Gly Ser Val Pro Gly Val Gly Val Pro Gly
        260             265             270
Val Gly Val Pro Gly Val Gly Val Pro Gly Val Gly Val Pro Gly Val
    275             280             285
Gly Val Pro Gly Val Gly Val Pro Gly Val Gly Val Pro Gly Val Gly
    290             295             300
Gly Ala Gly Ala Gly Ser Gly Ala Gly Ala Gly Ser Gly Ala Gly Ala
305             310             315             320
Gly Ser Gly Ala Gly Ala Gly Ser Gly Ala Gly Ala Gly Ser Gly Ala
            325             330             335
Gly Ala Gly Ser Gly Ala Gly Ala Gly Ser Gly Ala Gly Ala Gly Ser
        340             345             350
Val Pro Gly Val Gly Val Pro Gly Val Gly Val Pro Gly Val Gly Val
    355             360             365
Pro Gly Val Gly Val Pro Gly Val Gly Val Pro Gly Val Gly Val Pro
    370             375             380
Gly Val Gly Val Pro Gly Val Gly Ala Gly Ala Gly Ser Gly Ala
385             390             395             400
Gly Ala Gly Ser Gly Ala Gly Ala Gly Ser Gly Ala Gly Ala Gly Ser
            405             410             415
Gly Ala Gly Ala Gly Ser Gly Ala Gly Ala Gly Ser Gly Ala Gly Ala
        420             425             430
Gly Ser Gly Ala Gly Ala Gly Ser Val Pro Gly Val Gly Val Pro Gly
        435             440             445
Val Gly Val Pro Gly Val Gly Val Pro Gly Val Gly Val Pro Gly Val
    450             455             460
Gly Val Pro Gly Val Gly Val Pro Gly Val Gly Val Pro Gly Val Gly
465             470             475             480
Gly Ala Gly Ala Gly Ser Gly Ala Gly Ala Gly Ser Gly Ala Gly Ala
            485             490             495
Gly Ser Gly Ala Gly Ala Gly Ser Gly Ala Gly Ala Gly Ser Gly Ala
        500             505             510
Gly Ala Gly Ser Gly Ala Gly Ala Gly Ser Gly Ala Gly Ala Gly Ser
    515             520             525
Val Pro Gly Val Gly Val Pro Gly Val Gly Val Pro Gly Val Gly Val
    530             535             540
Pro Gly Val Gly Val Pro Gly Val Gly Val Pro Gly Val Gly Val Pro
545             550             555             560
Gly Val Gly Val Pro Gly Val Gly Ala Gly Ala Gly Ser Gly Ala
            565             570             575
Gly Ala Gly Ser Gly Ala Gly Ala Gly Ser Gly Ala Gly Ala Gly Ser
        580             585             590
Gly Ala Gly Ala Gly Ser Gly Ala Gly Ala Gly Ser Gly Ala Gly Ala
        595             600             605
Gly Ser Gly Ala Gly Ala Gly Ser Val Pro Gly Val Gly Val Pro Gly
    610             615             620
```

```
Val Gly Val Pro Gly Val Gly Val Pro Gly Val Gly Val Pro Gly Val
625                 630                 635                 640

Gly Val Pro Gly Val Gly Val Pro Gly Val Gly Val Pro Gly Val Gly
                645                 650                 655

Gly Ala Gly Ala Gly Ser Gly Ala Gly Ala Gly Ser Gly Ala Gly Ala
            660                 665                 670

Gly Ser Gly Ala Gly Ala Gly Ser Gly Ala Gly Ala Gly Ser Gly Ala
        675                 680                 685

Gly Ala Gly Ser Gly Ala Gly Ala Gly Ser Gly Ala Gly Ala Gly Ser
    690                 695                 700

Val Pro Gly Val Gly Val Pro Gly Val Gly Val Pro Gly Val Gly Val
705                 710                 715                 720

Pro Gly Val Gly Val Pro Gly Val Gly Val Pro Gly Val Gly Val Pro
                725                 730                 735

Gly Val Gly Val Pro Gly Val Gly Ala Gly Ala Gly Ser Gly Ala
            740                 745                 750

Gly Ala Gly Ser Gly Ala Gly Ala Gly Ser Gly Ala Gly Ala Gly Ser
        755                 760                 765

Gly Ala Gly Ala Gly Ser Gly Ala Gly Ala Gly Ser Gly Ala Gly Ala
    770                 775                 780

Gly Ser Gly Ala Gly Ala Gly Ser Val Pro Gly Val Gly Val Pro Gly
785                 790                 795                 800

Val Gly Val Pro Gly Val Gly Val Pro Gly Val Gly Val Pro Gly Val
                805                 810                 815

Gly Val Pro Gly Val Gly Val Pro Gly Val Gly Val Pro Gly Val Gly
            820                 825                 830

Gly Ala Gly Ala Gly Ser Gly Ala Gly Ala Gly Ser Gly Ala Gly Ala
        835                 840                 845

Gly Ser Gly Ala Gly Ala Gly Ser Gly Ala Gly Ala Gly Ser Gly Ala
    850                 855                 860

Gly Ala Gly Ser Gly Ala Gly Ala Gly Ser Gly Ala Gly Ala Gly Ser
865                 870                 875                 880

Val Pro Gly Val Gly Val Pro Gly Val Gly Val Pro Gly Val Gly Val
                885                 890                 895

Pro Gly Val Gly Val Pro Gly Val Gly Val Pro Gly Val Gly Val Pro
            900                 905                 910

Gly Val Gly Val Pro Gly Val Gly Val Gly Ala Gly Ala Gly Ser Gly Ala
        915                 920                 925

Gly Ala Gly Ser Gly Ala Gly Ala Gly Ser Gly Ala Gly Ala Gly Ser
    930                 935                 940

Gly Ala Gly Ala Gly Ser Gly Ala Gly Ala Gly Ser Gly Ala Gly Ala
945                 950                 955                 960

Gly Ser Gly Ala Gly Ala Gly Ser
                965

<210> SEQ ID NO 6
<211> LENGTH: 864
<212> TYPE: PRT
<213> ORGANISM: Artificial sequence
<220> FEATURE:
<223> OTHER INFORMATION: Synthetic construct

<400> SEQUENCE: 6

Val Pro Gly Val Gly Val Pro Gly Val Gly Val Pro Gly Val Gly Val
1               5                   10                  15
```

-continued

Pro Gly Val Gly Val Pro Gly Val Gly Val Pro Gly Val Gly Val Pro
                    20                  25                  30

Gly Val Gly Val Pro Gly Val Gly Val Pro Gly Val Gly Val Pro Gly
                35                  40                  45

Val Gly Val Pro Gly Val Gly Val Pro Gly Val Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
                85                  90                  95

Gly Ala Gly Ala Gly Ser Gly Ala Gly Ala Gly Ser Val Pro Gly Val
                100                 105                 110

Gly Val Pro Gly Val Gly Val Pro Gly Val Gly Val Pro Gly Val Gly
                115                 120                 125

Val Pro Gly Val Gly Val Pro Gly Val Gly Val Pro Gly Val Gly Val
                130                 135                 140

Pro Gly Val Gly Val Pro Gly Val Gly Val Pro Gly Val Gly Val Pro
145                 150                 155                 160

Gly Val Gly Val Pro Gly Val Gly Ala Gly Ala Gly Ser Gly Ala
                165                 170                 175

Gly Ala Gly Ser Gly Ala Gly Ala Gly Ser Gly Ala Gly Ala Gly Ser
                180                 185                 190

Gly Ala Gly Ala Gly Ser Gly Ala Gly Ala Gly Ser Gly Ala Gly Ala
                195                 200                 205

Gly Ser Gly Ala Gly Ala Gly Ser Val Pro Gly Val Gly Val Pro Gly
                210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
                260                 265                 270

Pro Gly Val Gly Gly Ala Gly Ala Gly Ser Gly Ala Gly Ala Gly Ser
                275                 280                 285

Gly Ala Gly Ala Gly Ser Gly Ala Gly Ala Gly Ser Gly Ala Gly Ala
290                 295                 300

Gly Ser Gly Ala Gly Ala Gly Ser Gly Ala Gly Ala Gly Ser Gly Ala
305                 310                 315                 320

Gly Ala Gly Ser Val Pro Gly Val Gly Val Pro Gly Val Gly Val Pro
                325                 330                 335

Gly Val Gly Val Pro Gly Val Gly Val Pro Gly Val Gly Val Pro Gly
                340                 345                 350

Val Gly Val Pro Gly Val Gly Val Pro Gly Val Gly Val Pro Gly Val
                355                 360                 365

Gly Val Pro Gly Val Gly Val Pro Gly Val Gly Val Pro Gly Val Gly
                370                 375                 380

Gly Ala Gly Ala Gly Ser Gly Ala Gly Ala Gly Ser Gly Ala Gly Ala
385                 390                 395                 400

Gly Ser Gly Ala Gly Ala Gly Ser Gly Ala Gly Ala Gly Ser Gly Ala
                405                 410                 415

Gly Ala Gly Ser Gly Ala Gly Ala Gly Ser Gly Ala Gly Ala Gly Ser
                420                 425                 430

Val Pro Gly Val Gly Val Pro Gly Val Gly Val Pro Gly Val Gly Val

-continued

```
                435                 440                 445
Pro Gly Val Gly Val Pro Gly Val Gly Val Pro Gly Val Gly Val Pro
450                 455                 460
Gly Val Gly Val Pro Gly Val Gly Val Pro Gly Val Gly Val Pro Gly
465                 470                 475                 480
Val Gly Val Pro Gly Val Gly Val Pro Gly Val Gly Ala Gly Ala
                485                 490                 495
Gly Ser Gly Ala Gly Ala Gly Ser Gly Ala Gly Ala Gly Ser Gly Ala
                500                 505                 510
Gly Ala Gly Ser Gly Ala Gly Ala Gly Ser Gly Ala Gly Ala Gly Ser
                515                 520                 525
Gly Ala Gly Ala Gly Ser Gly Ala Gly Ala Gly Ser Val Pro Gly Val
                530                 535                 540
Gly Val Pro Gly Val Gly Val Pro Gly Val Gly Val Pro Gly Val Gly
545                 550                 555                 560
Val Pro Gly Val Gly Val Pro Gly Val Gly Val Pro Gly Val Gly Val
                565                 570                 575
Pro Gly Val Gly Val Pro Gly Val Gly Val Pro Gly Val Gly Val Pro
                580                 585                 590
Gly Val Gly Val Pro Gly Val Gly Ala Gly Ala Gly Ser Gly Ala
                595                 600                 605
Gly Ala Gly Ser Gly Ala Gly Ala Gly Ser Gly Ala Gly Ala Gly Ser
                610                 615                 620
Gly Ala Gly Ala Gly Ser Gly Ala Gly Ala Gly Ser Gly Ala Gly Ala
625                 630                 635                 640
Gly Ser Gly Ala Gly Ala Gly Ser Val Pro Gly Val Gly Val Pro Gly
                645                 650                 655
Val Gly Val Pro Gly Val Gly Val Pro Gly Val Gly Val Pro Gly Val
                660                 665                 670
Gly Val Pro Gly Val Gly Val Pro Gly Val Gly Val Pro Gly Val Gly
                675                 680                 685
Val Pro Gly Val Gly Val Pro Gly Val Gly Val Pro Gly Val Gly Val
                690                 695                 700
Pro Gly Val Gly Gly Ala Gly Ala Gly Ser Gly Ala Gly Ala Gly Ser
705                 710                 715                 720
Gly Ala Gly Ala Gly Ser Gly Ala Gly Ala Gly Ser Gly Ala Gly Ala
                725                 730                 735
Gly Ser Gly Ala Gly Ala Gly Ser Gly Ala Gly Ala Gly Ser Gly Ala
                740                 745                 750
Gly Ala Gly Ser Val Pro Gly Val Gly Val Pro Gly Val Gly Val Pro
                755                 760                 765
Gly Val Gly Val Pro Gly Val Gly Val Pro Gly Val Gly Val Pro Gly
                770                 775                 780
Val Gly Val Pro Gly Val Gly Val Pro Gly Val Gly Val Pro Gly Val
785                 790                 795                 800
Gly Val Pro Gly Val Gly Val Pro Gly Val Gly Val Pro Gly Val Gly
                805                 810                 815
Gly Ala Gly Ala Gly Ser Gly Ala Gly Ala Gly Ser Gly Ala Gly Ala
                820                 825                 830
Gly Ser Gly Ala Gly Ala Gly Ser Gly Ala Gly Ala Gly Ser Gly Ala
                835                 840                 845
Gly Ala Gly Ser Gly Ala Gly Ala Gly Ser Gly Ala Gly Ala Gly Ser
                850                 855                 860
```

<210> SEQ ID NO 7
<211> LENGTH: 896
<212> TYPE: PRT
<213> ORGANISM: Artificial sequence
<220> FEATURE:
<223> OTHER INFORMATION: Synthetic construct

<400> SEQUENCE: 7

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
50                  55                  60

Gly Val Pro Gly Val Gly Val Pro Gly Val Gly Val Pro Gly Val Gly
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

Val Pro Gly Val Gly Val Pro Gly Val Gly Val Pro Gly Val Gly Val
130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Gly Ala Gly Ala Gly Ser Gly Ala Gly Ala Gly Ser Gly Ala Gly Ala
210                 215                 220

Gly Ser Gly Ala Gly Ala Gly Ser Gly Ala Gly Ala Gly Ser Gly Ala
225                 230                 235                 240

Gly Ala Gly Ser Gly Ala Gly Ala Gly Ser Gly Ala Gly Ala Gly Ser
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Val Gly Val Pro Gly
    290                 295                 300

Val Gly Val Pro Gly Val Gly Val Pro Gly Val Gly Val Pro Gly Val
305                 310                 315                 320

Gly Val Pro Gly Val Gly Val Pro Gly Val Gly Val Pro Gly Val Gly
                325                 330                 335

Gly Ala Gly Ala Gly Ser Gly Ala Gly Ala Gly Ser Gly Ala Gly Ala
            340                 345                 350

Gly Ser Gly Ala Gly Ala Gly Ser Gly Ala Gly Ala Gly Ser Gly Ala
        355                 360                 365

```
Gly Ala Gly Ser Gly Ala Gly Ala Gly Ser Gly Ala Gly Ala Gly Ser
        370                 375                 380

Val Pro Gly Val Gly Val Pro Gly Val Gly Val Pro Gly Val Gly Val
385                 390                 395                 400

Pro Gly Val Gly Val Pro Gly Val Gly Val Pro Gly Val Gly Val Pro
                405                 410                 415

Gly Val Gly Val Pro Gly Val Gly Val Pro Gly Val Gly Val Pro Gly
                420                 425                 430

Val Gly Val Pro Gly Val Gly Val Pro Gly Val Gly Val Pro Gly Val
                435                 440                 445

Gly Val Pro Gly Val Gly Val Pro Gly Val Gly Val Pro Gly Val Gly
        450                 455                 460

Gly Ala Gly Ala Gly Ser Gly Ala Gly Ala Gly Ser Gly Ala Gly Ala
465                 470                 475                 480

Gly Ser Gly Ala Gly Ala Gly Ser Gly Ala Gly Ala Gly Ser Gly Ala
                485                 490                 495

Gly Ala Gly Ser Gly Ala Gly Ala Gly Ser Gly Ala Gly Ala Gly Ser
                500                 505                 510

Val Pro Gly Val Gly Val Pro Gly Val Gly Val Pro Gly Val Gly Val
        515                 520                 525

Pro Gly Val Gly Val Pro Gly Val Gly Val Pro Gly Val Gly Val Pro
        530                 535                 540

Gly Val Gly Val Pro Gly Val Gly Val Pro Gly Val Gly Val Pro Gly
545                 550                 555                 560

Val Gly Val Pro Gly Val Gly Val Pro Gly Val Gly Val Pro Gly Val
                565                 570                 575

Gly Val Pro Gly Val Gly Val Pro Gly Val Gly Val Pro Gly Val Gly
                580                 585                 590

Gly Ala Gly Ala Gly Ser Gly Ala Gly Ala Gly Ser Gly Ala Gly Ala
        595                 600                 605

Gly Ser Gly Ala Gly Ala Gly Ser Gly Ala Gly Ala Gly Ser Gly Ala
        610                 615                 620

Gly Ala Gly Ser Gly Ala Gly Ala Gly Ser Gly Ala Gly Ala Gly Ser
625                 630                 635                 640

Val Pro Gly Val Gly Val Pro Gly Val Gly Val Pro Gly Val Gly Val
                645                 650                 655

Pro Gly Val Gly Val Pro Gly Val Gly Val Pro Gly Val Gly Val Pro
        660                 665                 670

Gly Val Gly Val Pro Gly Val Gly Val Pro Gly Val Gly Val Pro Gly
        675                 680                 685

Val Gly Val Pro Gly Val Gly Val Pro Gly Val Gly Val Pro Gly Val
        690                 695                 700

Gly Val Pro Gly Val Gly Val Pro Gly Val Gly Val Pro Gly Val Gly
705                 710                 715                 720

Gly Ala Gly Ala Gly Ser Gly Ala Gly Ala Gly Ser Gly Ala Gly Ala
                725                 730                 735

Gly Ser Gly Ala Gly Ala Gly Ser Gly Ala Gly Ala Gly Ser Gly Ala
                740                 745                 750

Gly Ala Gly Ser Gly Ala Gly Ala Gly Ser Gly Ala Gly Ala Gly Ser
                755                 760                 765

Val Pro Gly Val Gly Val Pro Gly Val Gly Val Pro Gly Val Gly Val
        770                 775                 780
```

Pro Gly Val Gly Val Pro Gly Val Gly Val Pro Gly Val Pro
785                 790                 795                 800

Gly Val Gly Val Pro Gly Val Gly Val Pro Gly Val Gly Val Pro Gly
            805                 810                 815

Val Gly Val Pro Gly Val Gly Val Pro Gly Val Gly Val Pro Gly Val
        820                 825                 830

Gly Val Pro Gly Val Gly Val Pro Gly Val Gly Val Pro Gly Val Gly
    835                 840                 845

Gly Ala Gly Ala Gly Ser Gly Ala Gly Ala Gly Ser Gly Ala Gly Ala
    850                 855                 860

Gly Ser Gly Ala Gly Ala Gly Ser Gly Ala Gly Ala Gly Ser Gly Ala
865                 870                 875                 880

Gly Ala Gly Ser Gly Ala Gly Ala Gly Ser Gly Ala Gly Ala Gly Ser
            885                 890                 895

<210> SEQ ID NO 8
<211> LENGTH: 1040
<212> TYPE: PRT
<213> ORGANISM: Artificial sequence
<220> FEATURE:
<223> OTHER INFORMATION: Synthetic construct

<400> SEQUENCE: 8

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Gly Ala Gly Ala Gly Ser Gly Ala Gly Ala Gly Ser Gly Ala Gly Ala
                165                 170                 175

Gly Ser Gly Ala Gly Ala Gly Ser Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

-continued

Val Gly Val Pro Gly Val Gly Val Pro Gly Val Gly Val
        260                 265                 270

Gly Val Pro Gly Val Gly Val Pro Gly Val Gly Val Pro Gly Val Gly
            275                 280                 285

Val Pro Gly Val Gly Val Pro Gly Val Gly Val Pro Gly Val Gly Val
        290                 295                 300

Pro Gly Val Gly Val Pro Gly Val Gly Val Pro Gly Val Gly Val Pro
305                 310                 315                 320

Gly Val Gly Val Pro Gly Val Gly Val Pro Gly Val Gly Val Pro Gly
            325                 330                 335

Val Gly Val Pro Gly Val Gly Val Pro Gly Val Gly Val Pro Gly Val
        340                 345                 350

Gly Val Pro Gly Val Gly Val Pro Gly Val Gly Val Pro Gly Val Gly
            355                 360                 365

Gly Ala Gly Ala Gly Ser Gly Ala Gly Ala Gly Ser Gly Ala Gly Ala
        370                 375                 380

Gly Ser Gly Ala Gly Ala Gly Ser Gly Ala Gly Ala Gly Ser Gly Ala
385                 390                 395                 400

Gly Ala Gly Ser Gly Ala Gly Ala Gly Ser Gly Ala Gly Ala Gly Ser
            405                 410                 415

Val Pro Gly Val Gly Val Pro Gly Val Gly Val Pro Gly Val Gly Val
        420                 425                 430

Pro Gly Val Gly Val Pro Gly Val Gly Val Pro Gly Val Gly Val Pro
            435                 440                 445

Gly Val Gly Val Pro Gly Val Gly Val Pro Gly Val Gly Val Pro Gly
        450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
            485                 490                 495

Val Pro Gly Val Gly Val Pro Gly Val Gly Val Pro Gly Val Gly Val
        500                 505                 510

Pro Gly Val Gly Val Pro Gly Val Gly Val Pro Gly Val Gly Val Pro
            515                 520                 525

Gly Val Gly Val Pro Gly Val Gly Val Pro Gly Val Gly Val Pro Gly
        530                 535                 540

Val Gly Val Pro Gly Val Gly Val Pro Gly Val Gly Val Pro Gly Val
545                 550                 555                 560

Gly Val Pro Gly Val Gly Val Pro Gly Val Gly Val Pro Gly Val Gly
            565                 570                 575

Gly Ala Gly Ala Gly Ser Gly Ala Gly Ala Gly Ser Gly Ala Gly Ala
        580                 585                 590

Gly Ser Gly Ala Gly Ala Gly Ser Gly Ala Gly Ala Gly Ser Gly Ala
            595                 600                 605

Gly Ala Gly Ser Gly Ala Gly Ala Gly Ser Gly Ala Gly Ala Gly Ser
        610                 615                 620

Val Pro Gly Val Gly Val Pro Gly Val Gly Val Pro Gly Val Gly Val
625                 630                 635                 640

Pro Gly Val Gly Val Pro Gly Val Gly Val Pro Gly Val Gly Val Pro
            645                 650                 655

Gly Val Gly Val Pro Gly Val Gly Val Pro Gly Val Gly Val Pro Gly
        660                 665                 670

Val Gly Val Pro Gly Val Gly Val Pro Gly Val Gly Val Pro Gly Val 675                 680                 685
Gly Val Pro Gly Val Gly Val Pro Gly Val Gly Val Pro Gly Val Gly
            690                 695                 700

Val Pro Gly Val Gly Val Pro Gly Val Gly Val Pro Gly Val Gly Val
705                 710                 715                 720

Pro Gly Val Gly Val Pro Gly Val Gly Val Pro Gly Val Gly Val Pro
                725                 730                 735

Gly Val Gly Val Pro Gly Val Gly Val Pro Gly Val Gly Val Pro Gly
            740                 745                 750

Val Gly Val Pro Gly Val Gly Val Pro Gly Val Gly Val Pro Gly Val
        755                 760                 765

Gly Val Pro Gly Val Gly Val Pro Gly Val Gly Val Pro Gly Val Gly
    770                 775                 780

Gly Ala Gly Ala Gly Ser Gly Ala Gly Ala Gly Ser Gly Ala Gly Ala
785                 790                 795                 800

Gly Ser Gly Ala Gly Ala Gly Ser Gly Ala Gly Ala Gly Ser Gly Ala
                805                 810                 815

Gly Ala Gly Ser Gly Ala Gly Ala Gly Ser Gly Ala Gly Ala Gly Ser
            820                 825                 830

Val Pro Gly Val Gly Val Pro Gly Val Gly Val Pro Gly Val Gly Val
        835                 840                 845

Pro Gly Val Gly Val Pro Gly Val Gly Val Pro Gly Val Gly Val Pro
850                 855                 860

Gly Val Gly Val Pro Gly Val Gly Val Pro Gly Val Gly Val Pro Gly
865                 870                 875                 880

Val Gly Val Pro Gly Val Gly Val Pro Gly Val Gly Val Pro Gly Val
                885                 890                 895

Gly Val Pro Gly Val Gly Val Pro Gly Val Gly Val Pro Gly Val Gly
            900                 905                 910

Val Pro Gly Val Gly Val Pro Gly Val Gly Val Pro Gly Val Gly Val
        915                 920                 925

Pro Gly Val Gly Val Pro Gly Val Gly Val Pro Gly Val Gly Val Pro
    930                 935                 940

Gly Val Gly Val Pro Gly Val Gly Val Pro Gly Val Gly Val Pro Gly
945                 950                 955                 960

Val Gly Val Pro Gly Val Gly Val Pro Gly Val Gly Val Pro Gly Val
                965                 970                 975

Gly Val Pro Gly Val Gly Val Pro Gly Val Gly Val Pro Gly Val Gly
            980                 985                 990

Gly Ala Gly Ala Gly Ser Gly Ala  Gly Ala Gly Ser Gly  Ala Gly Ala
        995                 1000                1005

Gly Ser  Gly Ala Gly Ala Gly  Ser Gly Ala Gly Ala  Gly Ser Gly
    1010                1015                1020

Ala Gly  Ala Gly Ser Gly Ala  Gly Ala Gly Ser Gly  Ala Gly Ala
    1025                1030                1035

Gly Ser
    1040

<210> SEQ ID NO 9
<211> LENGTH: 1002
<212> TYPE: PRT
<213> ORGANISM: Artificial sequence
<220> FEATURE:
<223> OTHER INFORMATION: Synthetic construct

<400> SEQUENCE: 9

```
Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
            20                  25                  30
Gly Ala Gly Ser Gly Ala Gly Ala Gly Ser Gly Ala Gly Ala Gly Ser
        35                  40                  45
Gly Ala Gly Ala Gly Ser Gly Ala Gly Ala Gly Ser Gly Ala Gly Ala
    50                  55                  60
Gly Ser Gly Ala Gly Ala Gly Ser Gly Ala Ala Val Thr Gly Arg Gly
65                  70                  75                  80
Asp Ser Pro Ala Ser Ala Ala Gly Tyr Gly Ala Gly Ala Gly Ser Gly
                85                  90                  95
Ala Gly Ala Gly Ser Gly Ala Gly Ala Gly Ser Gly Ala Gly Ala Gly
            100                 105                 110
Ser Gly Ala Gly Ala Gly Ser Gly Val Gly Val Gly Pro Gly Val Gly
        115                 120                 125
Val Gly Pro Gly Val Gly Val Gly Pro Gly Val Gly Val Gly Pro Gly
    130                 135                 140
Val Gly Val Gly Pro Gly Val Gly Val Gly Pro Gly Val Gly Val Gly
145                 150                 155                 160
Pro Gly Val Gly Val Gly Pro Gly Ala Gly Ala Gly Ser Gly Ala Gly
                165                 170                 175
Ala Gly Ser Gly Ala Gly Ala Gly Ser Gly Ala Gly Ala Gly Ser Gly
            180                 185                 190
Ala Gly Ala Gly Ser Gly Ala Gly Ala Gly Ser Gly Ala Gly Ala Gly
        195                 200                 205
Ser Gly Ala Gly Ala Gly Ser Gly Ala Gly Ala Gly Ser Gly Ala Gly
    210                 215                 220
Ala Gly Ser Gly Ala Gly Ala Gly Ser Gly Ala Gly Ala Gly Ser Gly
225                 230                 235                 240
Ala Ala Val Thr Gly Arg Gly Asp Ser Pro Ala Ser Ala Ala Gly Tyr
                245                 250                 255
Gly Ala Gly Ala Gly Ser Gly Ala Gly Ala Gly Ser Gly Ala Gly Ala
            260                 265                 270
Gly Ser Gly Ala Gly Ala Gly Ser Gly Ala Gly Ala Gly Ser Gly Val
        275                 280                 285
Gly Val Gly Pro Gly Val Gly Val Gly Pro Gly Val Gly Val Gly Pro
    290                 295                 300
Gly Val Gly Val Gly Pro Gly Val Gly Val Gly Pro Gly Val Gly Val
305                 310                 315                 320
Gly Pro Gly Val Gly Val Gly Pro Gly Val Gly Val Gly Pro Gly Ala
                325                 330                 335
Gly Ala Gly Ser Gly Ala Gly Ala Gly Ser Gly Ala Gly Ala Gly Ser
            340                 345                 350
Gly Ala Gly Ala Gly Ser Gly Ala Gly Ala Gly Ser Gly Ala Gly Ala
        355                 360                 365
Gly Ser Gly Ala Gly Ala Gly Ser Gly Ala Gly Ala Gly Ser Gly Ala
    370                 375                 380
Gly Ala Gly Ser Gly Ala Gly Ala Gly Ser Gly Ala Gly Ala Gly Ser
385                 390                 395                 400
Gly Ala Gly Ala Gly Ser Gly Ala Ala Val Thr Gly Arg Gly Asp Ser
                405                 410                 415
```

```
Pro Ala Ser Ala Ala Gly Tyr Gly Ala Gly Ala Gly Ser Gly Ala Gly
            420                 425                 430

Ala Gly Ser Gly Ala Gly Ala Gly Ser Gly Ala Gly Ala Gly Ser Gly
            435                 440                 445

Ala Gly Ala Gly Ser Gly Val Gly Val Gly Pro Gly Val Gly Val Gly
            450                 455                 460

Pro Gly Val Gly Val Gly Pro Gly Val Gly Val Gly Pro Gly Val Gly
465                 470                 475                 480

Val Gly Pro Gly Val Gly Val Gly Pro Gly Val Gly Val Gly Pro Gly
            485                 490                 495

Val Gly Val Gly Pro Gly Ala Gly Ala Gly Ser Gly Ala Gly Ala Gly
            500                 505                 510

Ser Gly Ala Gly Ala Gly Ser Gly Ala Gly Ala Gly Ser Gly Ala Gly
            515                 520                 525

Ala Gly Ser Gly Ala Gly Ala Gly Ser Gly Ala Gly Ala Gly Ser Gly
            530                 535                 540

Ala Gly Ala Gly Ser Gly Ala Gly Ala Gly Ser Gly Ala Gly Ala Gly
545                 550                 555                 560

Ser Gly Ala Gly Ala Gly Ser Gly Ala Gly Ala Gly Ser Gly Ala Ala
            565                 570                 575

Val Thr Gly Arg Gly Asp Ser Pro Ala Ser Ala Ala Gly Tyr Gly Ala
            580                 585                 590

Gly Ala Gly Ser Gly Ala Gly Ala Gly Ser Gly Ala Gly Ala Gly Ser
            595                 600                 605

Gly Ala Gly Ala Gly Ser Gly Ala Gly Ala Gly Ser Gly Val Gly Val
            610                 615                 620

Gly Pro Gly Val Gly Val Gly Pro Gly Val Gly Val Gly Pro Gly Val
625                 630                 635                 640

Gly Val Gly Pro Gly Val Gly Val Gly Pro Gly Val Gly Val Gly Pro
            645                 650                 655

Gly Val Gly Val Gly Pro Gly Val Gly Val Gly Pro Gly Ala Gly Ala
            660                 665                 670

Gly Ser Gly Ala Gly Ala Gly Ser Gly Ala Gly Ala Gly Ser Gly Ala
            675                 680                 685

Gly Ala Gly Ser Gly Ala Gly Ala Gly Ser Gly Ala Gly Ala Gly Ser
            690                 695                 700

Gly Ala Gly Ala Gly Ser Gly Ala Gly Ala Gly Ser Gly Ala Gly Ala
705                 710                 715                 720

Gly Ser Gly Ala Gly Ala Gly Ser Gly Ala Gly Ala Gly Ser Gly Ala
            725                 730                 735

Gly Ala Gly Ser Gly Ala Ala Val Thr Gly Arg Gly Asp Ser Pro Ala
            740                 745                 750

Ser Ala Ala Gly Tyr Gly Ala Gly Ala Gly Ser Gly Ala Gly Ala Gly
            755                 760                 765

Ser Gly Ala Gly Ala Gly Ser Gly Ala Gly Ala Gly Ser Gly Ala Gly
            770                 775                 780

Ala Gly Ser Gly Val Gly Val Gly Pro Gly Val Gly Val Gly Pro Gly
785                 790                 795                 800

Val Gly Val Gly Pro Gly Val Gly Val Gly Pro Gly Val Gly Val Gly
            805                 810                 815

Pro Gly Val Gly Val Gly Pro Gly Val Gly Val Gly Pro Gly Val Gly
            820                 825                 830
```

```
Val Gly Pro Gly Ala Gly Ala Gly Ser Gly Ala Gly Ser Gly
        835                 840                 845

Ala Gly Ala Gly Ser Gly Ala Gly Ser Gly Ala Gly Ala Gly
    850                 855                 860

Ser Gly Ala Gly Ala Gly Ser Gly Ala Gly Ala Gly Ser Gly Ala Gly
865                 870                 875                 880

Ala Gly Ser Gly Ala Gly Ala Gly Ser Gly Ala Gly Ala Gly Ser Gly
                885                 890                 895

Ala Gly Ala Gly Ser Gly Ala Gly Ala Gly Ser Gly Ala Ala Val Thr
            900                 905                 910

Gly Arg Gly Asp Ser Pro Ala Ser Ala Ala Gly Tyr Gly Ala Gly Ala
        915                 920                 925

Gly Ser Gly Ala Gly Ala Gly Ser Gly Ala Gly Ala Gly Ser Gly Ala
    930                 935                 940

Gly Ala Gly Ser Gly Ala Gly Ala Gly Ser Gly Val Gly Val Gly Pro
945                 950                 955                 960

Gly Val Gly Val Gly Pro Gly Val Gly Val Pro Gly Val Gly Val
                965                 970                 975

Gly Pro Gly Val Gly Val Gly Pro Gly Val Gly Val Gly Pro Gly Val
        980                 985                 990

Gly Val Gly Pro Gly Val Gly Val  Gly Pro
        995                 1000

<210> SEQ ID NO 10
<211> LENGTH: 312
<212> TYPE: PRT
<213> ORGANISM: Artificial sequence
<220> FEATURE:
<223> OTHER INFORMATION: Synthetic construct

<400> SEQUENCE: 10

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
                20                  25                  30

Gly Lys Gly Val Pro Gly Val Gly Val Pro Gly Val Gly Val Pro Gly
            35                  40                  45

Val Gly Val Pro Gly Ala Gly Ala Gly Ser Gly Ala Gly Ala Gly Ser
    50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
        115                 120                 125

Gly Val Pro Gly Val Gly Val Pro Gly Lys Gly Val Pro Gly Val Gly
    130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val
                165                 170                 175

Val Pro Gly Val Gly Val Pro Gly Val Gly Val Pro Gly Lys Gly Val
        180                 185                 190
```

-continued

Pro Gly Val Gly Val Pro Gly Val Gly Val Pro Gly Val Gly Val Pro
            195                 200                 205
Gly Ala Gly Ala Gly Ser Gly Ala Gly Ala Gly Ser Gly Val Gly Val
    210                 215                 220
Pro Gly Val Gly Val Pro Gly Val Gly Val Pro Gly Val Gly Val Pro
225                 230                 235                 240
Gly Lys Gly Val Pro Gly Val Gly Val Pro Gly Val Gly Val Pro Gly
            245                 250                 255
Val Gly Val Pro Gly Ala Gly Ala Gly Ser Gly Ala Gly Ala Gly Ser
        260                 265                 270
Gly Val Gly Val Pro Gly Val Gly Val Pro Gly Val Gly Val Pro Gly
    275                 280                 285
Val Gly Val Pro Gly Lys Gly Val Pro Gly Val Gly Val Pro Gly Val
        290                 295                 300
Gly Val Pro Gly Val Gly Val Pro
305                 310

<210> SEQ ID NO 11
<211> LENGTH: 624
<212> TYPE: PRT
<213> ORGANISM: Artificial sequence
<220> FEATURE:
<223> OTHER INFORMATION: Synthetic construct

<400> SEQUENCE: 11

Gly Ala Gly Ala Gly Ser Gly Ala Gly Ala Gly Ser Gly Val Gly Val
1               5                   10                  15
Pro Gly Val Gly Val Pro Gly Val Gly Val Pro Gly Val Gly Val Pro
            20                  25                  30
Gly Lys Gly Val Pro Gly Val Gly Val Pro Gly Val Gly Val Pro Gly
        35                  40                  45
Val Gly Val Pro Gly Ala Gly Ala Gly Ser Gly Ala Gly Ala Gly Ser
    50                  55                  60
Gly Val Gly Val Pro Gly Val Gly Val Pro Gly Val Gly Val Pro Gly
65                  70                  75                  80
Val Gly Val Pro Gly Lys Gly Val Pro Gly Val Gly Val Pro Gly Val
                85                  90                  95
Gly Val Pro Gly Val Gly Val Pro Gly Ala Gly Ala Gly Ser Gly Ala
            100                 105                 110
Gly Ala Gly Ser Gly Val Gly Val Pro Gly Val Gly Val Pro Gly Val
        115                 120                 125
Gly Val Pro Gly Val Gly Val Pro Gly Lys Gly Val Pro Gly Val Gly
    130                 135                 140
Val Pro Gly Val Gly Val Pro Gly Val Gly Val Pro Gly Ala Gly Ala
145                 150                 155                 160
Gly Ser Gly Ala Gly Ala Gly Ser Gly Val Gly Val Pro Gly Val Gly
                165                 170                 175
Val Pro Gly Val Gly Val Pro Gly Val Gly Val Pro Gly Lys Gly Val
            180                 185                 190
Pro Gly Val Gly Val Pro Gly Val Gly Val Pro Gly Val Gly Val Pro
        195                 200                 205
Gly Ala Gly Ala Gly Ser Gly Ala Gly Ala Gly Ser Gly Val Gly Val
    210                 215                 220
Pro Gly Val Gly Val Pro Gly Val Gly Val Pro Gly Val Gly Val Pro
225                 230                 235                 240

```
Gly Lys Gly Val Pro Gly Val Gly Val Pro Gly Val Gly Val Pro Gly
            245                 250                 255

Val Gly Val Pro Gly Ala Gly Ala Gly Ser Gly Ala Gly Ala Gly Ser
        260                 265                 270

Gly Val Gly Val Pro Gly Val Gly Val Pro Gly Val Gly Val Pro Gly
        275                 280                 285

Val Gly Val Pro Gly Lys Gly Val Pro Gly Val Gly Val Pro Gly Val
        290                 295                 300

Gly Val Pro Gly Val Gly Val Pro Gly Ala Gly Ala Gly Ser Gly Ala
305                 310                 315                 320

Gly Ala Gly Ser Gly Val Gly Val Pro Gly Val Gly Val Pro Gly Val
                325                 330                 335

Gly Val Pro Gly Val Gly Val Pro Gly Lys Gly Val Pro Gly Val Gly
            340                 345                 350

Val Pro Gly Val Gly Val Pro Gly Val Gly Val Pro Gly Ala Gly Ala
        355                 360                 365

Gly Ser Gly Ala Gly Ala Gly Ser Gly Val Gly Val Pro Gly Val Gly
    370                 375                 380

Val Pro Gly Val Gly Val Pro Gly Val Gly Val Pro Gly Lys Gly Val
385                 390                 395                 400

Pro Gly Val Gly Val Pro Gly Val Gly Val Pro Gly Val Gly Val Pro
                405                 410                 415

Gly Ala Gly Ala Gly Ser Gly Ala Gly Ala Gly Ser Gly Val Gly Val
            420                 425                 430

Pro Gly Val Gly Val Pro Gly Val Gly Val Pro Gly Val Gly Val Pro
        435                 440                 445

Gly Lys Gly Val Pro Gly Val Gly Val Pro Gly Val Gly Val Pro Gly
    450                 455                 460

Val Gly Val Pro Gly Ala Gly Ala Gly Ser Gly Ala Gly Ala Gly Ser
465                 470                 475                 480

Gly Val Gly Val Pro Gly Val Gly Val Pro Gly Val Gly Val Pro Gly
                485                 490                 495

Val Gly Val Pro Gly Lys Gly Val Pro Gly Val Gly Val Pro Gly Val
            500                 505                 510

Gly Val Pro Gly Val Gly Val Pro Gly Ala Gly Ala Gly Ser Gly Ala
        515                 520                 525

Gly Ala Gly Ser Gly Val Gly Val Pro Gly Val Gly Val Pro Gly Val
    530                 535                 540

Gly Val Pro Gly Val Gly Val Pro Gly Lys Gly Val Pro Gly Val Gly
545                 550                 555                 560

Val Pro Gly Val Gly Val Pro Gly Val Gly Val Pro Gly Ala Gly Ala
                565                 570                 575

Gly Ser Gly Ala Gly Ala Gly Ser Gly Val Gly Val Pro Gly Val Gly
            580                 585                 590

Val Pro Gly Val Gly Val Pro Gly Val Gly Val Pro Gly Lys Gly Val
        595                 600                 605

Pro Gly Val Gly Val Pro Gly Val Gly Val Pro Gly Val Gly Val Pro
    610                 615                 620

<210> SEQ ID NO 12
<211> LENGTH: 936
<212> TYPE: PRT
<213> ORGANISM: Artificial sequence
<220> FEATURE:
<223> OTHER INFORMATION: Synthetic construct
```

<400> SEQUENCE: 12

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
            20                  25                  30

Gly Lys Gly Val Pro Gly Val Gly Val Pro Gly Val Gly Val Pro Gly
        35                  40                  45

Val Gly Val Pro Gly Ala Gly Ala Gly Ser Gly Ala Gly Ala Gly Ser
50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
            85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
            115                 120                 125

Gly Val Pro Gly Val Gly Val Pro Gly Lys Gly Val Pro Gly Val Gly
            130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val Gly
            165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
            195                 200                 205

Gly Ala Gly Ala Gly Ser Gly Ala Gly Ala Gly Ser Gly Val Gly Val
            210                 215                 220

Pro Gly Val Gly Val Pro Gly Val Gly Val Pro Gly Val Gly Val Pro
225                 230                 235                 240

Gly Lys Gly Val Pro Gly Val Gly Val Pro Gly Val Gly Val Pro Gly
            245                 250                 255

Val Gly Val Pro Gly Ala Gly Ala Gly Ser Gly Ala Gly Ala Gly Ser
            260                 265                 270

Gly Val Gly Val Pro Gly Val Gly Val Pro Gly Val Gly Val Pro Gly
            275                 280                 285

Val Gly Val Pro Gly Lys Gly Val Pro Gly Val Gly Val Pro Gly Val
            290                 295                 300

Gly Val Pro Gly Val Gly Val Pro Gly Ala Gly Ala Gly Ser Gly Ala
305                 310                 315                 320

Gly Ala Gly Ser Gly Val Gly Val Pro Gly Val Gly Val Pro Gly Val
            325                 330                 335

Gly Val Pro Gly Val Gly Val Pro Gly Lys Gly Val Pro Gly Val Gly
            340                 345                 350

Val Pro Gly Val Gly Val Pro Gly Val Gly Val Pro Gly Ala Gly Ala
            355                 360                 365

Gly Ser Gly Ala Gly Ala Gly Ser Gly Val Gly Val Pro Gly Val Gly
            370                 375                 380

Val Pro Gly Val Gly Val Pro Gly Val Gly Val Pro Gly Lys Gly Val
385                 390                 395                 400

Pro Gly Val Gly Val Pro Gly Val Gly Val Pro Gly Val Gly Val Pro

```
                405                 410                 415
Gly Ala Gly Ala Gly Ser Gly Ala Gly Ala Gly Ser Gly Val Gly Val
            420                 425                 430
Pro Gly Val Gly Val Pro Gly Val Gly Val Pro Gly Val Gly Val Pro
            435                 440                 445
Gly Lys Gly Val Pro Gly Val Gly Val Pro Gly Val Gly Val Pro Gly
            450                 455                 460
Val Gly Val Pro Gly Ala Gly Ala Gly Ser Gly Ala Gly Ala Gly Ser
465                 470                 475                 480
Gly Val Gly Val Pro Gly Val Gly Val Pro Gly Val Gly Val Pro Gly
            485                 490                 495
Val Gly Val Pro Gly Lys Gly Val Pro Gly Val Gly Val Pro Gly Val
            500                 505                 510
Gly Val Pro Gly Val Gly Val Pro Gly Ala Gly Ala Gly Ser Gly Ala
            515                 520                 525
Gly Ala Gly Ser Gly Val Gly Val Pro Gly Val Gly Val Pro Gly Val
            530                 535                 540
Gly Val Pro Gly Val Gly Val Pro Gly Lys Gly Val Pro Gly Val Gly
545                 550                 555                 560
Val Pro Gly Val Gly Val Pro Gly Val Gly Val Pro Gly Ala Gly Ala
            565                 570                 575
Gly Ser Gly Ala Gly Ala Gly Ser Gly Val Gly Val Pro Gly Val Gly
            580                 585                 590
Val Pro Gly Val Gly Val Pro Gly Val Gly Val Pro Gly Lys Gly Val
            595                 600                 605
Pro Gly Val Gly Val Pro Gly Val Gly Val Pro Gly Val Gly Val Pro
            610                 615                 620
Gly Ala Gly Ala Gly Ser Gly Ala Gly Ala Gly Ser Gly Val Gly Val
625                 630                 635                 640
Pro Gly Val Gly Val Pro Gly Val Gly Val Pro Gly Val Gly Val Pro
            645                 650                 655
Gly Lys Gly Val Pro Gly Val Gly Val Pro Gly Val Gly Val Pro Gly
            660                 665                 670
Val Gly Val Pro Gly Ala Gly Ala Gly Ser Gly Ala Gly Ala Gly Ser
            675                 680                 685
Gly Val Gly Val Pro Gly Val Gly Val Pro Gly Val Gly Val Pro Gly
            690                 695                 700
Val Gly Val Pro Gly Lys Gly Val Pro Gly Val Gly Val Pro Gly Val
705                 710                 715                 720
Gly Val Pro Gly Val Gly Val Pro Gly Ala Gly Ala Gly Ser Gly Ala
            725                 730                 735
Gly Ala Gly Ser Gly Val Gly Val Pro Gly Val Gly Val Pro Gly Val
            740                 745                 750
Gly Val Pro Gly Val Gly Val Pro Gly Lys Gly Val Pro Gly Val Gly
            755                 760                 765
Val Pro Gly Val Gly Val Pro Gly Val Gly Val Pro Gly Ala Gly Ala
            770                 775                 780
Gly Ser Gly Ala Gly Ala Gly Ser Gly Val Gly Val Pro Gly Val Gly
785                 790                 795                 800
Val Pro Gly Val Gly Val Pro Gly Val Gly Val Pro Gly Lys Gly Val
            805                 810                 815
Pro Gly Val Gly Val Pro Gly Val Gly Val Pro Gly Val Gly Val Pro
            820                 825                 830
```

```
Gly Ala Gly Ala Gly Ser Gly Ala Gly Ala Gly Ser Gly Val Gly Val
            835                 840                 845

Pro Gly Val Gly Val Pro Gly Val Gly Val Pro Gly Val Gly Val Pro
        850                 855                 860

Gly Lys Gly Val Pro Gly Val Gly Val Pro Gly Val Gly Val Pro Gly
865                 870                 875                 880

Val Gly Val Pro Gly Ala Gly Ala Gly Ser Gly Ala Gly Ala Gly Ser
                885                 890                 895

Gly Val Gly Val Pro Gly Val Gly Val Pro Gly Val Gly Val Pro Gly
            900                 905                 910

Val Gly Val Pro Gly Lys Gly Val Pro Gly Val Gly Val Pro Gly Val
        915                 920                 925

Gly Val Pro Gly Val Gly Val Pro
    930                 935

<210> SEQ ID NO 13
<211> LENGTH: 896
<212> TYPE: PRT
<213> ORGANISM: Artificial sequence
<220> FEATURE:
<223> OTHER INFORMATION: Synthetic construct

<400> SEQUENCE: 13

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
            20                  25                  30

Gly Lys Gly Val Pro Gly Val Gly Val Pro Gly Val Gly Val Pro Gly
        35                  40                  45

Val Gly Val Pro Gly Ala Gly Ala Gly Ser Gly Ala Gly Ala Gly Ser
    50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
        115                 120                 125

Gly Val Pro Gly Val Gly Val Pro Gly Lys Gly Val Pro Gly Val Gly
    130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val Gly
                165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
        195                 200                 205

Gly Ala Gly Ala Gly Ser Gly Ala Gly Ala Gly Ser Gly Val Gly Val
    210                 215                 220

Pro Gly Val Gly Val Pro Gly Val Gly Val Pro Gly Val Gly Val Pro
225                 230                 235                 240

Gly Lys Gly Val Pro Gly Val Gly Val Pro Gly Val Gly Val Pro Gly
                245                 250                 255
```

-continued

Val Gly Val Pro Gly Ala Gly Ala Gly Ser Gly Ala Gly Ala Gly Ser
            260                 265                 270

Gly Val Gly Val Pro Gly Val Gly Val Pro Gly Val Gly Val Pro Gly
        275                 280                 285

Val Gly Val Pro Gly Lys Gly Val Pro Gly Val Gly Val Pro Gly Val
290                 295                 300

Gly Val Pro Gly Val Gly Val Pro Gly Ala Gly Ala Gly Ser Gly Ala
305                 310                 315                 320

Gly Ala Gly Ser Gly Val Gly Val Pro Gly Val Gly Val Pro Gly Val
            325                 330                 335

Gly Val Pro Gly Val Gly Val Pro Gly Lys Gly Val Pro Gly Val Gly
            340                 345                 350

Val Pro Gly Val Gly Val Pro Gly Val Gly Val Pro Gly Ala Gly Ala
        355                 360                 365

Gly Ser Gly Ala Gly Ala Gly Ser Gly Val Gly Val Pro Gly Val Gly
        370                 375                 380

Val Pro Gly Val Gly Val Pro Gly Val Gly Val Pro Gly Lys Gly Val
385                 390                 395                 400

Pro Gly Val Gly Val Pro Gly Val Gly Val Pro Gly Val Gly Val Pro
            405                 410                 415

Gly Ala Gly Ala Gly Ser Gly Ala Gly Ala Gly Ser Gly Val Gly Val
            420                 425                 430

Pro Gly Val Gly Val Pro Gly Val Gly Val Pro Gly Val Gly Val Pro
        435                 440                 445

Gly Lys Gly Val Pro Gly Val Gly Val Pro Gly Val Gly Val Pro Gly
        450                 455                 460

Val Gly Val Pro Gly Ala Gly Ala Gly Ser Gly Ala Gly Ala Gly Ser
465                 470                 475                 480

Gly Val Gly Val Pro Gly Val Gly Val Pro Gly Val Gly Val Pro Gly
            485                 490                 495

Val Gly Val Pro Gly Lys Gly Val Pro Gly Val Gly Val Pro Gly Val
            500                 505                 510

Gly Val Pro Gly Val Gly Val Pro Gly Ala Gly Ala Gly Ser Gly Ala
        515                 520                 525

Gly Ala Gly Ser Gly Val Gly Val Pro Gly Val Gly Val Pro Gly Val
        530                 535                 540

Gly Val Pro Gly Val Gly Val Pro Gly Lys Gly Val Pro Gly Val Gly
545                 550                 555                 560

Val Pro Gly Val Gly Val Pro Gly Val Gly Val Pro Gly Ala Gly Ala
            565                 570                 575

Gly Ser Gly Ala Gly Ala Gly Ser Gly Val Gly Val Pro Gly Val Gly
            580                 585                 590

Val Pro Gly Val Gly Val Pro Gly Val Gly Val Pro Gly Lys Gly Val
        595                 600                 605

Pro Gly Val Gly Val Pro Gly Val Gly Val Pro Gly Val Gly Val Pro
        610                 615                 620

Gly Ala Gly Ala Gly Ser Gly Ala Gly Ala Gly Ser Gly Val Gly Val
625                 630                 635                 640

Pro Gly Val Gly Val Pro Gly Val Gly Val Pro Gly Val Gly Val Pro
            645                 650                 655

Gly Lys Gly Val Pro Gly Val Gly Val Pro Gly Val Gly Val Pro Gly
            660                 665                 670

-continued

Val Gly Val Pro Gly Ala Gly Ala Gly Ser Gly Ala Gly Ala Gly Ser
              675                 680                 685

Gly Val Gly Val Pro Gly Val Gly Val Pro Gly Val Gly Val Pro Gly
690                 695                 700

Val Gly Val Pro Gly Lys Gly Val Pro Gly Val Gly Val Pro Gly Val
705                 710                 715                 720

Gly Val Pro Gly Val Gly Val Pro Gly Ala Gly Ala Gly Ser Gly Ala
              725                 730                 735

Gly Ala Gly Ser Gly Val Gly Val Pro Gly Val Gly Val Pro Gly Val
              740                 745                 750

Gly Val Pro Gly Val Gly Val Pro Gly Lys Gly Val Pro Gly Val Gly
              755                 760                 765

Val Pro Gly Val Gly Val Pro Gly Val Gly Val Pro Gly Ala Gly Ala
              770                 775                 780

Gly Ser Gly Ala Gly Ala Gly Ser Gly Val Gly Val Pro Gly Val Gly
785                 790                 795                 800

Val Pro Gly Val Gly Val Pro Gly Val Gly Val Pro Gly Lys Gly Val
              805                 810                 815

Pro Gly Val Gly Val Pro Gly Val Gly Val Pro Gly Val Gly Val Pro
              820                 825                 830

Gly Ala Gly Ala Gly Ser Gly Ala Gly Ala Gly Ser Gly Val Gly Val
              835                 840                 845

Pro Gly Val Gly Val Pro Gly Val Gly Val Pro Gly Val Gly Val Pro
              850                 855                 860

Gly Lys Gly Val Pro Gly Val Gly Val Pro Gly Val Gly Val Pro Gly
865                 870                 875                 880

Val Gly Val Pro Gly Ala Gly Ala Gly Ser Gly Ala Gly Ala Gly Ser
              885                 890                 895

<210> SEQ ID NO 14
<211> LENGTH: 832
<212> TYPE: PRT
<213> ORGANISM: Artificial sequence
<220> FEATURE:
<223> OTHER INFORMATION: Synthetic construct

<400> SEQUENCE: 14

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
              20                  25                  30

Gly Lys Gly Val Pro Gly Val Gly Val Pro Gly Val Gly Val Pro Gly
              35                  40                  45

Val Gly Val Pro Gly Ala Gly Ala Gly Ser Gly Ala Gly Ala Gly Ser
              50                  55                  60

Gly Ala Gly Ala Gly Ser Gly Ala Gly Ala Gly Ser Gly Val Gly Val
65                  70                  75                  80

Pro Gly Val Gly Val Pro Gly Val Gly Val Pro Gly Val Gly Val Pro
              85                  90                  95

Gly Lys Gly Val Pro Gly Val Gly Val Pro Gly Val Gly Val Pro Gly
              100                 105                 110

Val Gly Val Pro Gly Ala Gly Ala Gly Ser Gly Ala Gly Ala Gly Ser
              115                 120                 125

Gly Ala Gly Ala Gly Ser Gly Ala Gly Ala Gly Ser Gly Val Gly Val
              130                 135                 140

```
Pro Gly Val Gly Val Pro Gly Val Gly Val Pro Gly Val Gly Val Pro
145                 150                 155                 160
Gly Lys Gly Val Pro Gly Val Gly Val Pro Gly Val Gly Val Pro Gly
            165                 170                 175
Val Gly Val Pro Gly Ala Gly Ala Gly Ser Gly Ala Gly Ala Gly Ser
                180                 185                 190
Gly Ala Gly Ala Gly Ser Gly Ala Gly Ala Gly Ser Gly Val Gly Val
            195                 200                 205
Pro Gly Val Gly Val Pro Gly Val Gly Val Pro Gly Val Gly Val Pro
        210                 215                 220
Gly Lys Gly Val Pro Gly Val Gly Val Pro Gly Val Gly Val Pro Gly
225                 230                 235                 240
Val Gly Val Pro Gly Ala Gly Ala Gly Ser Gly Ala Gly Ala Gly Ser
                245                 250                 255
Gly Ala Gly Ala Gly Ser Gly Ala Gly Ala Gly Ser Gly Val Gly Val
            260                 265                 270
Pro Gly Val Gly Val Pro Gly Val Gly Val Pro Gly Val Gly Val Pro
        275                 280                 285
Gly Lys Gly Val Pro Gly Val Gly Val Pro Gly Val Gly Val Pro Gly
            290                 295                 300
Val Gly Val Pro Gly Ala Gly Ala Gly Ser Gly Ala Gly Ala Gly Ser
305                 310                 315                 320
Gly Ala Gly Ala Gly Ser Gly Ala Gly Ala Gly Ser Gly Val Gly Val
            325                 330                 335
Pro Gly Val Gly Val Pro Gly Val Gly Val Pro Gly Val Gly Val Pro
            340                 345                 350
Gly Lys Gly Val Pro Gly Val Gly Val Pro Gly Val Gly Val Pro Gly
            355                 360                 365
Val Gly Val Pro Gly Ala Gly Ala Gly Ser Gly Ala Gly Ala Gly Ser
            370                 375                 380
Gly Ala Gly Ala Gly Ser Gly Ala Gly Ala Gly Ser Gly Val Gly Val
385                 390                 395                 400
Pro Gly Val Gly Val Pro Gly Val Gly Val Pro Gly Val Gly Val Pro
            405                 410                 415
Gly Lys Gly Val Pro Gly Val Gly Val Pro Gly Val Gly Val Pro Gly
            420                 425                 430
Val Gly Val Pro Gly Ala Gly Ala Gly Ser Gly Ala Gly Ala Gly Ser
            435                 440                 445
Gly Ala Gly Ala Gly Ser Gly Ala Gly Ala Gly Ser Gly Val Gly Val
            450                 455                 460
Pro Gly Val Gly Val Pro Gly Val Gly Val Pro Gly Val Gly Val Pro
465                 470                 475                 480
Gly Lys Gly Val Pro Gly Val Gly Val Pro Gly Val Gly Val Pro Gly
            485                 490                 495
Val Gly Val Pro Gly Ala Gly Ala Gly Ser Gly Ala Gly Ala Gly Ser
                500                 505                 510
Gly Ala Gly Ala Gly Ser Gly Ala Gly Ala Gly Ser Gly Val Gly Val
            515                 520                 525
Pro Gly Val Gly Val Pro Gly Val Gly Val Pro Gly Val Gly Val Pro
            530                 535                 540
Gly Lys Gly Val Pro Gly Val Gly Val Pro Gly Val Gly Val Pro Gly
545                 550                 555                 560
Val Gly Val Pro Gly Ala Gly Ala Gly Ser Gly Ala Gly Ala Gly Ser
```

```
                565                 570                 575
Gly Ala Gly Ala Gly Ser Gly Ala Gly Ala Gly Ser Gly Val Gly Val
            580                 585                 590
Pro Gly Val Gly Val Pro Gly Val Gly Val Pro Gly Val Gly Val Pro
        595                 600                 605
Gly Lys Gly Val Pro Gly Val Gly Val Pro Gly Val Gly Val Pro Gly
    610                 615                 620
Val Gly Val Pro Gly Ala Gly Ala Gly Ser Gly Ala Gly Ala Gly Ser
625                 630                 635                 640
Gly Ala Gly Ala Gly Ser Gly Ala Gly Ala Gly Ser Gly Val Gly Val
                645                 650                 655
Pro Gly Val Gly Val Pro Gly Val Gly Val Pro Gly Val Gly Val Pro
            660                 665                 670
Gly Lys Gly Val Pro Gly Val Gly Val Pro Gly Val Gly Val Pro Gly
        675                 680                 685
Val Gly Val Pro Gly Ala Gly Ala Gly Ser Gly Ala Gly Ala Gly Ser
    690                 695                 700
Gly Ala Gly Ala Gly Ser Gly Ala Gly Ala Gly Ser Gly Val Gly Val
705                 710                 715                 720
Pro Gly Val Gly Val Pro Gly Val Gly Val Pro Gly Val Gly Val Pro
                725                 730                 735
Gly Lys Gly Val Pro Gly Val Gly Val Pro Gly Val Gly Val Pro Gly
            740                 745                 750
Val Gly Val Pro Gly Ala Gly Ala Gly Ser Gly Ala Gly Ala Gly Ser
        755                 760                 765
Gly Ala Gly Ala Gly Ser Gly Ala Gly Ala Gly Ser Gly Val Gly Val
    770                 775                 780
Pro Gly Val Gly Val Pro Gly Val Gly Val Pro Gly Val Gly Val Pro
785                 790                 795                 800
Gly Lys Gly Val Pro Gly Val Gly Val Pro Gly Val Gly Val Pro Gly
                805                 810                 815
Val Gly Val Pro Gly Ala Gly Ala Gly Ser Gly Ala Gly Ala Gly Ser
            820                 825                 830

<210> SEQ ID NO 15
<211> LENGTH: 696
<212> TYPE: PRT
<213> ORGANISM: Artificial sequence
<220> FEATURE:
<223> OTHER INFORMATION: Synthetic construct

<400> SEQUENCE: 15

Gly Ala Gly Ala Gly Ser Gly Val Gly Val Pro Gly Val Gly Val Pro
1               5                   10                  15
Gly Val Gly Val Pro Gly Val Gly Val Pro Gly Lys Gly Val Pro Gly
            20                  25                  30
Val Gly Val Pro Gly Val Gly Val Pro Gly Val Gly Val Pro Gly Ala
        35                  40                  45
Gly Ala Gly Ser Gly Ala Gly Ala Gly Ser Gly Ala Gly Ala Gly Ser
    50                  55                  60
Gly Val Gly Val Pro Gly Val Gly Val Pro Gly Val Gly Val Pro Gly
65                  70                  75                  80
Val Gly Val Pro Gly Lys Gly Val Pro Gly Val Gly Val Pro Gly Val
                85                  90                  95
Gly Val Pro Gly Val Gly Val Pro Gly Ala Gly Ala Gly Ser Gly Ala
```

```
                100                 105                 110
Gly Ala Gly Ser Gly Ala Gly Ala Gly Ser Gly Val Gly Val Pro Gly
            115                 120                 125

Val Gly Val Pro Gly Val Gly Val Pro Gly Val Gly Val Pro Gly Lys
            130                 135                 140

Gly Val Pro Gly Val Gly Val Pro Gly Val Gly Val Pro Gly Val Gly
145                 150                 155                 160

Val Pro Gly Ala Gly Ala Gly Ser Gly Ala Gly Ala Gly Ser Gly Ala
                165                 170                 175

Gly Ala Gly Ser Gly Val Gly Val Pro Gly Val Gly Val Pro Gly Val
            180                 185                 190

Gly Val Pro Gly Val Gly Val Pro Gly Lys Gly Val Pro Gly Val Gly
            195                 200                 205

Val Pro Gly Val Gly Val Pro Gly Val Gly Val Pro Gly Ala Gly Ala
            210                 215                 220

Gly Ser Gly Ala Gly Ala Gly Ser Gly Ala Gly Ala Gly Ser Gly Val
225                 230                 235                 240

Gly Val Pro Gly Val Gly Val Pro Gly Val Gly Val Pro Gly Val Gly
                245                 250                 255

Val Pro Gly Lys Gly Val Pro Gly Val Gly Val Pro Gly Val Gly Val
            260                 265                 270

Pro Gly Val Gly Val Pro Gly Ala Gly Ala Gly Ser Gly Ala Gly Ala
            275                 280                 285

Gly Ser Gly Ala Gly Ala Gly Ser Gly Val Gly Val Pro Gly Val Gly
            290                 295                 300

Val Pro Gly Val Gly Val Pro Gly Val Gly Val Pro Gly Lys Gly Val
305                 310                 315                 320

Pro Gly Val Gly Val Pro Gly Val Gly Val Pro Gly Val Gly Val Pro
                325                 330                 335

Gly Ala Gly Ala Gly Ser Gly Ala Gly Ala Gly Ser Gly Ala Gly Ala
            340                 345                 350

Gly Ser Gly Val Gly Val Pro Gly Val Gly Val Pro Gly Val Gly Val
            355                 360                 365

Pro Gly Val Gly Val Pro Gly Lys Gly Val Pro Gly Val Gly Val Pro
            370                 375                 380

Gly Val Gly Val Pro Gly Val Gly Val Pro Gly Ala Gly Ala Gly Ser
385                 390                 395                 400

Gly Ala Gly Ala Gly Ser Gly Ala Gly Ala Gly Ser Gly Val Gly Val
                405                 410                 415

Pro Gly Val Gly Val Pro Gly Val Gly Val Pro Gly Val Gly Val Pro
            420                 425                 430

Gly Lys Gly Val Pro Gly Val Gly Val Pro Gly Val Gly Val Pro Gly
            435                 440                 445

Val Gly Val Pro Gly Ala Gly Ala Gly Ser Gly Ala Gly Ala Gly Ser
            450                 455                 460

Gly Ala Gly Ala Gly Ser Gly Val Gly Val Pro Gly Val Gly Val Pro
465                 470                 475                 480

Gly Val Gly Val Pro Gly Val Gly Val Pro Gly Lys Gly Val Pro Gly
                485                 490                 495

Val Gly Val Pro Gly Val Gly Val Pro Gly Val Gly Val Pro Gly Ala
            500                 505                 510

Gly Ala Gly Ser Gly Ala Gly Ala Gly Ser Gly Ala Gly Ala Gly Ser
            515                 520                 525
```

Gly Val Gly Val Pro Gly Val Gly Val Pro Gly Val Gly Val Pro Gly
                530                 535                 540

Val Gly Val Pro Gly Lys Gly Val Pro Gly Val Gly Val Pro Gly Val
545                 550                 555                 560

Gly Val Pro Gly Val Gly Val Pro Gly Ala Gly Ala Gly Ser Gly Ala
                565                 570                 575

Gly Ala Gly Ser Gly Ala Gly Ala Gly Ser Gly Val Gly Val Pro Gly
                580                 585                 590

Val Gly Val Pro Gly Val Gly Val Pro Gly Val Gly Val Pro Gly Lys
                595                 600                 605

Gly Val Pro Gly Val Gly Val Pro Gly Val Gly Val Pro Gly Val Gly
                610                 615                 620

Val Pro Gly Ala Gly Ala Gly Ser Gly Ala Gly Ala Gly Ser Gly Ala
625                 630                 635                 640

Gly Ala Gly Ser Gly Val Gly Val Pro Gly Val Gly Val Pro Gly Val
                645                 650                 655

Gly Val Pro Gly Val Gly Val Pro Gly Lys Gly Val Pro Gly Val Gly
                660                 665                 670

Val Pro Gly Val Gly Val Pro Gly Val Gly Val Pro Gly Ala Gly Ala
                675                 680                 685

Gly Ser Gly Ala Gly Ala Gly Ser
    690                 695

<210> SEQ ID NO 16
<211> LENGTH: 612
<212> TYPE: PRT
<213> ORGANISM: Artificial sequence
<220> FEATURE:
<223> OTHER INFORMATION: Synthetic construct

<400> SEQUENCE: 16

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
                20                  25                  30

Gly Val Pro Gly Val Gly Val Pro Gly Val Gly Val Pro Gly Val Gly
                35                  40                  45

Val Pro Gly Val Gly Val Pro Gly Val Gly Val Pro Gly Val Gly Val
            50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Val Gly Val Pro Gly Val Gly
                100                 105                 110

Val Pro Gly Val Gly Val Pro Gly Val Gly Val Pro Gly Lys Gly Val
            115                 120                 125

Pro Gly Val Gly Val Pro Gly Val Gly Val Pro Gly Val Gly Val Pro
130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Ala Gly Ala Gly Ser Gly Ala
                180                 185                 190

Gly Ala Gly Ser Gly Ala Gly Ala Gly Ser Gly Ala Gly Ser
            195                 200                 205

Gly Val Gly Val Pro Gly Val Gly Val Pro Gly Val Gly Val Pro Gly
        210                 215                 220

Val Gly Val Pro Gly Lys Gly Val Pro Gly Val Gly Val Pro Gly Val
225                 230                 235                 240

Gly Val Pro Gly Val Gly Val Pro Gly Val Gly Val Pro Gly Val Gly
            245                 250                 255

Val Pro Gly Val Gly Val Pro Gly Val Gly Val Pro Gly Val Gly Val
        260                 265                 270

Pro Gly Val Gly Val Pro Gly Val Gly Val Pro Gly Val Gly Val Pro
    275                 280                 285

Gly Ala Gly Ala Gly Ser Gly Ala Gly Ala Gly Ser Gly Ala Gly Ala
        290                 295                 300

Gly Ser Gly Ala Gly Ala Gly Ser Gly Val Gly Val Pro Gly Val Gly
305                 310                 315                 320

Val Pro Gly Val Gly Val Pro Gly Val Gly Val Pro Gly Lys Gly Val
            325                 330                 335

Pro Gly Val Gly Val Pro Gly Val Gly Val Pro Gly Val Gly Val Pro
        340                 345                 350

Gly Val Gly Val Pro Gly Val Gly Val Pro Gly Val Gly Val Pro Gly
        355                 360                 365

Val Gly Val Pro Gly Val Gly Val Pro Gly Val Gly Val Pro Gly Val
        370                 375                 380

Gly Val Pro Gly Val Gly Val Pro Gly Ala Gly Ala Gly Ser Gly Ala
385                 390                 395                 400

Gly Ala Gly Ser Gly Ala Gly Ala Gly Ser Gly Ala Gly Ala Gly Ser
            405                 410                 415

Gly Val Gly Val Pro Gly Val Gly Val Pro Gly Val Gly Val Pro Gly
            420                 425                 430

Val Gly Val Pro Gly Lys Gly Val Pro Gly Val Gly Val Pro Gly Val
        435                 440                 445

Gly Val Pro Gly Val Gly Val Pro Gly Val Gly Val Pro Gly Val Gly
        450                 455                 460

Val Pro Gly Val Gly Val Pro Gly Val Gly Val Pro Gly Val Gly Val
465                 470                 475                 480

Pro Gly Val Gly Val Pro Gly Val Gly Val Pro Gly Val Gly Val Pro
            485                 490                 495

Gly Ala Gly Ala Gly Ser Gly Ala Gly Ala Gly Ser Gly Ala Gly Ala
            500                 505                 510

Gly Ser Gly Ala Gly Ala Gly Ser Gly Val Gly Val Pro Gly Val Gly
        515                 520                 525

Val Pro Gly Val Gly Val Pro Gly Val Gly Val Pro Gly Lys Gly Val
        530                 535                 540

Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
            565                 570                 575

Val Gly Val Pro Gly Val Gly Val Pro Gly Val Gly Val Pro Gly Val
        580                 585                 590

Gly Val Pro Gly Val Gly Val Pro Gly Ala Gly Ala Gly Ser Gly Ala
        595                 600                 605

Gly Ala Gly Ser
    610

<210> SEQ ID NO 17
<211> LENGTH: 820
<212> TYPE: PRT
<213> ORGANISM: Artificial sequence
<220> FEATURE:
<223> OTHER INFORMATION: Synthetic construct

<400> SEQUENCE: 17

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Val Gly Val Pro Gly Val Gly
            100                 105                 110

Val Pro Gly Val Gly Val Pro Gly Val Gly Val Pro Gly Lys Gly Val
        115                 120                 125

Pro Gly Val Gly Val Pro Gly Val Gly Val Pro Gly Val Gly Val Pro
    130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

Gly Val Gly Val Pro Gly Val Gly Val Pro Gly Val Gly Val Pro Gly
    210                 215                 220

Val Gly Val Pro Gly Lys Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Ala Gly Ala Gly Ser Gly Ala Gly Ala Gly Ser Gly Ala Gly Ala
    290                 295                 300

Gly Ser Gly Ala Gly Ala Gly Ser Gly Val Gly Val Pro Gly Val Gly
305                 310                 315                 320

Val Pro Gly Val Gly Val Pro Gly Val Gly Val Pro Gly Lys Gly Val
                325                 330                 335

Pro Gly Val Gly Val Pro Gly Val Gly Val Pro Gly Val Gly Val Pro
            340                 345                 350

-continued

Gly Val Gly Val Pro Gly Val Gly Val Pro Gly Val Gly Val Pro Gly
            355                 360                 365
Val Gly Val Pro Gly Val Gly Val Pro Gly Val Gly Val Pro Gly Val
        370                 375                 380
Gly Val Pro Gly Val Gly Val Pro Gly Ala Gly Ala Gly Ser Gly Ala
385                 390                 395                 400
Gly Ala Gly Ser Gly Ala Gly Ala Gly Ser Gly Ala Gly Ala Gly Ser
                405                 410                 415
Gly Val Gly Val Pro Gly Val Gly Val Pro Gly Val Gly Val Pro Gly
            420                 425                 430
Val Gly Val Pro Gly Lys Gly Val Pro Gly Val Gly Val Pro Gly Val
        435                 440                 445
Gly Val Pro Gly Val Gly Val Pro Gly Val Gly Val Pro Gly Val Gly
        450                 455                 460
Val Pro Gly Val Gly Val Pro Gly Val Gly Val Pro Gly Val Gly Val
465                 470                 475                 480
Pro Gly Val Gly Val Pro Gly Val Gly Val Pro Gly Val Gly Val Pro
            485                 490                 495
Gly Ala Gly Ala Gly Ser Gly Ala Gly Ala Gly Ser Gly Ala Gly Ala
            500                 505                 510
Gly Ser Gly Ala Gly Ala Gly Ser Gly Val Gly Val Pro Gly Val Gly
        515                 520                 525
Val Pro Gly Val Gly Val Pro Gly Val Gly Val Pro Gly Lys Gly Val
        530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
            565                 570                 575
Val Gly Val Pro Gly Val Gly Val Pro Gly Val Gly Val Pro Gly Val
        580                 585                 590
Gly Val Pro Gly Val Gly Val Pro Gly Ala Gly Ala Gly Ser Gly Ala
        595                 600                 605
Gly Ala Gly Ser Gly Ala Gly Ala Gly Ser Gly Ala Gly Ala Gly Ser
610                 615                 620
Gly Val Gly Val Pro Gly Val Gly Val Pro Gly Val Gly Val Pro Gly
625                 630                 635                 640
Val Gly Val Pro Gly Lys Gly Val Pro Gly Val Gly Val Pro Gly Val
                645                 650                 655
Gly Val Pro Gly Val Gly Val Pro Gly Val Gly Val Pro Gly Val Gly
            660                 665                 670
Val Pro Gly Val Gly Val Pro Gly Val Gly Val Pro Gly Val Gly Val
        675                 680                 685
Pro Gly Val Gly Val Pro Gly Val Gly Val Pro Gly Val Gly Val Pro
690                 695                 700
Gly Ala Gly Ala Gly Ser Gly Ala Gly Ala Gly Ser Gly Ala Gly Ala
705                 710                 715                 720
Gly Ser Gly Ala Gly Ala Gly Ser Gly Val Gly Val Pro Gly Val Gly
            725                 730                 735
Val Pro Gly Val Gly Val Pro Gly Val Gly Val Pro Gly Lys Gly Val
            740                 745                 750
Pro Gly Val Gly Val Pro Gly Val Gly Val Pro Gly Val Gly Val Pro
            755                 760                 765
Gly Val Gly Val Pro Gly Val Gly Val Pro Gly Val Gly Val Pro Gly

```
                770             775             780
Val Gly Val Pro Gly Val Gly Val Pro Gly Val Gly Val Pro Gly Val
785             790             795             800

Gly Val Pro Gly Val Gly Val Pro Gly Ala Gly Ala Gly Ser Gly Ala
            805             810             815

Gly Ala Gly Ser
            820

<210> SEQ ID NO 18
<211> LENGTH: 1028
<212> TYPE: PRT
<213> ORGANISM: Artificial sequence
<220> FEATURE:
<223> OTHER INFORMATION: Synthetic construct

<400> SEQUENCE: 18

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Val Gly Val Pro Gly Val Gly
            100                 105                 110

Val Pro Gly Val Gly Val Pro Gly Val Gly Val Pro Gly Lys Gly Val
            115                 120                 125

Pro Gly Val Gly Val Pro Gly Val Gly Val Pro Gly Val Gly Val Pro
        130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
            165                 170                 175

Gly Val Pro Gly Val Gly Val Pro Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

Gly Val Gly Val Pro Gly Val Gly Val Pro Gly Val Gly Val Pro Gly
            210                 215                 220

Val Gly Val Pro Gly Lys Gly Val Pro Gly Val Gly Val Pro Gly Val
225                 230                 235                 240

Gly Val Pro Gly Val Gly Val Pro Gly Val Gly Val Pro Gly Val Gly
            245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Ala Gly Ala Gly Ser Gly Ala Gly Ala Gly Ser Gly Ala Gly Ala
        290                 295                 300

Gly Ser Gly Ala Gly Ala Gly Ser Gly Val Gly Val Pro Gly Val Gly
```

```
            305                 310                 315                 320
Val Pro Gly Val Gly Val Pro Gly Val Gly Val Pro Gly Lys Gly Val
                325                 330                 335
Pro Gly Val Gly Val Pro Gly Val Gly Val Pro Gly Val Gly Val Pro
                340                 345                 350
Gly Val Gly Val Pro Gly Val Gly Val Pro Gly Val Gly Val Pro Gly
                355                 360                 365
Val Gly Val Pro Gly Val Gly Val Pro Gly Val Gly Val Pro Gly Val
            370                 375                 380
Gly Val Pro Gly Val Gly Val Pro Gly Ala Gly Ala Gly Ser Gly Ala
385                 390                 395                 400
Gly Ala Gly Ser Gly Ala Gly Ala Gly Ser Gly Ala Gly Ala Gly Ser
                405                 410                 415
Gly Val Gly Val Pro Gly Val Gly Val Pro Gly Val Gly Val Pro Gly
                420                 425                 430
Val Gly Val Pro Gly Lys Gly Val Pro Gly Val Gly Val Pro Gly Val
                435                 440                 445
Gly Val Pro Gly Val Gly Val Pro Gly Val Gly Val Pro Gly Val Gly
            450                 455                 460
Val Pro Gly Val Gly Val Pro Gly Val Gly Val Pro Gly Val Gly Val
465                 470                 475                 480
Pro Gly Val Gly Val Pro Gly Val Gly Val Pro Gly Val Gly Val Pro
                485                 490                 495
Gly Ala Gly Ala Gly Ser Gly Ala Gly Ala Gly Ser Gly Ala Gly Ala
                500                 505                 510
Gly Ser Gly Ala Gly Ala Gly Ser Gly Val Gly Val Pro Gly Val Gly
                515                 520                 525
Val Pro Gly Val Gly Val Pro Gly Val Gly Val Pro Gly Lys Gly Val
            530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Val Gly Val Pro Gly Val
                580                 585                 590
Gly Val Pro Gly Val Gly Val Pro Gly Ala Gly Ala Gly Ser Gly Ala
                595                 600                 605
Gly Ala Gly Ser Gly Ala Gly Ala Gly Ser Gly Ala Gly Ala Gly Ser
            610                 615                 620
Gly Val Gly Val Pro Gly Val Gly Val Pro Gly Val Gly Val Pro Gly
625                 630                 635                 640
Val Gly Val Pro Gly Lys Gly Val Pro Gly Val Gly Val Pro Gly Val
                645                 650                 655
Gly Val Pro Gly Val Gly Val Pro Gly Val Gly Val Pro Gly Val Gly
                660                 665                 670
Val Pro Gly Val Gly Val Pro Gly Val Gly Val Pro Gly Val Gly Val
                675                 680                 685
Pro Gly Val Gly Val Pro Gly Val Gly Val Pro Gly Val Gly Val Pro
            690                 695                 700
Gly Ala Gly Ala Gly Ser Gly Ala Gly Ala Gly Ser Gly Ala Gly Ala
705                 710                 715                 720
Gly Ser Gly Ala Gly Ala Gly Ser Gly Val Gly Val Pro Gly Val Gly
                725                 730                 735
```

```
Val Pro Gly Val Gly Val Pro Gly Val Gly Val Pro Gly Lys Gly Val
                740                 745                 750

Pro Gly Val Gly Val Pro Gly Val Gly Val Pro Gly Val Gly Val Pro
                755                 760                 765

Gly Val Gly Val Pro Gly Val Gly Val Pro Gly Val Gly Val Pro Gly
            770                 775                 780

Val Gly Val Pro Gly Val Gly Val Pro Gly Val Gly Val Pro Gly Val
785                 790                 795                 800

Gly Val Pro Gly Val Gly Val Pro Gly Ala Gly Ala Gly Ser Gly Ala
                805                 810                 815

Gly Ala Gly Ser Gly Ala Gly Ala Gly Ser Gly Ala Gly Ala Gly Ser
            820                 825                 830

Gly Val Gly Val Pro Gly Val Gly Val Pro Gly Val Gly Val Pro Gly
            835                 840                 845

Val Gly Val Pro Gly Lys Gly Val Pro Gly Val Gly Val Pro Gly Val
        850                 855                 860

Gly Val Pro Gly Val Gly Val Pro Gly Val Gly Val Pro Gly Val Gly
865                 870                 875                 880

Val Pro Gly Val Gly Val Pro Gly Val Gly Val Pro Gly Val Gly Val
                885                 890                 895

Pro Gly Val Gly Val Pro Gly Val Gly Val Pro Gly Val Gly Val Pro
            900                 905                 910

Gly Ala Gly Ala Gly Ser Gly Ala Gly Ala Gly Ser Gly Ala Gly Ala
        915                 920                 925

Gly Ser Gly Ala Gly Ala Gly Ser Gly Val Gly Val Pro Gly Val Gly
        930                 935                 940

Val Pro Gly Val Gly Val Pro Gly Val Gly Val Pro Gly Lys Gly Val
945                 950                 955                 960

Pro Gly Val Gly Val Pro Gly Val Gly Val Pro Gly Val Gly Val Pro
                965                 970                 975

Gly Val Gly Val Pro Gly Val Gly Val Pro Gly Val Gly Val Pro Gly
            980                 985                 990

Val Gly Val Pro Gly Val Gly Val  Pro Gly Val Gly Val  Pro Gly Val
            995                 1000                1005

Gly Val  Pro Gly Val Gly Val  Pro Gly Ala Gly Ala  Gly Ser Gly
    1010                1015                1020

Ala Gly  Ala Gly Ser
1025

<210> SEQ ID NO 19
<211> LENGTH: 768
<212> TYPE: PRT
<213> ORGANISM: Artificial sequence
<220> FEATURE:
<223> OTHER INFORMATION: Synthetic construct

<400> SEQUENCE: 19

Gly Ala Gly Ser Gly Ala Gly Ala Gly Ser Gly Ala Gly Ala Gly Ser
1               5                   10                  15

Gly Val Gly Val Pro Gly Val Gly Val Pro Gly Val Gly Val Pro Gly
            20                  25                  30

Val Gly Val Pro Gly Lys Gly Val Pro Gly Val Gly Val Pro Gly Val
        35                  40                  45

Gly Val Pro Gly Val Gly Val Pro Gly Val Gly Val Pro Gly Val Gly
    50                  55                  60
```

-continued

```
Val Pro Gly Val Gly Val Pro Gly Val Gly Val Pro Gly Val Gly Val
 65                  70                  75                  80

Pro Gly Val Gly Val Pro Gly Val Gly Val Pro Gly Val Gly Val Pro
                 85                  90                  95

Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Ala Gly Ala Gly Ser Gly Ala Gly Ala Gly Ser
    130                 135                 140

Gly Val Gly Val Pro Gly Val Gly Val Pro Gly Val Gly Val Pro Gly
145                 150                 155                 160

Val Gly Val Pro Gly Lys Gly Val Pro Gly Val Gly Val Pro Gly Val
                165                 170                 175

Gly Val Pro Gly Val Gly Val Pro Gly Val Gly Val Pro Gly Val Gly
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Ala Gly Ala Gly Ser Gly Ala Gly Ala Gly Ser Gly Ala Gly Ala
225                 230                 235                 240

Gly Ser Gly Ala Gly Ala Gly Ser Gly Ala Gly Ala Gly Ser Gly Ala
                245                 250                 255

Gly Ala Gly Ser Gly Ala Gly Ala Gly Ser Gly Ala Gly Ala Gly Ser
            260                 265                 270

Gly Val Gly Val Pro Gly Val Gly Val Pro Gly Val Gly Val Pro Gly
        275                 280                 285

Val Gly Val Pro Gly Lys Gly Val Pro Gly Val Gly Val Pro Gly Val
    290                 295                 300

Gly Val Pro Gly Val Gly Val Pro Gly Val Gly Val Pro Gly Val Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Ala Gly Ala Gly Ser Gly Ala Gly Ala Gly Ser Gly Ala Gly Ala
        355                 360                 365

Gly Ser Gly Ala Gly Ala Gly Ser Gly Ala Gly Ala Gly Ser Gly Ala
    370                 375                 380

Gly Ala Gly Ser Gly Ala Gly Ala Gly Ser Gly Ala Gly Ala Gly Ser
385                 390                 395                 400

Gly Val Gly Val Pro Gly Val Gly Val Pro Gly Val Gly Val Pro Gly
                405                 410                 415

Val Gly Val Pro Gly Lys Gly Val Pro Gly Val Gly Val Pro Gly Val
            420                 425                 430

Gly Val Pro Gly Val Gly Val Pro Gly Val Gly Val Pro Gly Val Gly
        435                 440                 445

Val Pro Gly Val Gly Val Pro Gly Val Gly Val Pro Gly Val Gly Val
    450                 455                 460

Pro Gly Val Gly Val Pro Gly Val Gly Val Pro Gly Val Gly Val Pro
465                 470                 475                 480
```

Gly Ala Gly Ala Gly Ser Gly Ala Gly Ala Gly Ser Gly Ala
            485                 490                 495

Gly Ser Gly Ala Gly Ala Gly Ser Gly Ala Gly Ala Gly Ser Gly Ala
        500                 505                 510

Gly Ala Gly Ser Gly Ala Gly Ala Gly Ser Gly Ala Gly Ala Gly Ser
        515                 520                 525

Gly Val Gly Val Pro Gly Val Gly Val Pro Gly Val Gly Val Pro Gly
        530                 535                 540

Val Gly Val Pro Gly Lys Gly Val Pro Gly Val Gly Val Pro Gly Val
545                 550                 555                 560

Gly Val Pro Gly Val Gly Val Pro Gly Val Gly Val Pro Gly Val Gly
            565                 570                 575

Val Pro Gly Val Gly Val Pro Gly Val Gly Val Pro Gly Val Gly Val
            580                 585                 590

Pro Gly Val Gly Val Pro Gly Val Gly Val Pro Gly Val Gly Val Pro
            595                 600                 605

Gly Ala Gly Ala Gly Ser Gly Ala Gly Ala Gly Ser Gly Ala Gly Ala
            610                 615                 620

Gly Ser Gly Ala Gly Ala Gly Ser Gly Ala Gly Ala Gly Ser Gly Ala
625                 630                 635                 640

Gly Ala Gly Ser Gly Ala Gly Ala Gly Ser Gly Ala Gly Ala Gly Ser
            645                 650                 655

Gly Val Gly Val Pro Gly Val Gly Val Pro Gly Val Gly Val Pro Gly
            660                 665                 670

Val Gly Val Pro Gly Lys Gly Val Pro Gly Val Gly Val Pro Gly Val
            675                 680                 685

Gly Val Pro Gly Val Gly Val Pro Gly Val Gly Val Pro Gly Val Gly
            690                 695                 700

Val Pro Gly Val Gly Val Pro Gly Val Gly Val Pro Gly Val Gly Val
705                 710                 715                 720

Pro Gly Val Gly Val Pro Gly Val Gly Val Pro Gly Val Gly Val Pro
            725                 730                 735

Gly Ala Gly Ala Gly Ser Gly Ala Gly Ala Gly Ser Gly Ala Gly Ala
            740                 745                 750

Gly Ser Gly Ala Gly Ala Gly Ser Gly Ala Gly Ala Gly Ser Gly Ala
        755                 760                 765

<210> SEQ ID NO 20
<211> LENGTH: 882
<212> TYPE: PRT
<213> ORGANISM: Artificial sequence
<220> FEATURE:
<223> OTHER INFORMATION: Synthetic construct

<400> SEQUENCE: 20

Gly Ala Gly Ala Gly Ser Gly Ala Gly Ala Gly Ser Gly Val Gly Val
1               5                   10                  15

Pro Leu Gly Pro Leu Gly Pro Gly Val Gly Val Pro Gly Val Gly Val
            20                  25                  30

Pro Gly Val Gly Val Pro Gly Lys Gly Val Pro Gly Val Gly Val Pro
        35                  40                  45

Gly Val Gly Val Pro Gly Val Gly Val Pro Gly Ala Gly Ala Gly Ser
    50                  55                  60

Gly Ala Gly Ala Gly Ser Gly Val Gly Val Pro Leu Gly Pro Leu Gly
65                  70                  75                  80

-continued

```
Pro Gly Val Gly Val Pro Gly Val Gly Val Pro Gly Val Gly Val Pro
                 85                  90                  95
Gly Lys Gly Val Pro Gly Val Gly Val Pro Gly Val Gly Val Pro Gly
        100                 105                 110
Val Gly Val Pro Gly Ala Gly Ala Gly Ser Gly Ala Gly Ala Gly Ser
            115                 120                 125
Gly Val Gly Val Pro Leu Gly Pro Leu Gly Pro Gly Val Gly Val Pro
        130                 135                 140
Gly Val Gly Val Pro Gly Val Gly Val Pro Gly Lys Gly Val Pro Gly
145                 150                 155                 160
Val Gly Val Pro Gly Val Gly Val Pro Gly Val Gly Val Pro Gly Ala
            165                 170                 175
Gly Ala Gly Ser Gly Ala Gly Ala Gly Ser Gly Val Gly Val Pro Leu
        180                 185                 190
Gly Pro Leu Gly Pro Gly Val Gly Val Pro Gly Val Gly Val Pro Gly
        195                 200                 205
Val Gly Val Pro Gly Lys Gly Val Pro Gly Val Gly Val Pro Gly Val
        210                 215                 220
Gly Val Pro Gly Val Gly Val Pro Gly Ala Gly Ala Gly Ser Gly Ala
225                 230                 235                 240
Gly Ala Gly Ser Gly Val Gly Val Pro Leu Gly Pro Leu Gly Pro Gly
            245                 250                 255
Val Gly Val Pro Gly Val Gly Val Pro Gly Val Gly Val Pro Gly Lys
            260                 265                 270
Gly Val Pro Gly Val Gly Val Pro Gly Val Gly Val Pro Gly Val Gly
        275                 280                 285
Val Pro Gly Ala Gly Ala Gly Ser Gly Ala Gly Ala Gly Ser Gly Val
290                 295                 300
Gly Val Pro Leu Gly Pro Leu Gly Pro Gly Val Gly Val Pro Gly Val
305                 310                 315                 320
Gly Val Pro Gly Val Gly Val Pro Gly Lys Gly Val Pro Gly Val Gly
            325                 330                 335
Val Pro Gly Val Gly Val Pro Gly Val Gly Val Pro Gly Ala Gly Ala
        340                 345                 350
Gly Ser Gly Ala Gly Ala Gly Ser Gly Val Gly Val Pro Leu Gly Pro
        355                 360                 365
Leu Gly Pro Gly Val Gly Val Pro Gly Val Gly Val Pro Gly Val Gly
        370                 375                 380
Val Pro Gly Lys Gly Val Pro Gly Val Gly Val Pro Gly Val Gly Val
385                 390                 395                 400
Pro Gly Val Gly Val Pro Gly Ala Gly Ala Gly Ser Gly Ala Gly Ala
            405                 410                 415
Gly Ser Gly Val Gly Val Pro Leu Gly Pro Leu Gly Pro Gly Val Gly
        420                 425                 430
Val Pro Gly Val Gly Val Pro Gly Val Gly Val Pro Gly Lys Gly Val
        435                 440                 445
Pro Gly Val Gly Val Pro Gly Val Gly Val Pro Gly Val Gly Val Pro
        450                 455                 460
Gly Ala Gly Ala Gly Ser Gly Ala Gly Ala Gly Ser Gly Val Gly Val
465                 470                 475                 480
Pro Leu Gly Pro Leu Gly Pro Gly Val Gly Val Pro Gly Val Gly Val
            485                 490                 495
Pro Gly Val Gly Val Pro Gly Lys Gly Val Pro Gly Val Gly Val Pro
```

```
                500             505             510
Gly Val Gly Val Pro Gly Val Gly Val Pro Gly Ala Gly Ala Gly Ser
            515                 520                 525
Gly Ala Gly Ala Gly Ser Gly Val Gly Val Pro Leu Gly Pro Leu Gly
        530                 535                 540
Pro Gly Val Gly Val Pro Gly Val Gly Val Pro Gly Val Gly Val Pro
545                 550                 555                 560
Gly Lys Gly Val Pro Gly Val Gly Val Pro Gly Val Gly Val Pro Gly
            565                 570                 575
Val Gly Val Pro Gly Ala Gly Ala Gly Ser Gly Ala Gly Ala Gly Ser
            580                 585                 590
Gly Val Gly Val Pro Leu Gly Pro Leu Gly Pro Gly Val Gly Val Pro
            595                 600                 605
Gly Val Gly Val Pro Gly Val Gly Val Pro Gly Lys Gly Val Pro Gly
            610                 615                 620
Val Gly Val Pro Gly Val Gly Val Pro Gly Val Gly Val Pro Gly Ala
625                 630                 635                 640
Gly Ala Gly Ser Gly Ala Gly Ala Gly Ser Gly Val Gly Val Pro Leu
            645                 650                 655
Gly Pro Leu Gly Pro Gly Val Gly Val Pro Gly Val Gly Val Pro Gly
            660                 665                 670
Val Gly Val Pro Gly Lys Gly Val Pro Gly Val Gly Val Pro Gly Val
            675                 680                 685
Gly Val Pro Gly Val Gly Val Pro Gly Ala Gly Ala Gly Ser Gly Ala
            690                 695                 700
Gly Ala Gly Ser Gly Val Gly Val Pro Leu Gly Pro Leu Gly Pro Gly
705                 710                 715                 720
Val Gly Val Pro Gly Val Gly Val Pro Gly Val Gly Val Pro Gly Lys
            725                 730                 735
Gly Val Pro Gly Val Gly Val Pro Gly Val Gly Val Pro Gly Val Gly
            740                 745                 750
Val Pro Gly Ala Gly Ala Gly Ser Gly Ala Gly Ala Gly Ser Gly Val
            755                 760                 765
Gly Val Pro Leu Gly Pro Leu Gly Pro Gly Val Gly Val Pro Gly Val
            770                 775                 780
Gly Val Pro Gly Val Gly Val Pro Gly Lys Gly Val Pro Gly Val Gly
785                 790                 795                 800
Val Pro Gly Val Gly Val Pro Gly Val Gly Val Pro Gly Ala Gly Ala
            805                 810                 815
Gly Ser Gly Ala Gly Ala Gly Ser Gly Val Gly Val Pro Leu Gly Pro
            820                 825                 830
Leu Gly Pro Gly Val Gly Val Pro Gly Val Gly Val Pro Gly Val Gly
            835                 840                 845
Val Pro Gly Lys Gly Val Pro Gly Val Gly Val Pro Gly Val Gly Val
            850                 855                 860
Pro Gly Val Gly Val Pro Gly Ala Gly Ala Gly Ser Gly Ala Gly Ala
865                 870                 875                 880
Gly Ser

<210> SEQ ID NO 21
<211> LENGTH: 912
<212> TYPE: PRT
<213> ORGANISM: Artificial sequence
<220> FEATURE:
```

<223> OTHER INFORMATION: Synthetic construct

<400> SEQUENCE: 21

```
Gly Ala Gly Ala Gly Ser Gly Ala Gly Ala Gly Ser Gly Val Gly Val
1               5                   10                  15
Pro Gly Phe Phe Val Arg Ala Arg Arg Gly Val Gly Val Pro Gly Val
            20                  25                  30
Gly Val Pro Gly Val Gly Val Pro Gly Lys Gly Val Pro Gly Val Gly
        35                  40                  45
Val Pro Gly Val Gly Val Pro Gly Val Gly Val Pro Gly Ala Gly Ala
    50                  55                  60
Gly Ser Gly Ala Gly Ala Gly Ser Gly Val Gly Val Pro Gly Phe Phe
65                  70                  75                  80
Val Arg Ala Arg Arg Gly Val Gly Val Pro Gly Val Gly Val Pro Gly
                85                  90                  95
Val Gly Val Pro Gly Lys Gly Val Pro Gly Val Gly Val Pro Gly Val
            100                 105                 110
Gly Val Pro Gly Val Gly Val Pro Gly Ala Gly Ala Gly Ser Gly Ala
        115                 120                 125
Gly Ala Gly Ser Gly Val Gly Val Pro Gly Phe Phe Val Arg Ala Arg
130                 135                 140
Arg Gly Val Gly Val Pro Gly Val Gly Val Pro Gly Val Gly Val Pro
145                 150                 155                 160
Gly Lys Gly Val Pro Gly Val Gly Val Pro Gly Val Gly Val Pro Gly
                165                 170                 175
Val Gly Val Pro Gly Ala Gly Ala Gly Ser Gly Ala Gly Ala Gly Ser
            180                 185                 190
Gly Val Gly Val Pro Gly Phe Phe Val Arg Ala Arg Arg Gly Val Gly
        195                 200                 205
Val Pro Gly Val Gly Val Pro Gly Val Gly Val Pro Gly Lys Gly Val
    210                 215                 220
Pro Gly Val Gly Val Pro Gly Val Gly Val Pro Gly Val Gly Val Pro
225                 230                 235                 240
Gly Ala Gly Ala Gly Ser Gly Ala Gly Ala Gly Ser Gly Val Gly Val
                245                 250                 255
Pro Gly Phe Phe Val Arg Ala Arg Arg Gly Val Gly Val Pro Gly Val
            260                 265                 270
Gly Val Pro Gly Val Gly Val Pro Gly Lys Gly Val Pro Gly Val Gly
        275                 280                 285
Val Pro Gly Val Gly Val Pro Gly Val Gly Val Pro Gly Ala Gly Ala
    290                 295                 300
Gly Ser Gly Ala Gly Ala Gly Ser Gly Val Gly Val Pro Gly Phe Phe
305                 310                 315                 320
Val Arg Ala Arg Arg Gly Val Gly Val Pro Gly Val Gly Val Pro Gly
                325                 330                 335
Val Gly Val Pro Gly Lys Gly Val Pro Gly Val Gly Val Pro Gly Val
            340                 345                 350
Gly Val Pro Gly Val Gly Val Pro Gly Ala Gly Ala Gly Ser Gly Ala
        355                 360                 365
Gly Ala Gly Ser Gly Val Gly Val Pro Gly Phe Phe Val Arg Ala Arg
370                 375                 380
Arg Gly Val Gly Val Pro Gly Val Gly Val Pro Gly Val Gly Val Pro
385                 390                 395                 400
```

-continued

```
Gly Lys Gly Val Pro Gly Val Gly Val Pro Gly Val Gly Val Pro Gly
            405                 410                 415
Val Gly Val Pro Gly Ala Gly Ala Gly Ser Gly Ala Gly Ala Gly Ser
            420                 425                 430
Gly Val Gly Val Pro Gly Phe Phe Val Arg Ala Arg Arg Gly Val Gly
            435                 440                 445
Val Pro Gly Val Gly Val Pro Gly Val Gly Val Pro Gly Lys Gly Val
            450                 455                 460
Pro Gly Val Gly Val Pro Gly Val Gly Val Pro Gly Val Gly Val Pro
465                 470                 475                 480
Gly Ala Gly Ala Gly Ser Gly Ala Gly Ala Gly Ser Gly Val Gly Val
            485                 490                 495
Pro Gly Phe Phe Val Arg Ala Arg Arg Gly Val Gly Val Pro Gly Val
            500                 505                 510
Gly Val Pro Gly Val Gly Val Pro Gly Lys Gly Val Pro Gly Val Gly
            515                 520                 525
Val Pro Gly Val Gly Val Pro Gly Val Gly Val Pro Gly Ala Gly Ala
            530                 535                 540
Gly Ser Gly Ala Gly Ala Gly Ser Gly Val Gly Val Pro Gly Phe Phe
545                 550                 555                 560
Val Arg Ala Arg Arg Gly Val Gly Val Pro Gly Val Gly Val Pro Gly
            565                 570                 575
Val Gly Val Pro Gly Lys Gly Val Pro Gly Val Gly Val Pro Gly Val
            580                 585                 590
Gly Val Pro Gly Val Gly Val Pro Gly Ala Gly Ala Gly Ser Gly Ala
            595                 600                 605
Gly Ala Gly Ser Gly Val Gly Val Pro Gly Phe Phe Val Arg Ala Arg
            610                 615                 620
Arg Gly Val Gly Val Pro Gly Val Gly Val Pro Gly Val Gly Val Pro
625                 630                 635                 640
Gly Lys Gly Val Pro Gly Val Gly Val Pro Gly Val Gly Val Pro Gly
            645                 650                 655
Val Gly Val Pro Gly Ala Gly Ala Gly Ser Gly Ala Gly Ala Gly Ser
            660                 665                 670
Gly Val Gly Val Pro Gly Phe Phe Val Arg Ala Arg Arg Gly Val Gly
            675                 680                 685
Val Pro Gly Val Gly Val Pro Gly Val Gly Val Pro Gly Lys Gly Val
            690                 695                 700
Pro Gly Val Gly Val Pro Gly Val Gly Val Pro Gly Val Gly Val Pro
705                 710                 715                 720
Gly Ala Gly Ala Gly Ser Gly Ala Gly Ala Gly Ser Gly Val Gly Val
            725                 730                 735
Pro Gly Phe Phe Val Arg Ala Arg Arg Gly Val Gly Val Pro Gly Val
            740                 745                 750
Gly Val Pro Gly Val Gly Val Pro Gly Lys Gly Val Pro Gly Val Gly
            755                 760                 765
Val Pro Gly Val Gly Val Pro Gly Val Gly Val Pro Gly Ala Gly Ala
            770                 775                 780
Gly Ser Gly Ala Gly Ala Gly Ser Gly Val Gly Val Pro Gly Phe Phe
785                 790                 795                 800
Val Arg Ala Arg Arg Gly Val Gly Val Pro Gly Val Gly Val Pro Gly
            805                 810                 815
Val Gly Val Pro Gly Lys Gly Val Pro Gly Val Gly Val Pro Gly Val
```

```
                    820                 825                 830
Gly Val Pro Gly Val Gly Val Pro Gly Ala Gly Ala Gly Ser Gly Ala
                835                 840                 845

Gly Ala Gly Ser Gly Val Gly Val Pro Gly Phe Phe Val Arg Ala Arg
            850                 855                 860

Arg Gly Val Gly Val Pro Gly Val Gly Val Pro Gly Val Gly Val Pro
865                 870                 875                 880

Gly Lys Gly Val Pro Gly Val Gly Val Pro Gly Val Gly Val Pro Gly
                885                 890                 895

Val Gly Val Pro Gly Ala Gly Ala Gly Ser Gly Ala Gly Ala Gly Ser
            900                 905                 910

<210> SEQ ID NO 22
<211> LENGTH: 820
<212> TYPE: PRT
<213> ORGANISM: Artificial sequence
<220> FEATURE:
<223> OTHER INFORMATION: Synthetic construct

<400> SEQUENCE: 22

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Val Gly Val Pro Gly Val Gly Val Pro Gly Val Gly Val Pro
    50                  55                  60

Gly Val Gly Val Pro Gly Lys Gly Val Pro Gly Val Gly Val Pro Gly
65                  70                  75                  80

Val Gly Val Pro Gly Val Gly Val Pro Gly Val Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
        115                 120                 125

Pro Gly Ala Gly Ala Gly Ser Gly Ala Gly Ala Gly Ser Gly Ala Gly
    130                 135                 140

Ala Gly Ser Gly Ala Gly Ala Gly Ser Gly Ala Gly Ala Gly Ser Gly
145                 150                 155                 160

Ala Gly Ala Gly Ser Gly Ala Gly Ala Gly Ser Gly Ala Gly Ala Gly
                165                 170                 175

Ser Gly Val Gly Val Pro Gly Val Gly Val Pro Gly Val Gly Val Pro
            180                 185                 190

Gly Val Gly Val Pro Gly Lys Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Val Gly Val
                245                 250                 255

Pro Gly Ala Gly Ala Gly Ser Gly Ala Gly Ala Gly Ser Gly Ala Gly
            260                 265                 270

Ala Gly Ser Gly Ala Gly Ala Gly Ser Gly Ala Gly Ala Gly Ser Gly
```

```
                275                 280                 285
Ala Gly Ala Gly Ser Gly Ala Gly Ala Gly Ser Gly Ala Gly
    290                 295                 300
Ser Gly Val Gly Val Pro Gly Val Gly Val Pro Gly Val Gly Val Pro
305                 310                 315                 320
Gly Val Gly Val Pro Gly Lys Gly Val Pro Gly Val Gly Val Pro Gly
                325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
                355                 360                 365
Val Pro Gly Val Gly Val Pro Gly Val Gly Val Pro Gly Val Gly Val
        370                 375                 380
Pro Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
                405                 410                 415
Ala Gly Ala Gly Ser Gly Ala Gly Ala Gly Ser Gly Ala Gly Ala Gly
            420                 425                 430
Ser Gly Val Gly Val Pro Gly Val Gly Val Pro Gly Val Gly Val Pro
            435                 440                 445
Gly Val Gly Val Pro Gly Lys Gly Val Pro Gly Val Gly Val Pro Gly
    450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
                485                 490                 495
Val Pro Gly Val Gly Val Pro Gly Val Gly Val Pro Gly Val Gly Val
        500                 505                 510
Pro Gly Ala Gly Ala Gly Ser Gly Ala Gly Ala Gly Ser Gly Ala Gly
        515                 520                 525
Ala Gly Ser Gly Ala Gly Ala Gly Ser Gly Ala Gly Ala Gly Ser Gly
    530                 535                 540
Ala Gly Ala Gly Ser Gly Ala Gly Ala Gly Ser Gly Ala Gly Ala Gly
545                 550                 555                 560
Ser Gly Val Gly Val Pro Gly Val Gly Val Pro Gly Val Gly Val Pro
                565                 570                 575
Gly Val Gly Val Pro Gly Lys Gly Val Pro Gly Val Gly Val Pro Gly
                580                 585                 590
Val Gly Val Pro Gly Val Gly Val Pro Gly Val Gly Val Pro Gly Val
            595                 600                 605
Gly Val Pro Gly Val Gly Val Pro Gly Val Gly Val Pro Gly Val Gly
            610                 615                 620
Val Pro Gly Val Gly Val Pro Gly Val Gly Val Pro Gly Val Gly Val
625                 630                 635                 640
Pro Gly Ala Gly Ala Gly Ser Gly Ala Gly Ala Gly Ser Gly Ala Gly
                645                 650                 655
Ala Gly Ser Gly Ala Gly Ala Gly Ser Gly Ala Gly Ala Gly Ser Gly
            660                 665                 670
Ala Gly Ala Gly Ser Gly Ala Gly Ala Gly Ser Gly Ala Gly Ala Gly
                675                 680                 685
Ser Gly Val Gly Val Pro Gly Val Gly Val Pro Gly Val Gly Val Pro
    690                 695                 700
```

```
Gly Val Gly Val Pro Gly Lys Gly Val Pro Gly Val Gly Val Pro Gly
705                 710                 715                 720

Val Gly Val Pro Gly Val Gly Val Pro Gly Val Gly Val Pro Gly Val
                725                 730                 735

Gly Val Pro Gly Val Gly Val Pro Gly Val Gly Val Pro Gly Val Gly
            740                 745                 750

Val Pro Gly Val Gly Val Pro Gly Val Gly Val Pro Gly Val Gly Val
        755                 760                 765

Pro Gly Ala Gly Ala Gly Ser Gly Ala Gly Ala Gly Ser Gly Ala Gly
    770                 775                 780

Ala Gly Ser Gly Ala Gly Ala Gly Ser Gly Ala Gly Ala Gly Ser Gly
785                 790                 795                 800

Ala Gly Ala Met Asp Pro Gly Arg Tyr Gln Asp Leu Arg Ser His His
                805                 810                 815

His His His His
        820

<210> SEQ ID NO 23
<211> LENGTH: 882
<212> TYPE: PRT
<213> ORGANISM: Artificial sequence
<220> FEATURE:
<223> OTHER INFORMATION: Synthetic construct

<400> SEQUENCE: 23

Met Asp Pro Val Val Leu Gln Arg Arg Asp Trp Glu Asn Pro Gly Val
1               5                   10                  15

Thr Gln Leu Val Arg Leu Ala Ala His Pro Pro Phe Ala Ser Asp Pro
            20                  25                  30

Met Gly Ala Gly Ser Gly Ala Gly Ser Gly Val Gly Val Pro Gly Val
        35                  40                  45

Gly Val Pro Gly Val Gly Val Pro Gly Val Gly Val Pro Gly Lys Gly
    50                  55                  60

Val Pro Gly Val Gly Val Pro Gly Val Gly Val Pro Gly Val Gly Val
65                  70                  75                  80

Pro Gly Ala Gly Ala Gly Ser Gly Ala Gly Ala Gly Ser Gly Ala Gly
                85                  90                  95

Ala Gly Ser Gly Ala Gly Ala Gly Ser Gly Val Gly Val Pro Gly Val
            100                 105                 110

Gly Val Pro Gly Val Gly Val Pro Gly Val Gly Val Pro Gly Lys Gly
        115                 120                 125

Val Pro Gly Val Gly Val Pro Gly Val Gly Val Pro Gly Val Gly Val
    130                 135                 140

Pro Gly Ala Gly Ala Gly Ser Gly Ala Gly Ala Gly Ser Gly Ala Gly
145                 150                 155                 160

Ala Gly Ser Gly Ala Gly Ala Gly Ser Gly Val Gly Val Pro Gly Val
                165                 170                 175

Gly Val Pro Gly Val Gly Val Pro Gly Val Gly Val Pro Gly Lys Gly
            180                 185                 190

Val Pro Gly Val Gly Val Pro Gly Val Gly Val Pro Gly Val Gly Val
        195                 200                 205

Pro Gly Ala Gly Ala Gly Ser Gly Ala Gly Ala Gly Ser Gly Ala Gly
    210                 215                 220

Ala Gly Ser Gly Ala Gly Ala Gly Ser Gly Val Gly Val Pro Gly Val
225                 230                 235                 240
```

-continued

```
Gly Val Pro Gly Val Gly Val Pro Gly Val Gly Pro Lys Gly
                245                 250                 255
Val Pro Gly Val Gly Val Pro Gly Val Gly Val Pro Gly Val Gly Val
            260                 265                 270
Pro Gly Ala Gly Ala Gly Ser Gly Ala Gly Ala Gly Ser Gly Ala Gly
        275                 280                 285
Ala Gly Ser Gly Ala Gly Ala Gly Ser Gly Val Gly Val Pro Gly Val
    290                 295                 300
Gly Val Pro Gly Val Gly Val Pro Gly Val Gly Val Pro Gly Lys Gly
305                 310                 315                 320
Val Pro Gly Val Gly Val Pro Gly Val Gly Val Pro Gly Val Gly Val
            325                 330                 335
Pro Gly Ala Gly Ala Gly Ser Gly Ala Gly Ala Gly Ser Gly Ala Gly
        340                 345                 350
Ala Gly Ser Gly Ala Gly Ala Gly Ser Gly Val Gly Val Pro Gly Val
    355                 360                 365
Gly Val Pro Gly Val Gly Val Pro Gly Val Gly Val Pro Gly Lys Gly
        370                 375                 380
Val Pro Gly Val Gly Val Pro Gly Val Gly Val Pro Gly Val Gly Val
385                 390                 395                 400
Pro Gly Ala Gly Ala Gly Ser Gly Ala Gly Ala Gly Ser Gly Ala Gly
            405                 410                 415
Ala Gly Ser Gly Ala Gly Ala Gly Ser Gly Val Gly Val Pro Gly Val
        420                 425                 430
Gly Val Pro Gly Val Gly Val Pro Gly Val Gly Val Pro Gly Lys Gly
    435                 440                 445
Val Pro Gly Val Gly Val Pro Gly Val Gly Val Pro Gly Val Gly Val
            450                 455                 460
Pro Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
            485                 490                 495
Gly Val Pro Gly Val Gly Val Pro Gly Val Gly Val Pro Gly Lys Gly
        500                 505                 510
Val Pro Gly Val Gly Val Pro Gly Val Gly Val Pro Gly Val Gly Val
    515                 520                 525
Pro Gly Ala Gly Ala Gly Ser Gly Ala Gly Ala Gly Ser Gly Ala Gly
        530                 535                 540
Ala Gly Ser Gly Ala Gly Ala Gly Ser Gly Val Gly Val Pro Gly Val
545                 550                 555                 560
Gly Val Pro Gly Val Gly Val Pro Gly Val Gly Val Pro Gly Lys Gly
            565                 570                 575
Val Pro Gly Val Gly Val Pro Gly Val Gly Val Pro Gly Val Gly Val
        580                 585                 590
Pro Gly Ala Gly Ala Gly Ser Gly Ala Gly Ala Gly Ser Gly Ala Gly
    595                 600                 605
Ala Gly Ser Gly Ala Gly Ala Gly Ser Gly Val Gly Val Pro Gly Val
        610                 615                 620
Gly Val Pro Gly Val Gly Val Pro Gly Val Gly Val Pro Gly Lys Gly
625                 630                 635                 640
Val Pro Gly Val Gly Val Pro Gly Val Gly Val Pro Gly Val Gly Val
            645                 650                 655
```

```
Pro Gly Ala Gly Ala Gly Ser Gly Ala Gly Ala Ser Gly Ala Gly
            660                 665                 670
Ala Gly Ser Gly Ala Gly Ala Gly Ser Gly Val Gly Val Pro Gly Val
        675                 680                 685
Gly Val Pro Gly Val Gly Val Pro Gly Val Gly Val Pro Gly Lys Gly
    690                 695                 700
Val Pro Gly Val Gly Val Pro Gly Val Gly Val Pro Gly Val Gly Val
705                 710                 715                 720
Pro Gly Ala Gly Ala Gly Ser Gly Ala Gly Ala Ser Gly Ala Gly
            725                 730                 735
Ala Gly Ser Gly Ala Gly Ala Gly Ser Gly Val Gly Val Pro Gly Val
        740                 745                 750
Gly Val Pro Gly Val Gly Val Pro Gly Val Gly Val Pro Gly Lys Gly
    755                 760                 765
Val Pro Gly Val Gly Val Pro Gly Val Gly Val Pro Gly Val Gly Val
770                 775                 780
Pro Gly Ala Gly Ala Gly Ser Gly Ala Gly Ala Ser Gly Ala Gly
785                 790                 795                 800
Ala Gly Ser Gly Ala Gly Ala Gly Ser Gly Val Gly Val Pro Gly Val
        805                 810                 815
Gly Val Pro Gly Val Gly Val Pro Gly Val Gly Val Pro Gly Lys Gly
    820                 825                 830
Val Pro Gly Val Gly Val Pro Gly Val Gly Val Pro Gly Val Gly Val
        835                 840                 845
Pro Gly Ala Gly Ala Gly Ser Gly Ala Gly Ala Ser Gly Ala Gly
850                 855                 860
Ala Met Asp Pro Gly Arg Tyr Gln Asp Leu Arg Ser His His His His
865                 870                 875                 880

His His

<210> SEQ ID NO 24
<211> LENGTH: 8
<212> TYPE: PRT
<213> ORGANISM: Artificial sequence
<220> FEATURE:
<223> OTHER INFORMATION: Synthetic construct

<400> SEQUENCE: 24

Ala Pro Gly Gln Ile Ala Gly Gln
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic construct

<400> SEQUENCE: 25

Gly Pro Gln Gly Leu Ala Gly Gln
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic construct

<400> SEQUENCE: 26
```

Gly Pro Leu Gly Ile Ala Gly Ile
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic construct

<400> SEQUENCE: 27

Ile Pro Glu Asn Phe Phe Gly Val
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic construct

<400> SEQUENCE: 28

Met Ala Ala Ser Ala Lys Arg Glu
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic construct

<400> SEQUENCE: 29

Pro Phe Ser Pro Leu Val Ala Thr
1               5

<210> SEQ ID NO 30
<211> LENGTH: 8
<212> TYPE: PRT
<213> ORGANISM: Artificial sequence
<220> FEATURE:
<223> OTHER INFORMATION: Synthetic construct

<400> SEQUENCE: 30

Gly Pro Gln Gly Ile Phe Gly Gln
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic construct

<400> SEQUENCE: 31

Arg Ala Ile His Ile Gln Ala Glu
1               5

<210> SEQ ID NO 32
<211> LENGTH: 8
<212> TYPE: PRT
<213> ORGANISM: Artificial sequence
<220> FEATURE:
<223> OTHER INFORMATION: Synthetic construct

<400> SEQUENCE: 32

-continued

Gly Pro Leu Gly Ile Ala Gly Gln
1               5

<210> SEQ ID NO 33
<211> LENGTH: 8
<212> TYPE: PRT
<213> ORGANISM: Artificial sequence
<220> FEATURE:
<223> OTHER INFORMATION: Synthetic construct

<400> SEQUENCE: 33

Gly Pro Gln Ala Ile Ala Gly Gln
1               5

<210> SEQ ID NO 34
<211> LENGTH: 810
<212> TYPE: PRT
<213> ORGANISM: Artificial sequence
<220> FEATURE:
<223> OTHER INFORMATION: Synthetic construct

<400> SEQUENCE: 34

Gly Ala Gly Ser Gly Ala Gly Ala Gly Ser Gly Ala Gly Ala Gly Ser
1               5                   10                  15

Gly Val Gly Val Pro Gly Val Gly Val Pro Gly Val Gly Val Pro Gly
                20                  25                  30

Val Gly Gly Pro Gln Gly Ile Phe Gly Gln Pro Gly Lys Gly Val Pro
            35                  40                  45

Gly Val Gly Val Pro Gly Val Gly Val Pro Gly Val Gly Val Pro Gly
        50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Ala Gly Ala Gly Ser Gly Ala Gly
                100                 105                 110

Ala Gly Ser Gly Ala Gly Ala Gly Ser Gly Ala Gly Ala Gly Ser Gly
            115                 120                 125

Ala Gly Ala Gly Ser Gly Ala Gly Ala Gly Ser Gly Ala Gly Ala Gly
        130                 135                 140

Ser Gly Ala Gly Ala Gly Ser Gly Val Gly Val Pro Gly Val Gly Val
145                 150                 155                 160

Pro Gly Val Gly Val Pro Gly Val Gly Gly Pro Gln Gly Ile Phe Gly
                165                 170                 175

Gln Pro Gly Lys Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Val Pro Gly Val Gly Val Pro Gly
    210                 215                 220

Val Gly Val Pro Gly Val Gly Val Pro Gly Val Gly Val Pro Gly Ala
225                 230                 235                 240

Gly Ala Gly Ser Gly Ala Gly Ala Gly Ser Gly Ala Gly Ala Gly Ser
                245                 250                 255

Gly Ala Gly Ala Gly Ser Gly Ala Gly Ala Gly Ser Gly Ala Gly Ala
            260                 265                 270

Gly Ser Gly Ala Gly Ala Gly Ser Gly Ala Gly Ala Gly Ser Gly Val
        275                 280                 285

```
Gly Val Pro Gly Val Gly Val Pro Gly Val Gly Val Pro Gly Val Gly
            290                 295                 300
Gly Pro Gln Gly Ile Phe Gly Gln Pro Gly Lys Gly Val Pro Gly Val
305                 310                 315                 320
Gly Val Pro Gly Val Gly Val Pro Gly Val Gly Val Pro Gly Val Gly
            325                 330                 335
Val Pro Gly Val Gly Val Pro Gly Val Gly Val Pro Gly Val Gly Val
            340                 345                 350
Pro Gly Val Gly Val Pro Gly Val Gly Val Pro Gly Val Gly Val Pro
            355                 360                 365
Gly Val Gly Val Pro Gly Ala Gly Ala Gly Ser Gly Ala Gly Ala Gly
            370                 375                 380
Ser Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
            405                 410                 415
Ala Gly Ala Gly Ser Gly Val Gly Val Pro Gly Val Gly Val Pro Gly
            420                 425                 430
Val Gly Val Pro Gly Val Gly Gly Pro Gln Gly Ile Phe Gly Gln Pro
            435                 440                 445
Gly Lys Gly Val Pro Gly Val Gly Val Pro Gly Val Gly Val Pro Gly
            450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
            485                 490                 495
Val Pro Gly Val Gly Val Pro Gly Val Gly Val Pro Gly Ala Gly Ala
            500                 505                 510
Gly Ser Gly Ala Gly Ala Gly Ser Gly Ala Gly Ala Gly Ser Gly Ala
            515                 520                 525
Gly Ala Gly Ser Gly Ala Gly Ala Gly Ser Gly Ala Gly Ala Gly Ser
            530                 535                 540
Gly Ala Gly Ala Gly Ser Gly Ala Gly Ala Gly Ser Gly Val Gly Val
545                 550                 555                 560
Pro Gly Val Gly Val Pro Gly Val Gly Val Pro Gly Val Gly Gly Pro
            565                 570                 575
Gln Gly Ile Phe Gly Gln Pro Gly Lys Gly Val Pro Gly Val Gly Val
            580                 585                 590
Pro Gly Val Gly Val Pro Gly Val Gly Val Pro Gly Val Gly Val Pro
            595                 600                 605
Gly Val Gly Val Pro Gly Val Gly Val Pro Gly Val Gly Val Pro Gly
            610                 615                 620
Val Gly Val Pro Gly Val Gly Val Pro Gly Val Gly Val Pro Gly Val
625                 630                 635                 640
Gly Val Pro Gly Ala Gly Ala Gly Ser Gly Ala Gly Ala Gly Ser Gly
            645                 650                 655
Ala Gly Ala Gly Ser Gly Ala Gly Ala Gly Ser Gly Ala Gly Ala Gly
            660                 665                 670
Ser Gly Ala Gly Ala Gly Ser Gly Ala Gly Ala Gly Ser Gly Ala Gly
            675                 680                 685
Ala Gly Ser Gly Val Gly Val Pro Gly Val Gly Val Pro Gly Val Gly
            690                 695                 700
```

```
Val Pro Gly Val Gly Gly Pro Gln Gly Ile Phe Gly Gln Pro Gly Lys
705                 710                 715                 720

Gly Val Pro Gly Val Gly Val Pro Gly Val Gly Val Pro Gly Val Gly
                725                 730                 735

Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
        755                 760                 765

Gly Val Gly Val Pro Gly Val Gly Val Pro Gly Ala Gly Ala Gly Ser
    770                 775                 780

Gly Ala Gly Ala Gly Ser Gly Ala Gly Ala Gly Ser Gly Ala Gly Ala
785                 790                 795                 800

Gly Ser Gly Ala Gly Ala Gly Ser Gly Ala
                805                 810
```

METHODS FOR PRODUCING CHEMOEMBOLIC AGENTS FOR THE DELIVERY OF ANTI-CANCER AGENTS

CROSS REFERENCE TO RELATED APPLICATIONS

This application claims priority upon U.S. provisional application Ser. No. 62/518,118 filed on Jun. 12, 2017. This application is hereby incorporated by reference in its entirety.

STATEMENT REGARDING FEDERALLY SPONSORED RESEARCH

This invention was made with government support under grant numbers CA168123, CA107621 and CA176922 awarded by the National Institutes of Health and grant number 1256065 awarded by the National Science Foundation. The government has certain rights in the invention."

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CRF), is incorporated by reference in its entirety.

BACKGROUND

The need for improved cancer therapies is becoming more evident as the number of cases refractory to standard of care treatments increases. The incidence of hepatocellular carcinoma (HCC) of the liver has nearly tripled since the early 1980s in the United States; this disease affects over half a million patients worldwide each year. Treatment is dictated by staging level and the patient's overall liver function.

Transarterial embolization (TAE) is a procedure in which a microcatheter is inserted into and guided through a peripheral artery to a target tissue for localized delivery of an embolic agent to selectively block blood flow. TAE is used to treat abnormal vasculature, such as aneurysms and arteriovenous malformations (AVMs), to control gastrointestinal bleeding, and to treat tumors of the head, neck, liver, kidney, and colon. During tumor transarterial chemoembolization (TACE), a chemotherapeutic agent is co-delivered with the embolic agent. Both TAE and TACE treatment of un-resectable tumors have repeatedly demonstrated survival benefit.

Patients with intermediate stage HCC are candidates for loco-regional therapy including TACE. TACE involves angiographic identification of the vessels feeding into the tumor followed by embolization to induce necrosis and locally deposit a high concentration of chemotherapeutic agent. The success of TACE is due to the dual blood supply of the liver. Cancerous tissue draws blood from branches of the hepatic artery, while healthy parenchyma receives over 75% of its blood supply from the portal vein. Occlusion of the hepatic artery branches preserves liver function while thwarting tumor progression. Clinically, inclusion of locally delivered chemotherapeutic agents increases the overall time to disease progression when compared to embolization alone.

Drug eluting beads (DEBs) are a widely used embolic system for localized delivery in TACE. However, the mechanism of drug incorporation limits the drugs that can be used. Leading microspheres use either an ion exchange method or a swelling process followed by interaction of the drug with ionized side chains. In both methods, only charged, low molecular weight drugs can be incorporated. Most commonly, the positively charged salt forms of doxorubicin or irinotecan have been incorporated into clinically available DEBs. A further limitation of these non-degradable DEBs is their finite size and inability to penetrate down to the arterio-capillary level of the vessels feeding into the tumor, thus decreasing penetration and reducing the total tumor volume that can be exposed to drug. DEB drug delivery relies on the concentration gradient within the spheres followed by either diffusive or matrix swelling mechanisms for non-degradable polymer matrices.

Two liquid embolic agents are currently on the market, ONYX® and PHIL™. ONYX® is composed of ethylene vinyl alcohol (EVOH) copolymer, while PHIL™ is a polymeric system where poly(lactide-co-glycolide) and poly (hydroxyl ethyl methacrylate) are both dissolved in the organic solvent dimethyl sulfoxide (DMSO). Due to the solvation in DMSO, use of these agents is associated with vascular inflammation and angionecrosis and neither can be used to deliver drugs as the dissipation of DMSO during administration would cause a burst release of the entire therapeutic payload, resulting in acute local toxicity and transient therapeutic effects. Therefore, these liquid embolics are not considered chemoembolics and are not used in TACE; they are simply used for embolic purposes.

What is needed is an embolic agent capable of penetrating down to the arterio-capillary level of vessels feeding into a tumor. Furthermore, it would be desirable if the embolic agent was a chemoembolic agent capable of localized delivery of anti-cancer agents to tumor tissue during chemoembolization. It would also be desirable to have an anti-cancer agent with reduced toxic side effects so that patients could follow the original treatment plan without delays or dose reductions, leading to improved patient outcomes. Furthermore, the anti-cancer agent would be capable of sustained, localized release of a payload of anti-cancer agent over a period of days or weeks. The present invention addresses these needs.

SUMMARY

Described herein are chemoembolic compositions and agents. The compositions include one or more anti-cancer agents and a silk-elastinlike protein polymer, wherein the compositions are liquids prior to administration to a subject but convert to hydrogels upon administration to the subject. Administration of the chemoembolic compositions to tumor and/or tumor vasculature in a subject having cancer can result in reduced or inhibited blood flow to the tumor as well as localized, sustained release of the anti-cancer agent in the vicinity of the tumor. Reduction in blood flow, in turn, results in a reduction of tumor volume and/or inhibition of tumor growth, while localized release of the anti-cancer agent results in reduced systemic effects and lower overall toxicity of treatment with the compositions.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 2A and 2B show viscosity traces of SELP incorporating the various forms of doxorubicin or sorafenib. FIG. 2C shows storage moduli, G', for the SELP hydrogels formed with and without drug incorporation at 5 minutes and 3 hours at 37° C. Data represents mean±standard deviation, N=3.

FIG. 3A is a representative scan of a gel sample with the drugs incorporated as dissolved in DMSO. Star polyhedron crystals are doxorubicin and the cubic polyhedron crystals are sorafenib, which coat the polymer matrix in a consistent layer. FIG. 3B is a representative scan of a gel sample with powdered drugs mixed into the liquid SELP. During the gelation process, the polymer indicated by the arrowhead entraps the drug clusters indicated by the arrow.

FIG. 4A shows comparison of the relative release rates of the single drug loaded gels of different incorporation methods. (*) represents a statistically significant greater release (p<0.05) for all time points less than 1 day of release of doxorubicin base dissolved in DMSO versus powder. The three squares represent statistically significant differences (p<0.001) for release of doxorubicin gels as compared to release of sorafenib. FIG. 4B shows comparison of the four sorafenib loaded gels. (*) shows statistical significance between the sorafenib dissolved in DMSO released from the dual drug loaded gel versus the single drug loaded gel. (+) shows statistical significance between the sorafenib dissolved in DMSO released from the dual drug loaded gel versus sorafenib powder released from the dual drug loaded gel. (●) shows statistical significance between the sorafenib dissolved in DMSO released from the dual drug loaded gel versus sorafenib powder released from the single drug loaded gel. (x) shows statistical significance between the sorafenib dissolved in DMSO released from the single drug loaded gel versus sorafenib powder released from both the single and the dual drug loaded gels. (−) shows statistical significance between the sorafenib powder groups. The presence of doxorubicin significantly increases the cumulative release of sorafenib. Data is represented as the mean±standard deviation, N=3.

FIG. 6A is a comparison of spectra of the amide I region for SELP gels loaded with dissolved drug in DMSO. FIG. 6B is a comparison of spectra of the amide I region for SELP gels loaded with powder drug. FIG. 6C is a representative absorbance spectrum of 9% SELP-815K with no mechanical mixing deconvolved using the Voigt peak fitting algorithm. The composite spectrum, shown in blue, appropriately fits the original curve, shown in black. The second derivative of the original scan is shown below and is used to identify peak assignments for secondary structures. FIG. 6D shows a comparison of the second derivative traces for original spectra of each gel sample at the primary beta sheet peak assignment. Upshifting of gels loaded with sorafenib dissolved in DMSO is evident. FIG. 6E is a comparison of relative percent of secondary structures present in each gel.

FIG. 7A shows viscosity curves for each experimental group. FIG. 7B shows the storage modulus, G', which is representative of the material stiffness. No significant difference was determined between groups as compared to the control in both viscosity and stiffness. Data is represented as the mean±standard deviation, N=3. Standard deviation is presented as the dotted lines above and below the solid traces in FIG. 7B.

FIG. 8A shows a comparison of the relative release rates of doxorubicin from single drug loaded gels at either 25 mg/mL or 50 mg/mL and from the dual drug loaded gel at 25 mg/mL loading per drug. (*) shows statistical significance between the doxorubicin single drug loaded versus dual drug loaded gels. (+) shows statistical significance between single drug loaded 25 mg/mL versus single drug loaded 50 mg/mL gels. (●) shows statistical significance between the dual drug loaded gels and the single drug loaded 50 mg/mL gels. The same symbolic scheme applies to the sorafenib results in FIG. 8B. Data is represented as the mean±standard deviation, N=5.

FIG. 9A is representative images of pre-release gels. Drug clusters are clearly visible dispersed throughout the loaded gels. FIG. 9B is representative images of post-release gels. The bulk drug clusters are not readily observed but thin layers of crystalline drug are visible.

DETAILED DESCRIPTION

Figure 1:
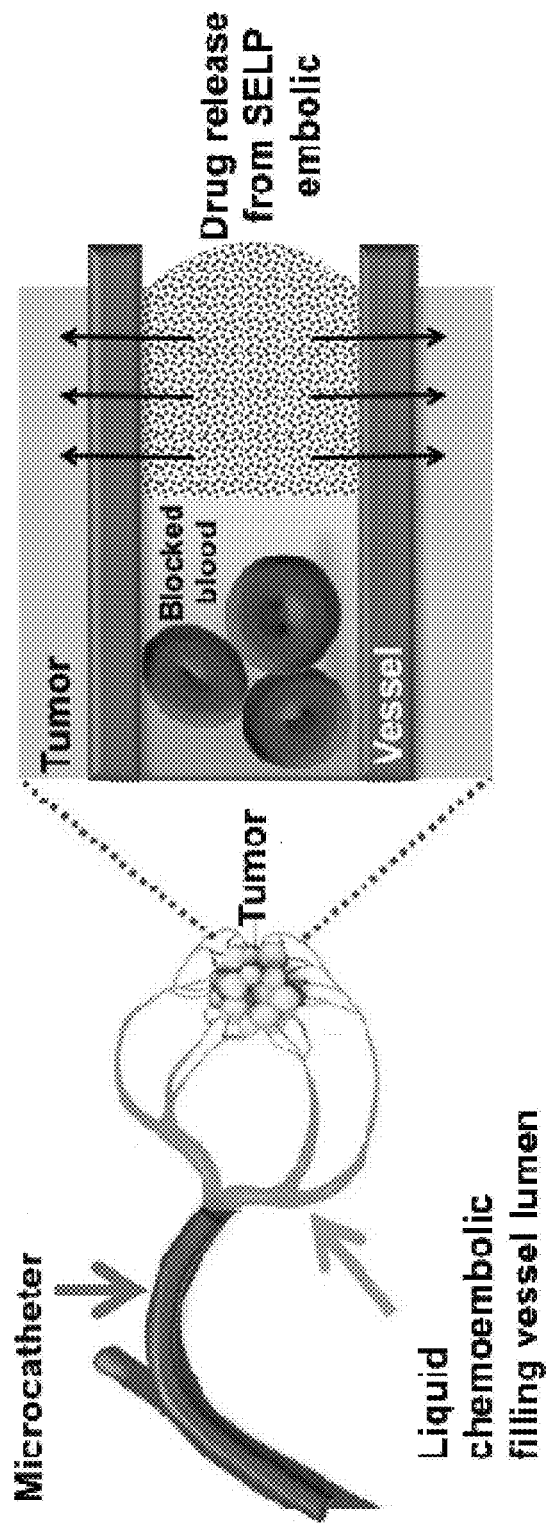
FIG. 1 is a schematic depiction of transarterial chemoembolization (TACE) using microcatheter to administer a silk-elastinlike protein polymer (SELP) to a vessel supplying blood to a tumor.

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and appended claims, the singular forms "a," "an," and "the" include plural referents unless the context clearly dictates otherwise. Thus, for example, reference to "an anti-cancer agent" includes mixtures of two or more anti-cancer agents, and the like.

"Optional" or "optionally" means that the subsequently described event or circumstance can or cannot occur, and that the description includes instances where the event or circumstance occurs and instances where it does not. For example, the pharmaceutical compositions described herein may optionally contain one or more contrast agents, where the contrast agents may or may not be present.

As used herein, the term "about" is used to provide flexibility to a numerical range endpoint by providing that a given value may be "a little above" or "a little below" the endpoint without affecting the desired result.

Throughout this specification, unless the context dictates otherwise, the word "comprise," or variations such as "comprises" or "comprising," will be understood to imply the inclusion of a stated element, integer or step, or group of elements, integers or steps, but not the exclusion of any other element, integer or step, or group of elements, integers, or steps.

A "subject" as used in the specification and concluding claims, refers to a human or non-human animal. For example, the subject can be a non-human animal (domesticated, wild, or farm) such as, for example, a horse, cat, dog, cow, pig, sheep, goat, mouse, rabbit, chicken, rat, or guinea pig.

A "hydrogel" as used in the specification and concluding claims refers to a semisolid composition constituting a substantial amount of water. A hydrogel can be formed from a network of polymer chains in which polymers or mixtures thereof are dissolved or dispersed. Hydrogels are composed of three dimensional polymer networks that will swell without dissolving when placed in water or other biological fluids. A hydrogel is significantly more viscous than water or other similar liquids. Hence, for purposes herein, a hydrogel is generally a non-liquid form.

The term "treat" as used herein is defined as maintaining or reducing the symptoms of a pre-existing condition when compared to the same symptoms in the absence of the compound. The term "prevent" as used herein is defined as eliminating or reducing the likelihood of the occurrence of one or more symptoms of a disease or disorder when compared to the same symptom in the absence of the compound. The term "inhibit" as used herein is the ability of the compounds described herein to completely eliminate an activity or reduce the activity when compared to the same activity in the absence of the compound.

The term "admixing" is defined as mixing two components together so that there is no chemical reaction or physical interaction. The term "admixing" also includes the chemical reaction or physical interaction between the two components. As an example, non-covalent entrapment of a pharmacologically active agent in a cross-linked polysaccharide or cross-linked protein matrix is possible. Second, electrostatic or hydrophobic interactions or physical constraint by the matrix can facilitate retention of a pharmaceutically-acceptable compound in the compositions disclosed herein.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the individual range. Thus, included in this numerical range are individual values such as 2, 3, and 4, sub ranges such as from 1-3, from 2-4, from 3-5, etc., as well as 1, 2, 3, 4, and 5, individually. The same principle applies to ranges reciting only one numerical value as a minimum or maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a class of silk-elastinlike proteins A, B, and C are disclosed, as well as a class of anti-cancer agents D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered disclosed from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered disclosed from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

I. Silk-Elastinlike Proteins

The compositions described herein include a silk-elastinlike protein (SELP). SELPs are a class of genetically engineered protein polymers composed of repeating "blocks" of amino acids, referred to as "silk blocks" (Gly-Ala-Gly-Ala-Gly-Ser) and "elastin blocks" (Gly-Val-Gly-Val-Pro). By varying the number of silk and elastin blocks, the rheological properties of the composition can be modified to fit specific applications. For example, the silk-to-elastin ratio and the length of the silk and elastin block domains as well as the SELP concentration can be modified to optimize gelling upon administration of the composition to a subject.

Examples of SELPs useful herein include, but are not limited to, $[(VPGVG)_8(GAGAGS)_2]_{18}$;  (SEQ ID NO: 1)

$[(GVGVP)_4(GAGAGS)_9]_{13}$;  (SEQ ID NO: 2)

$[(VPGVG)_8(GAGAGS)_4]_{12}$;  (SEQ ID NO: 3)

$[(VPGVG)_8(GAGAGS)_6]_{12}$;  (SEQ ID NO: 4)

$[(VPGVG)_8(GAGAGS)_8]_{11}$;  (SEQ ID NO: 5)

$[(VPGVG)_{12}(GAGAGS)_8]_8$;  (SEQ ID NO: 6)

$[(VPGVG)_{16}(GAGAGS)_8]_7$;  (SEQ ID NO: 7)

$[(VPGVG)_{32}(GAGAGS)_8]_5$;  (SEQ ID NO: 8)

$[(GAGAGS)_{12}GAAVTGRGDSPASAAGY(GAGAGS)_5(GVGVGP)_8]_6$;  (SEQ ID NO: 9)

$[(GAGAGS)_2(GVGVP)_4GKGVP(GVGVP)_3]_6$;  (SEQ ID NO: 10)

$[(GAGAGS)_2(GVGVP)_4GKGVP(GVGVP)_3]_{12}$;  (SEQ ID NO: 11)

$[(GAGAGS)_2(GVGVP)_4GKGVP(GVGVP)_3]_{18}$;  (SEQ ID NO: 12)

$[(GAGAGS)_2(GVGVP)_4GKGVP(GVGVP)_3]_{17}(GAGAGS)_2$;  (SEQ ID NO: 13)

$[(GAGAGS)_2(GVGVP)_4GKGVP(GVGVP)_3(GAGAGS)_2]_{13}$;  (SEQ ID NO: 14)

$[GAGAGS(GVGVP)_4GKGVP(GVGVP)_3(GAGAGS)_2]_{12}$;  (SEQ ID NO: 15)

$[(GVGVP)_4GKGVP(GVGVP)_{11}(GAGAGS)_4]_5(GVGVP)_4GKGVP(GVGVP)_{11}(GAGAGS)_2$;  (SEQ ID NO: 16)

$[(GVGVP)_4GKGVP(GVGVP)_{11}(GAGAGS)_4]_7(GVGVP)_4GKGVP(GVGVP)_{11}(GAGAGS)_2$;  (SEQ ID NO: 17)

$[(GVGVP)_4GKGVP(GVGVP)_{11}(GAGAGS)_4]_9(GVGVP)_4GKGVP(GVGVP)_{11}(GAGAGS)_2$;  (SEQ ID NO: 18)

$[GAGS(GAGAGS)_2(GVGVP)_4GKGVP(GVGVP)_{11}(GAGAGS)_5GA]_6$;  (SEQ ID NO: 19)

$[(GAGAGS)_2GVGVPLGPLGP(GVGVP)_3GKGVP(GVGVP)_3]_{15}$  (SEQ ID NO: 20)

$(GAGAGS)_2$;
and $[(GAGAGS)_2GVGVPGFFVRARR(GVGVP)_3GKGVP(GVGVP)_3]_{15}$  (SEQ ID NO: 21)

$(GAGAGS)_2$.

In one aspect, the SELP is SELP-27K, SELP-47K, SELP-415K, SELP-815K, SELP-pSE8Y, SELP-pS2E8Y, SELP-pS4E8Y, or any combination thereof. In another aspect, the SELP is (SEQ ID NO: 22)
MDPVVLQRRDWENPGVTQLNRLAAHPPFASDPM[GAGS(GAGAGS)$_2$
(GVGVP)$_4$GKGVP(GVGVP)$_{11}$(GAGAGS)$_5$GA]$_6$GAMDPGRYQDLRSH
HHHHH (SELP-815K);
or (SEQ ID NO: 23)
MDPVVLQRRDWENPGVTQLVRLAAHPPFASDPMGAGSGAGS[(GVGV
P)$_4$GKGVP(GVGVP)$_3$(GAGAGS)$_4$]$_{12}$(GVGVP)$_4$GKGVP(GVGVP)$_3$
(GAGAGS)$_2$GAGAMDPGRYQDLRSHHHHHH (SELP-47K).

In another aspect, the silk-elastinlike polymer can be a variant of a SELP. A "variant" with reference to a silk-like unit or elastin-like unit refers to a silk-like unit or elastin-like unit that has an amino acid sequence that is altered by one or more amino acids. Typically, a unit sequence is altered by 1, 2, or 3 amino acids. The variant can have an amino acid replacement(s), deletion(s), or insertion(s). For example, the variant can have "conservative" changes, wherein a substituted amino acid has similar structural or chemical properties (e.g., replacement of valine with isoleucine). In some cases, a variant can have "nonconservative" changes (e.g. replacement of a glycine with a tryptophan). Similar minor variations can also include amino acid deletions or insertions, or both. In addition to the teachings herein, guidance in determining which amino acid residues can be substituted, inserted, or deleted without abolishing bioactivity can be found using computer programs well known in the art such as, for example, DNASTAR software.

In one aspect, the SELP is sheared prior to formulating the chemoembolic composition. In one aspect, a solution of the SELP is introduced into a homogenizer through a needle valve at a pressure of from 1,500 psi to 17,000 psi. Exemplary methods for producing sheared SELPs are provided in Price et al, "Effect of shear on physicochemical properties of matrix metalloproteinase responsive silk-elastinlike hydrogels," *J. Control. Release*, 2014, 195:92-98. Not wishing to be bound by theory, the shearing of the SELP solution breaks intramolecular hydrogen bonds between the silk-like motifs. Shearing linearizes the protein, which causes reduction in solution viscosity and increases the opportunity for the formation of intermolecular interactions between the silk-like domains of distinct SELP polymers. Shearing can ultimately increase the peak modulus and gelation rate of the SELP. Increased intermolecular bonding enables the formation of a stiffer and more homogeneous network.

II. Matrix Metalloproteinase Cleavage Sites

In one aspect, the SELP includes one or more matrix metalloproteinase (MMP) cleavage sites. MMPs are a family of structurally related endopeptidases that exist in a dynamic balance with tissue inhibitors of metalloproteases (TIMPs) to control a myriad biological functions requiring extracellular matrix (ECM) degradation. Proper function and regulation of MMPs is responsible for diverse biological functions such as angiogenesis, embryonic development, and wound healing. There are over 20 known specific MMPs, divided into subgroups based on their additional domains and known biological functions. The main classes of MMPs are collagenases, gelatinases, stromelysins, matrilysins, membrane-type MMPs, and other unclassified MMPs.

In one aspect, the MMP cleavage site is MMP-1, MMP-2, MMP-3, MMP-7, MMP-8, MMP-9, or a combination thereof. MMPs-2 and -9 are known as gelatinase types A and B, respectively, due to their known ability to degrade gelatin (denatured collagen). In normal situations, MMPs-2 and -9 contribute to several processes involving cell migration and signaling, for example, angiogenesis and inflammation/innate immunity. However, these MMPs have also been shown to be overexpressed in certain disease states relative to their expression in healthy tissue.

In addition to MMP-2 and -9 cleavage sites, other protease cleavage sites may be incorporated in the protein polymer (see Table 1). Protease-specific sites can be chosen to target a specific response in the desired microenvironment. The reorganization that occurs during wound healing, if predicted to be a normal response, will use known enzymes during various stages. The breakdown of the matrix will react to the enzymes released during a particular stage to have the most beneficial effect. This includes incorporation of specifically recognized cleavage sites for particular MMPs and other proteases. Sequences that are cleaved by specific enzymes used for extracellular matrix remodeling can be optimized for the release and degradation of recombinant protein hydrogels based on site preferences. The sequence will depend on the MMP or other proteases, regardless of the protein polymer used, and may be inserted in an advantageous location within the protein polymer.

TABLE 1

MMP Substrates and Cleavage Sequences

| Substrate | Cleavage Sequence |
|---|---|
| MMP-1, -8 (collagenases) | |
| Type I collagen | APGQIAGQ (SEQ ID NO 24); |
| Type II collagen | GPQGLAGQ (SEQ ID NO 25); |
| Type III collagen | GPLGIAGI (SEQ ID NO 26); |
| Aggrecan | IPENFFGV (SEQ ID NO 27); |
| MMP-3 (stromelysins) | |
| Type IX collagen | MAASAKRE (SEQ ID NO 28); |
| Fibronectin | PFSPLVAT (SEQ ID NO 29); |
| MMP-2, -9 (gelatinases) | |
| Type IV collagen | GPQGIFGQ (SEQ ID NO 30); |
| Cartilage link protein | RAIHIQAE (SEQ ID NO 31); |
| MMP-7 (matrilysin) | |
| Laminin | GPLGIAGQ (SEQ ID NO 32); |
| Elastin | GPQAIAGQ (SEQ ID NO 33); |

In one aspect, the SELP is the sequence below, where the MMP-responsive sequence is indicated in bold text.

(SEQ ID NO: 34)
[GAGS(GAGAGS)$_2$(GVGVP)$_3$GVGGPQGIFGQPGKGVP(GVGVP)$_{11}$(GAGAGS)$_5$GA]$_6$;

Methods for producing SELPs with one or more matrix metalloproteinase (MMP) cleavage sites are provided in international patent application publication WO 2013181471, which is herein incorporated by reference in its entirety.

III. Anti-Cancer Agents

In one aspect, the chemoembolic agents described herein include one or more anti-cancer agents. In one aspect, the anti-cancer agent is paclitaxel, docetaxel, gemcitabine, a palatinate, doxorubicin, geldanamycin, epirubicin, 9-aminocamptothecin, sorafenib, or any combination thereof. In a further aspect, the anti-cancer agent is a neutral compound or the pharmaceutically-acceptable salt thereof. In one aspect, the anti-cancer agent is doxorubicin. In another aspect, the anti-cancer agent is sorafenib. In yet another aspect, the anti-cancer agent is a combination of doxorubicin and sorafenib. In any of the above aspects, the doxorubicin can be a neutral compound or can be doxorubicin hydrochloride. Furthermore, in any of the above aspects, the sorafenib can be a neutral compound or can be sorafenib tosylate.

Any of the anti-cancer agents useful herein can be the pharmaceutically acceptable salt or ester thereof. Pharmaceutically acceptable salts are prepared by treating the free molecule with an appropriate amount of a pharmaceutically acceptable acid or base. Representative pharmaceutically acceptable acids include acetic acid, adipic acid, ascorbic acid, aspartic acid, benzoic acid, citric acid, glutamic acid, glycolic acid, hydrobromic acid, hydrochloric acid, lactic acid, lauric acid, maleic acid, malic acid, mandelic aid, nicotinic acid, nitric acid, oleic acid, oxalic acid, palmitic acid, phosphoric acid, proprionic acid, salicylic acid, stearic acid, succinic acid, sulfuric acid, tartaric acid, toluenesulfonic acid, and the like. Representative pharmaceutically acceptable bases include ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, dimethylamine, trimethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of anti-cancer agent to base used are chosen to provide the ratio desired for any particular salts.

Ester derivatives are typically prepared as precursors to the acid forms of the compounds and accordingly can serve as prodrugs of anti-cancer agents. Generally, these derivatives will be lower alkyl esters such as methyl, ethyl, and the like. Amide derivatives (—CO)NH$_2$, —(CO)NHR, and —(CO)NR$_2$, where R is an alkyl group as defined above, can be prepared by reaction of a carboxylic acid-containing compound with ammonia or a substituted amine. Alternatively, the esters can be fatty acid esters.

IV. Chemoembolic Agents and Methods for Producing the Same

Provided herein are methods for producing chemoembolic agents. In one aspect, the method includes admixing one or more anti-cancer agents with a silk-elastinlike protein. In a further aspect, the anti-cancer agent is admixed with a liquid composition of the silk-elastinlike protein, wherein the silk-elastinlike protein is from 2% to 20% w/w of the liquid composition, or is 2, 3, 4, 5, 6, 7, 8, 9, 10, 11, 12, 13, 14, 15, 16, 17, 18, 19, or 20% w/w of the liquid composition, where any value can be a lower or upper end-point of a range (e.g., 3% to 18%, 7% to 15%, etc.). In one aspect, the silk-elastinlike protein is at or near 9% w/w of the liquid composition. In another aspect, the silk-elastinlike protein is at or near 12% w/w of the liquid composition.

In one aspect, the liquid composition of SELP can be a solution, suspension, gel, hydrogel, or micellar solution in water. In an alternative aspect, the liquid composition can be a solution, suspension, gel, hydrogel, or micellar solution in a buffer and/or solvent mixture such as, for example, a mixture of water and a nonreactive solvent with which water is miscible such as, for example, DMSO.

In one aspect, the anti-cancer agent is admixed with the liquid composition of SELP as a dry solid. In a further aspect, the dry solid can be a powder. Chemotherapeutics in powder form powder having a particle size of from 300 μm to 10 μm, 200 μm to 10 μm, 100 μm to 1 μm, 0.5 μm to 50 μm, 1 μm to 25 μm, 1 μm to 10 μm, or 1 μm to 5 μm. In a still further aspect, the dry solid is milled prior to introduction to the liquid composition of SELP to provide uniformity to the composition and to ensure even mixing. In an alternative aspect, the anti-cancer agent is admixed with the liquid composition as a solution comprising a solvent. Further in this aspect, the solvent can be water, DMSO, a combination thereof, or another solvent.

In one aspect, the anti-cancer agent is from 1 mg/mL to 100 mg/mL of the final chemoembolic agent. In a further aspect, the anti-cancer agent is 1, 10, 25, 50, 75, or 100 mg/mL of the chemoembolic agent, where any value can be a lower or upper end-point of a range (e.g., 10 to 75, 25 to 50, etc.). In one aspect, the anti-cancer agent is 25 mg/mL of the chemoembolic agent. In another aspect, the anticancer agent is 50 mg/mL of the chemoembolic agent.

In one aspect, the sheared silk-elastinlike protein is SELP-815K and is present from 5% to 15% w/w of the chemoembolic agent and the anti-cancer agent is the pharmaceutically-acceptable salt of doxorubicin, the pharmaceutically acceptable salt of sorafenib, or a combination thereof.

The compositions disclosed herein can also include one or more additional biologically active ingredients used in combination with the chemoembolic agents described herein. In one aspect, an anti-angiogenic agent can be incorporated into chemoembolic agents described herein.

In one aspect, the anti-angiogenic agent is a Tyrosine Kinase Inhibitor(TKI). Further in this aspect, a TKI is chosen because angiogenesis is, in large part, initiated and maintained by cell signaling through receptor tyrosine kinases (RTKs). In one aspect, RTKs include receptors for several angiogenesis promoters, including VEGF, which stimulates vascular permeability, proliferation, and migration of endothelial cells; PDGF, which recruits pericytes and smooth muscle cells that support the budding endothelium; and FGF, which stimulates proliferation of endothelial cells, smooth muscle cells, and fibroblasts. In another aspect, the anti-angiogenic agent is a TKI selected from the group that includes sunitinib malate (SUN), pazopanib hydrochloride (PAZ), sorafenib tosylate (SOR), vandetanib (VAN), or a combination thereof.

The chemoembolic agents disclosed herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution and other aqueous physiologically balanced salt solutions. Nonaqueous vehicles, such as fixed oils, vegetables oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin, and benzyl alcohol. In certain aspects, the pH of the formulation can be modified depending on the mode of administration. Additionally, the pharmaceutical composition can include a carrier, thickener, diluent, preservative, surfactant, or the like, in addition to the compounds described herein.

In one aspect, the chemoembolic agent can reduce blood flow to a tumor, resulting in reduction of tumor volume and/or inhibition of tumor growth. In another aspect, the chemoembolic agent can provide localized, sustained release of an anti-cancer agent in the vicinity of a tumor. This, in turn, results in reduced systemic effects and lower overall toxicity of treatment, which allows for patients to avoid treatment delays and to follow the originally-prescribed schedule of treatment. In one aspect, by following the original treatment schedule with respect to the anti-cancer agent, patient outcomes and recovery are improved.

V. Contrast Agents

In one aspect, the chemoembolic agent contains a contrast agent. The contrast agent can be detected using techniques known in the art including X-ray, NMR imaging, ultrasound, and fluoroscopes. In a further aspect, the contrast agent is a radiographic contrast agent. Further in this aspect, the radiographic contrast agent can be tantalum metal particles (Ta), gold particles, or iodinated compounds. In one aspect, the contrast agent can be tantalum particles having a particle size of from 0.5 μm to 50 μm, 1 μm to 25 μm, 1 μm to 10 μm, or 1 μm to 5 μm. In another aspect, the contrast agent is tantalum particles in the amount of from 10% to 60%, 20% to 50%, or 20% to 40% (w/w). In one aspect, up to 30% (w/w) of Ta can be included in the formulations disclosed herein. In one aspect, inclusion of Ta can be beneficial to interventional radiologists in the operating room. In another aspect, the contrast agent can be a fluoroscopic contrast agent. Further in this aspect, the fluoroscopic contrast agent can be tantalum oxide ($TaO_2$, $Ta_2O_5$) particles.

VI. Physical Properties of Chemoembolic Agents

In one aspect, the chemoembolic agent is an injectable composition at room temperature (e.g., at a temperature of from 18 to 23° C.). In a further aspect, the chemoembolic agent has a viscosity of less than or equal to 2500 cP at room temperature. In one aspect, the chemoembolic agent has a viscosity of less than or equal to 100, 150, 200, 250, 300, 350, 400, 450, 500, 550, 600, 650, 700, 750, 800, 900, 1000, 1250, 1500, 1750, 2000, 2250, or 2500 cP at room temperature.

In a further aspect, at human body temperature (e.g., 37° C.), the chemoembolic agent is a hydrogel. Criteria for a liquid embolic agent injectable through a clinical microcatheter are further described in Table 2.

TABLE 2

| Criteria for Injectable SELP-815K Liquid Embolic Agent | |
|---|---|
| Design Criterion | Specification Parameter Targets and Rationale |
| Injectability | Viscosity ≤150 cP required for injection through clinical microcatheters |
| Gelation kinetics | Sol-gel transition time ≤5 minutes required for gel retention in arterial vessel with minimal venous washout |

TABLE 2-continued

Criteria for Injectable SELP-815K Liquid Embolic Agent

| Design Criterion | Specification Parameter Targets and Rationale |
|---|---|
| Embolic effect | Final gel stiffness, storage modulus $G' \geq 1 \times 10^5$ Pa required for stable maintenance of gel embolus against hepatic blood pressure |

VII. Administration of Chemoembolic Agents

In one aspect, provided herein is a method for delivering an anti-cancer agent to a subject. In one aspect, the method includes the step of administering the chemoembolic agent into the tumor vasculature of the subject. In a further aspect, the chemoembolic agent is administered via catheter. In a still further aspect, the catheter is an endovascular catheter. In one aspect, the chemoembolic agent is administered by transcatheter arterial chemoembolization (TACE).

In a further aspect, the anti-cancer agent is released from the chemoembolic agent for a period of at least three days. In an alternative aspect, the anti-cancer agent is released from the chemoembolic agent for at least one week.

In another aspect, the amount of anticancer agent released from the chemoembolic agent is from 30% to 100%, or is 30, 40, 50, 60, 70, 80, 90, or 100% of the anticancer agent present in the initial chemoembolic composition, where any value can be a lower or upper end-point of a range (e.g., 60% to 100%, 80% to 100%, etc.). In one aspect, the SELP hydrogel can release the anti-cancer agent at a controlled rate. By varying the composition of the SELP hydrogel and the selection of the anti-cancer agent and/or the form of the anti-cancer agent (e.g., particular agent or combination of agents, salts, esters, free drugs, liquid or powder form, etc.), it is possible to fine-tune the release pattern of the anticancer agent from the SELP hydrogel.

VIII. Method of Action of Chemoembolic Agents

In one aspect, the chemoembolic agents disclosed herein reduce or inhibit blood flow to a tumor present in a subject. In a further aspect, administering the chemoembolic agents into the tumor vasculature reduces or inhibits the growth of a tumor.

In one aspect, provided herein is a method for treating cancer in a subject, the method including the step of administering the chemoembolic agent to the subject. In a further aspect, the cancer is a liver cancer or bile duct cancer such as, for example, hepatocellular carcinoma, fibrolamellar carcinoma, cholangiocarcinoma, angiosarcoma, or hepatoblastoma. In another aspect, the cancer is a metastasis in the liver from another cancer such as colon cancer, breast cancer, carcinoid tumors or other neuroendocrine tumors, islet cell tumors of the pancreas, ocular melanoma, sarcomas, and/or other vascular primary tumors in the body.

In addition to releasing the anti-cancer agent at a controlled rate, the SELP hydrogel also creates an artificial embolus within the vessel. In other aspects, the SELP hydrogel can include one or more embolic agents. Commercially available embolic agents can be microparticles. The size and shape of the microparticles can vary. In one aspect, the microparticles can be composed of polymeric materials. An example of such is the Bearin™ nsPVA particles manufactured by Merit Medical Systems, Inc., which are composed of poly(vinyl alcohol) ranging in size from 45 μm to 1,200 μm; HepaSphere™ Microspheres (spherical, hydrophilic microspheres made from vinyl acetate and methyl acrylate) ranging in size from 30 μm to 200 μm; and QuadraSphere® Microspheres (spherical, hydrophilic microspheres made from vinyl acetate and methyl acrylate) ranging in size from 30 μm to 200 μm, all of which are manufactured by Merit Medical Systems, Inc. In another aspect, the microsphere can be impregnated with one or more metals that can be used as a contrast agent. An example would be EmboGold® Microspheres manufactured by Merit Medical Systems, Inc., which are made from trisacryl cross-linked with gelatin impregnated with 2% elemental gold ranging in size from 40 μm to 1,200 μm.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the purity and yield obtained from the described process. Only reasonable and routine experimentation will be required to optimize such process conditions.

Example 1

Synthesis of SELP

A silk-elastinlike protein polymer was synthesized with 6 repeats of blocks composed of 8 silk-like units, 15 elastin-like units, and 1 lysine-substituted elastin-like unit (SELP-815K). The SELP-815K was sheared at >17,000 psi to enhance homogeneity and improve material properties.

Example 2

Materials

Sorafenib tosylate, sorafenib base, and doxorubicin HCl were purchased from LC Laboratories and doxorubicin base was purchased from MedKoo Biosciences. Chemicals and salts used included acetonitrile (Fisher Scientific), ammonium acetate (Fisher Scientific), sodium dodecyl sulfate (SDS, Sigma Aldrich), and phosphate buffered saline tablets (Amresco).

Example 3

Formulation Development and Drug Incorporation

SELP-815K formulations were prepared at 12% w/w in 1× phosphate buffered saline (PBS). Powder drugs were milled for 12 hours to reduce crystal size and variability using a custom built ball mill. Milled samples were inspected microscopically to verify homogeneity. Two methods of drug incorporation were investigated. First, drugs were dissolved in DMSO at a concentration of 100 mg/mL and 50 μL of the drug solution was spiked into 150 μL of liquid 12% SELP-815K followed by 10 seconds of manual mixing; this resulted in a 9% w/w SELP concentration and a 25 mg/mL drug loading. Drug loading concentration was chosen based on manufacturer specified loading of doxorubicin in DEBs. The same loading was used for sorafenib.

Second, milled powder drug was incorporated directly into 150 μL of liquid 12% w/w SELP-815K and 50 μL saline was added to dilute the SELP to 9% w/w (equivalent to the samples with drug dissolved in DMSO) followed by mechanical mixing using a custom built overhead mixer equipped with a 1/16" diameter spiral impeller for 10 seconds at 5400 rpm, resulting in a 25 mg/mL drug loading. For dual drugs, drug loading was 12.5 mg/mL for each drug, for a total drug loading of 25 mg/mL. Samples were chilled on ice until tested. Samples incorporating powder drug in 12% w/w SELP-815K were prepared without dilution; however, the volume addition of the powdered drug was not considered in the calculation of the SELP concentration. Samples with powdered drug were tested at 25 and 50 mg/mL for single drug loaded samples and 25 mg/mL per drug for dual drug loaded samples.

Example 4

Rheological Characterization

An AR 550 stress-controlled rheometer from TA Instruments (New Castle, Del.) was used for rheological testing. A cone-and-plate configuration equipped with a stainless steel 20 mm diameter, 4 degree geometry was used. An oscillation procedure with a temperature ramp from 18° C. to 37° C. (5.76° C./min) at an angular frequency of 6.283 rad/s was run to measure viscosity, followed by an oscillatory time sweep of 3 hours held at 37° C., using angular frequency of 6.283 rad/s and 0.1% strain to measure the dynamic storage modulus, G'. Individual samples previously prepared and stored frozen were thawed just before testing at 18-23° C. and centrifuged at 14,000 rpm (Centrifuge 5417C, Eppendorf) for 30 seconds. Drug was incorporated as described previously, immediately before testing. A 150 μL aliquot of test solution was immediately transferred to the instruments Peltier plate, which was pre-chilled to 18° C. Measurements were conducted in triplicate.

SELP solution loaded with doxorubicin, sorafenib, or both drugs in various chemical and physical forms was evaluated to qualify the various formulations with respect to the targeted physical and mechanical requirements of an injectable liquid chemoembolic. The salt forms of the drugs, doxorubicin hydrochloride (dox HCl) and sorafenib tosylate (soraf Tos), being the more soluble forms of the drugs used clinically, were tested first. Dox HCl was mixed into the SELP solution either directly as a powder or as a solution dissolved in DMSO. All experiments with both drugs were conducted at a consistent drug loading level based on the clinically specified loading level of doxorubicin with drug-eluting beads at 25 mg/mL.

Figures 2A, 2B, 2C:
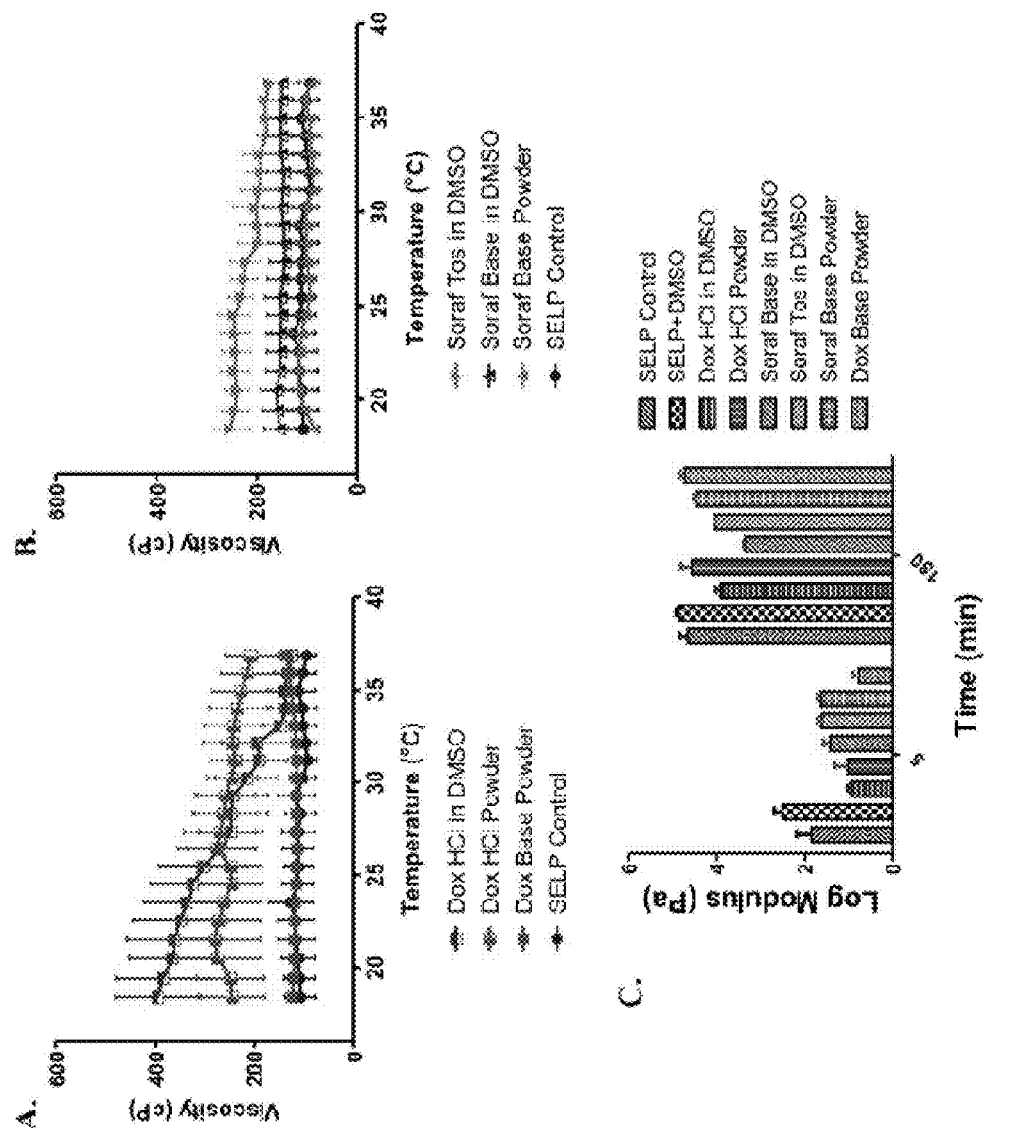
FIGS. 2A-2C show rheological evaluation of 9% SELP-815K loaded with 25 mg/mL doxorubicin and/or sorafenib, in both salt and base forms, incorporated into the polymer solution either dissolved in DMSO or in powder form.

Immediately, the addition of dox HCl to the SELP solution caused a noticeable increase in viscosity. The viscosity of the SELP solution with dox HCl, incorporated either as a drug powder or (more so) as a DMSO solution was more than 2-fold greater than the SELP control with no drug (FIG. 2A). Additionally, the viscosity of the SELP-dox HCl-DMSO showed a temperature effect, unusual for SELP-815K solutions. The initial average viscosity at 18° C. of 394±149 cP decreased with increasing temperature to 123±44 cP at 37° C. This temperature thinning effect was not seen with the dox HCl powder, which averaged 250±114 cP throughout the temperature ramp.

Sorafenib tosylate was mixed into SELP solution either dissolved in DMSO or in powder form and similarly tested. The same trends as for dox HCl were observed, though the magnitude of the changes was less (FIG. 2B). As observed with dox HCl, SELP with soraf Tos in DMSO had greater viscosity than the SELP control and displayed temperature thinning, although to a lesser degree than SELP with dox HCl. Sorafenib base in DMSO also displayed an increased viscosity, but not temperature thinning.

While the increase in viscosity of the SELP solution with the salt forms of the drugs added in DMSO could be due to the drugs or the DMSO, the temperature thinning effect is due to the salt forms of the drugs, not the DMSO, since the effect was not seen with sorafenib base in DMSO. Since the viscosity of a polymer solution is dependent on the chemical and physical interactions of the polymer chains, it follows that the salt forms of the drugs in DMSO affect these interactions. The incorporation of dox HCl and soraf Tos or base forms as solutions in DMSO increased the viscosity of the SELP solution to levels that exceeded the acceptable injectable viscosity of <150 cP at room temperature, making them unsuitable SELP liquid embolic formulations. On the other hand, the incorporation of either drug in base form as a powder did not change the viscosity or the viscosity behavior as a function of the temperature compared to the SELP control (FIGS. 2A and 2B). These formulations were deemed to meet the injectability criterion for a SELP liquid embolic.

The SELP drug formulations were further tested to determine their gel stiffness at 37° C. FIG. 2C shows the storage modulus, G', of the gels at 5 and 180 minutes. G' is a measure of the material stiffness and an indicator of gel network crosslinking. To allow for the addition of the drug, the SELP concentration of the tested formulations was decreased to 9% w/w, rather than the 12% w/w previously defined for the SELP liquid embolic agent. Thus, the gel modulus was expected to be less than the target $\geq 1 \times 10^5$ Pa specified in Table 2. Therefore, the change in modulus as a function of drug incorporation relative to the SELP control was used to assess the effect of drug additions and the relative suitability of the formulations as liquid embolic agents. The results indicated that the storage moduli of the gels at 5 minutes decreased when drug was added in any form and more so with doxorubicin than sorafenib. At 180 minutes, however, only the formulations with drug added in DMSO showed reduced moduli. Interestingly, only SELP with DMSO showed no reduction in modulus. Doxorubicin and sorafenib added as powders had moduli comparable to the SELP control. However, none of these observed differences were statistically significant and they were not used to exclude formulations from further study. Therefore, injection viscosity was the primary criterion used to move chemoembolic drug candidates forward and the base forms of the drugs were selected to continue in the remaining characterization and release studies. Both methods of drug incorporation were studied.

Example 5

SEM Analysis of Drug-Loaded Gels

Gel samples were examined by scanning electron microscopy (SEM) using an FEI Quanta 600F for qualitative analyses. Samples were prepared with drugs as described previously, drawn into 0.5 cc insulin syringes, and sealed with paraffin film to prevent evaporation. The syringes were incubated overnight at 37° C. to allow curing. The resulting gels were extruded from the syringe barrel (after cutting off the needle), sliced into 20 μL disks, and weighed. Gel samples were flash frozen in liquid nitrogen and lyophilized for 24 hours. The disks were mounted on carbon tape and coated with a 6 nm layer of gold palladium (Gatan 682 Precision Etching Coating System) for imaging. Secondary electron images were taken with beam parameters of 3.0 spot size and 10.00 kV voltage. Images were also taken post-drug release by the same method.

Figures 3A, 3B:
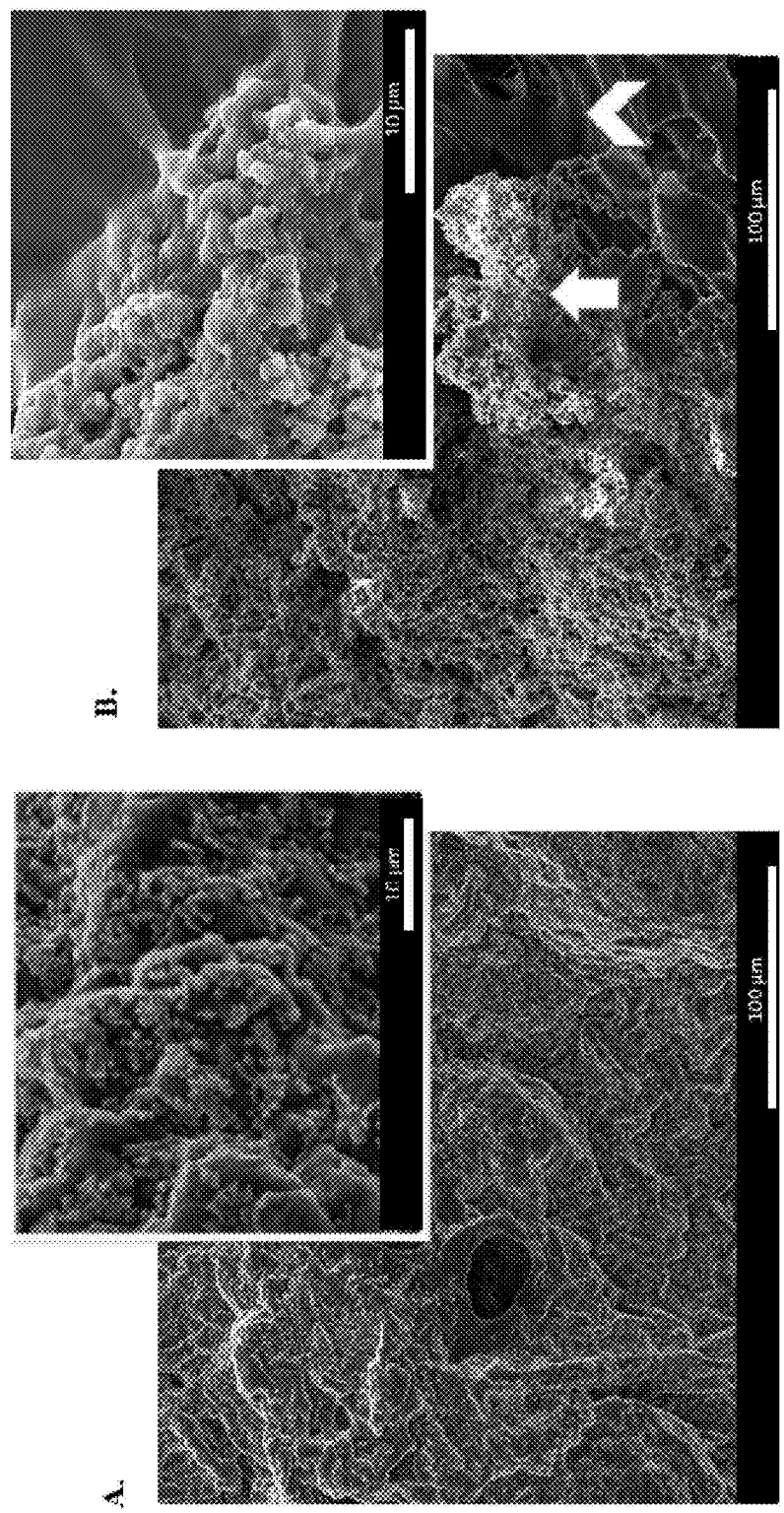
FIGS. 3A and 3B show scanning electron micrographs of 9% SELP-815K gels loaded with base forms of both doxorubicin and sorafenib.

Scanning electron micrographs were examined to assess the extent and uniformity of drug dispersion throughout the SELP matrix. Representative images of the dual drug loaded gel shown in FIG. 3A confirm the higher level of drug homogeneity throughout the matrix when the drug is incorporated in DMSO versus the powder. In the gel incorporating the two drugs in DMSO (FIG. 3A), distinct crystalline structures of doxorubicin base (star polyhedron formations) and sorafenib base (cubic polyhedrons) as determined from SEM images of single drug loaded gels were possibly induced during the flash freezing and dehydration process (visible in the inset images). The distinct crystals uniformly coat the entire surface of the polymer matrix. The same level of homogeneity was not present in the gel samples incorporating the powdered drugs (FIG. 3B). As expected, the hydrophobic drugs formed clusters that were interspersed throughout the matrix. The SELP polymer matrix is indicated by the arrowhead and the drug cluster by the arrow. Often, projections of the polymer were observed as caging the drug clusters. Additional images of the 12% SELP-815K gels loaded with the powdered drugs that clearly show the polymer projections surrounding the drug clusters are shown in FIG. 9.

Figure 9A:
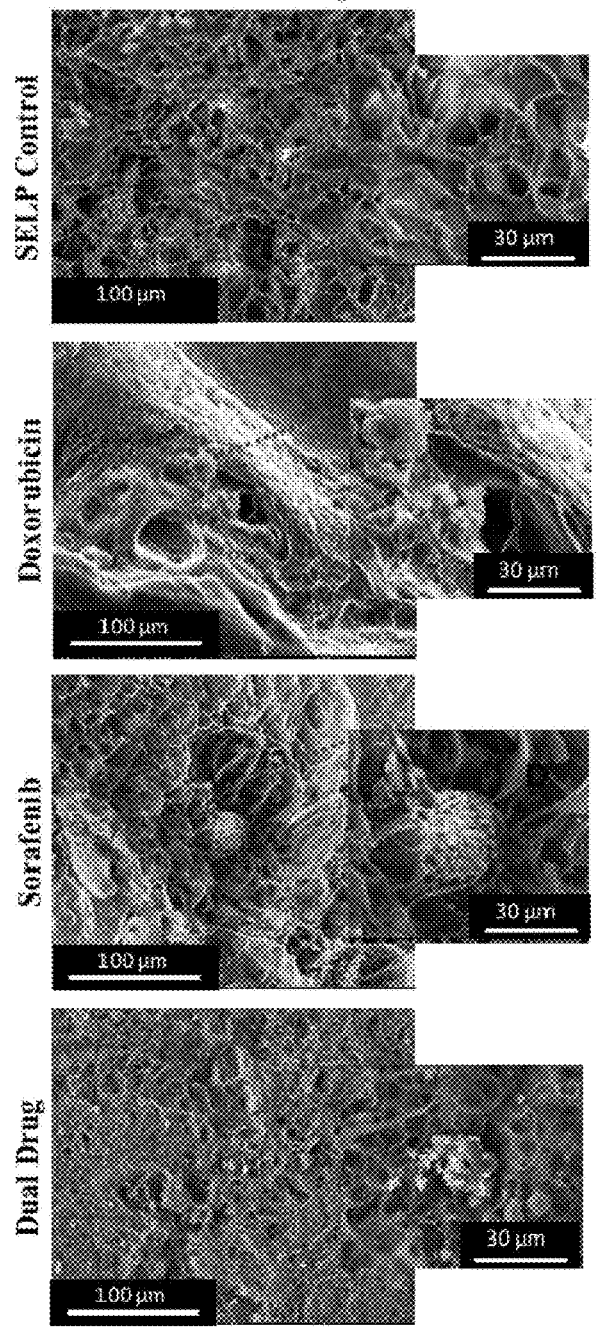
FIGS. 9A-9B show scanning electron micrographs of 12% SELP-815K gels loaded with base forms of both doxorubicin and sorafenib powders.
Figure 9B:
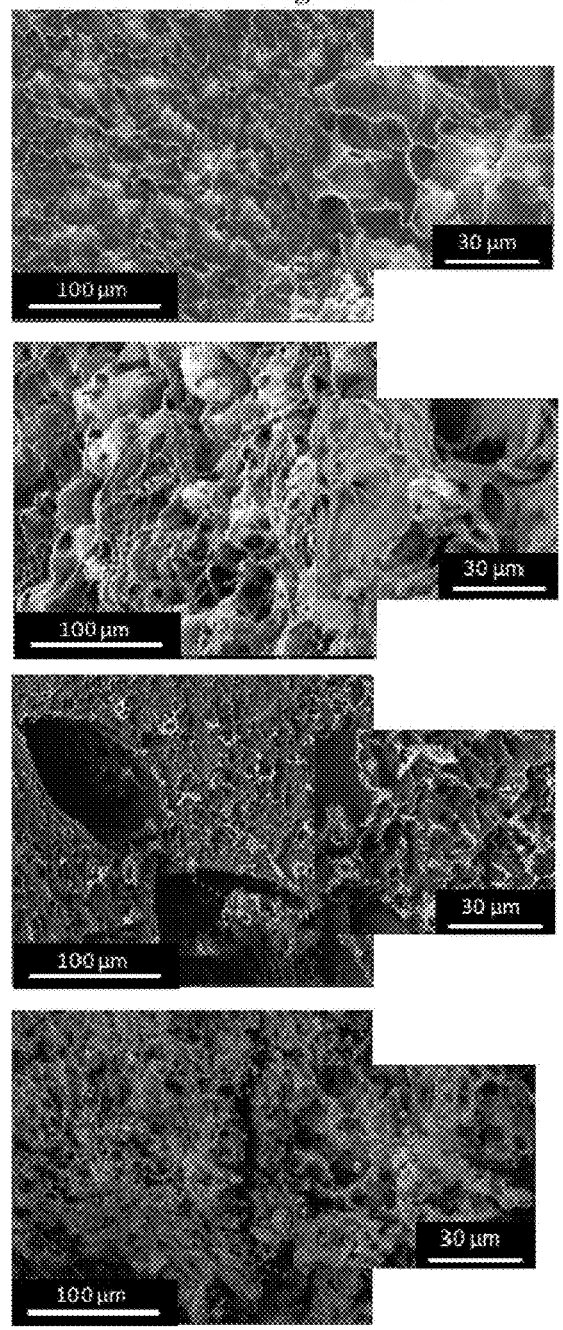

The pre-drug release SEM images presented in FIG. 9 illustrate the clustering effect of the hydrophobic drugs as well as their entrapment by the SELP matrix. In comparison to the 9% SELP-815K drug loaded samples, the drug clusters in the 12% gels tended to be smaller and more distinct. In the post-release samples, large clusters were not visible. Rather, wisp-like layers with crystalline features were spread on the polymer foundation (better clarity in the inset images). A difference between the doxorubicin and sorafenib groups could not be distinguished. Compared to the 9% gels, the lack of large drug clusters in the 12% gels and the greater dispersion of drug could have been responsible for the lesser drug release rates, although the increased SELP-815K concentration could also have contributed.

Example 6

In Vitro Drug Release

The drug loaded SELP solutions were drawn into 0.5 cd insulin syringes and incubated overnight at 37° C. followed by cutting into gel disks as previously described. Weights were recorded. Individual gels were placed into 8 dram glass vials, to which 25 mL of release media consisting of 1×PBS, 1% SDS was added. The elution volume was chosen to ensure sink conditions and complete dissolution of both drugs, if all drug eluted immediately.

At predetermined time points of 1 hour, 3 hours, 6 hours, 12 hours, 1 day, 3 days, 5 days, 7 days, 10 days, 14 days, and 20 and 30 days for extended-release studies, a sample volume was removed for analysis and replaced with fresh media. Vials were sealed and maintained in a shaking incubator at 37° C., 120 rpm. The 9% SELP-815K gels underwent release testing for 14 days. The 12% SELP-815K gels were tested for 30 days.

Drug content in the release media was detected by reverse phase high performance liquid chromatography (RP-HPLC; Agilent Technologies, Santa Clara, CA) using a RPC18 X-Terra column (4.6×250 mm, 5 μm particle size; Waters, Milford, Mass.) and a guard column of the same packing material. The elution gradient at time zero began with mobile phase of 40% 20 mM ammonium acetate and 60% acetonitrile (CAN), which increased to 72% CAN over 9 minutes at a flow rate of 1 mL/min. Percent cumulative release was calculated using the experimental drug loading per disk based on the pre-release weight.

Figures 4A, 4B:
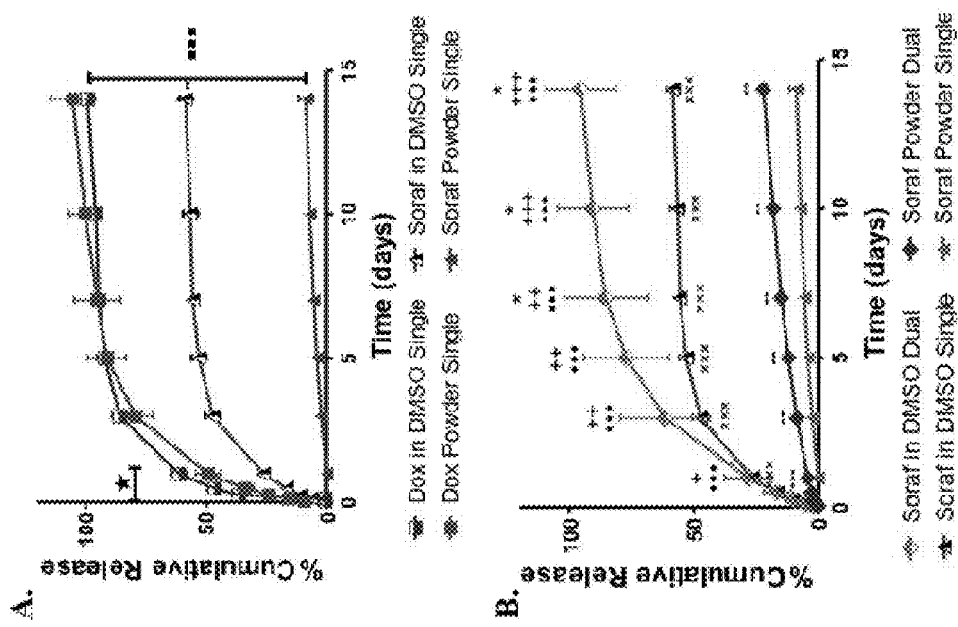
FIGS. 4A and 4B show in vitro drug release from 9% SELP-815K gels loaded with base forms of doxorubicin and sorafenib.

Based on the rheological data, the base forms of each drug were selected for further evaluation. Appropriate drug release is a key component of a chemoembolic system. In vitro release studies were conducted with 9% SELP-815K gels to measure the relative cumulative release of each drug individually and to compare the modes of incorporation for single and concurrent drug loadings. Doxorubicin release in the first 24 hours was significantly greater from the gels with drug in DMSO versus drug powder (FIG. 4A). However, no difference was observed after day 1. More than 50% of the loaded doxorubicin was released in the first day, followed by a decline in release rate and subsequent plateau in days 7 to 14, with nearly all of the loaded drug released by day 14. The relative release differences were more significant between the sorafenib groups at all time points.

Interestingly, the relative release rates for sorafenib changed in the presence of doxorubicin. As seen in FIG. 4B, significant increases were observed between releases of sorafenib from the dual drug loaded gel as compared to the single drug gel with both incorporation methods. It must be noted that the dual drug gels had a 12.5 mg/mL loading for each drug versus 25 mg/mL for single drug gels. Significant increases were observed between all groups. In the DMSO dissolved drug group, sorafenib released from the dual drug loaded gels reached 95% cumulative release, while from the single drug loaded gel, less than 60% cumulative release was achieved. In the powder drug incorporated gels, the dual drug loaded gel resulted in 22% cumulative release versus 8.7% in the single drug loaded gel. Additional results are presented in Table 3. For comparison, the cytotoxicity $IC_{50}$ values of the drugs determined in these studies for human HCC HepG2 cells were 1.72±0.7 μM for sorafenib and 0.62±0.41 μM for doxorubicin, which substantially agree with values reported in the literature (see also Example 10).

TABLE 3

Drug concentration released in vitro at specific time points from the 9% SELP-815K gels

| Experimental Group | Average Concentration (μM)[a] | | |
|---|---|---|---|
| (9% SELP Gels) | Day 1 | Day 7 | Day 14 |
| Dissolved doxorubicin | 32.4 ± 10.8 | 1.3 ± 0.6 | 1.8 ± 0.4 |
| Powder doxorubicin | 23.9 ± 5.6 | 1.9 ± 1.1 | 2.5 ± 1.1 |
| Dissolved doxorubicin (dual) | 11.9 ± 3.1 | 0.8 ± 0.4 | 0.3 ± 0.1 |
| Powder doxorubicin (dual) | 16.8 ± 4.1 | 2.2 ± 0.8 | 1.1 ± 0.5 |
| Dissolved sorafenib | 16.0 ± 2.3 | 1.6 ± 0.7 | 1.2 ± 0.2 |
| Powder sorafenib | 0.0 ± 0.9 | 0.7 ± 0.3 | 1.0 ± 0.4 |
| Dissolved sorafenib (dual) | 7.6 ± 1.7 | 2.3 ± 0.7 | 1.3 ± 0.3 |
| Powder sorafenib (dual) | 1.3 ± 0.3 | 0.9 ± 0.1 | 1.2 ± 0.1 |

[a]Data is represented as the mean ± standard deviation, N = 3

Figures 8A, 8B:
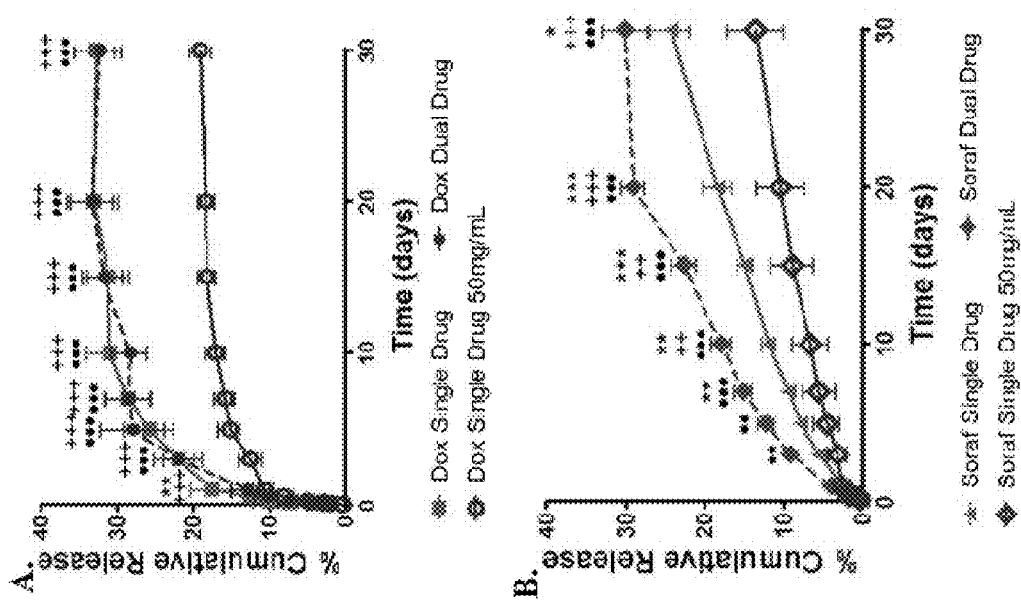
FIGS. 8A-8B show in vitro drug release profiles from 12% SELP-815K loaded with base forms of doxorubicin and sorafenib powders.

Test formulations including single drug loaded 12% SELP-815K gels at 50 mg/mL were evaluated in 30-day in vitro relative release studies. Release profiles were similar to those of the 9% SELP-815K loaded gels (see FIG. 8). Between the 25 mg/mL single drug loaded and dual drug loaded gels, doxorubicin had higher release from the single drug loaded gel during the first 24 hours. After day 1, however, no significant difference was observed. At the end of the experiment (day 30), 30% of the total drug content of doxorubicin was released. Both of these groups showed significant increase in cumulative release over the 50 mg/mL single drug loaded gel and resulted in only 15% cumulative release. The release profiles all reached similar plateaus at one week. Conversely, the sorafenib loaded gels showed more linear release, though less than the doxorubicin. As seen with the 9% SELP-815K gels, sorafenib release was significantly greater from the dual drug loaded gels than the single drug loaded gels. The drug concentrations for days 1, 7, 15, and 30 are presented in Table 4. Concentrations of released drug determined for this group of 12% SELP gels were lower than concentrations released from the 9% gels, although the gels loaded at 50 mg/mL showed concentrations of released doxorubicin in the micromolar range up to 30 days,

TABLE 4

Drug Concentration Released in vitro at Specific Time Points from the 12% SELP-815K Gels

| Experimental Group (12% SELP Gels) | Average Concentration ($\mu M$)[a] | | | |
|---|---|---|---|---|
| | Day 1 | Day 7 | Day 15 | Day 30 |
| Powder doxorubicin | 1.2 ± 0.3 | 0.9 ± 0.4 | 0.9 ± 0.1 | N/A |
| Powder doxorubicin (dual) | 4.7 ± 0.6 | 0.8 ± 0.5 | 1.5 ± 0.4 | N/A |
| Powder doxorubicin (50 mg/mL) | 6.0 ± 0.6 | 0.5 ± 0.2 | 0.8 ± 0.2 | 0.6 ± 0.4 |
| Powder sorafenib | 1.1 ± 0.1 | 0.7 ± 0.2 | 1.2 ± 0.2 | 2.7 ± 0.4 |
| Powder sorafenib (dual) | 1.3 ± 0.2 | 2.1 ± 0.3 | 2.8 ± 0.3 | 0.8 ± 0.7 |
| Powder sorafenib (50 mg/mL) | 1.6 ± 0.6 | 0.9 ± 0.3 | 2.1 ± 0.4 | 3.0 ± 0.4 |

[a]Data is represented as the mean ± standard deviation, N = 5

Example 7

Gel Swelling Ratio

The swelling ratio was measured for the 9% gels, 14 days post-release. Gel disks were removed from the release media, blotted dry with lint-free wipes, and weighed. Samples were then flash frozen in liquid nitrogen and lyophilized for 24 hours. The swelling ratio was calculated as:

$$q = \frac{\text{wet weight}}{\text{dry weight}}$$

Figure 5:
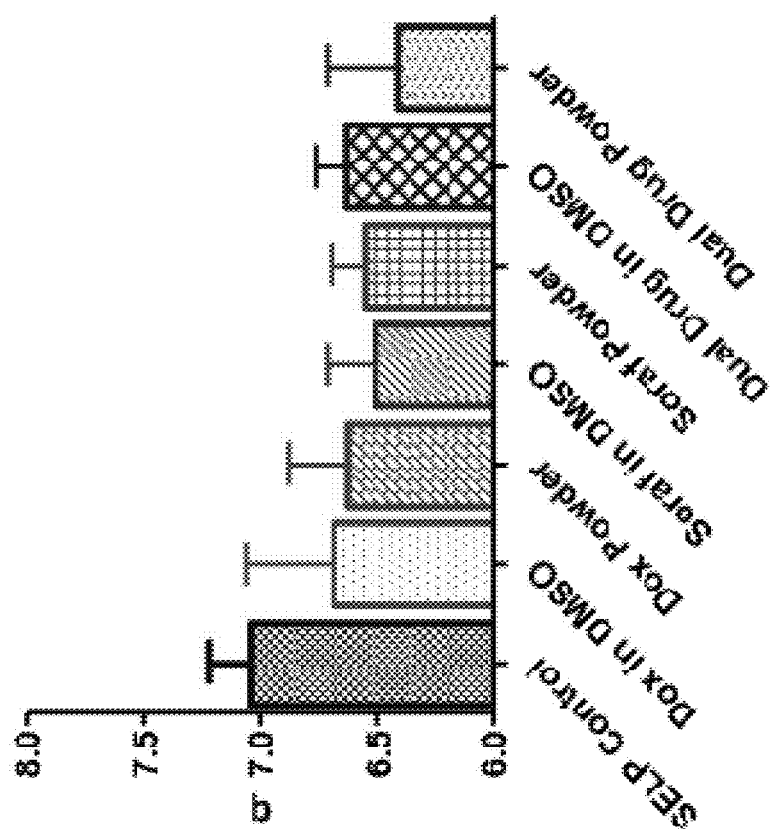
FIG. 5 shows the swelling coefficient, q, for 9% SELP-815K gels loaded with base forms of doxorubicin and sorafenib after 14-day release. No statistically significant differences were determined between any groups.

Hydrogel swelling is affected by the degree of solvation of the gel composition and by the network crosslinking density; both of these factors could affect drug release rates. The swelling coefficient, q, of the gel disks was measured after 14-day release. The gels loaded with sorafenib had lower swelling ratios than the doxorubicin-loaded gels (although this difference was not statistically significant); this is consistent with the slower drug release profile of sorafenib. All drug loaded gels had lower swelling ratios than the SELP control but, again, this difference was not statistically significant. These variations could indicate minor differences in the gel structures caused by the drugs during gelation or they could be due simply to the presence of drug in the gels. The fact that there were no statistically significant differences in the swelling ratios after 14 days and no significant difference in the gel stiffness immediately upon gelation indicates that drug incorporation, at least for the base forms of the drugs as powders, did not significantly alter the gel structure either immediately or after 14 days of release. Swelling coefficients are presented in FIG. 5.

Example 8

ATR-FTIR Analysis of SELP Drug-Loaded Gels

FTIR Analysis was performed on a Nicolet 6700 spectrometer (Thermo Scientific) equipped with a mercury cadmium telluride (MCT-A) detector and a Smart_iTX attenuated total reflectance (ATR) accessory fitted with a single reflection diamond element. Individual spectra were acquired with 512 co-added scans ratioed to a background of 512 scans. Scans were Fourier transformed with two levels of zero filling and Happ-Genzel apodization to obtain infrared spectra with the range of 4000 to 850 $cm^{-1}$ at a spectral resolution of 4 $cm^{-1}$. Hydrated 9% SELP-815K gels fully loaded with drug incorporated as a DMSO solution or milled powder were tested. Absorbance spectra of powdered drug, PBS, and DMSO were acquired as references. Data were analyzed with OMNIC software using Proteus Protein Analysis algorithms (Thermo Scientific). Sample spectra were further processed with subtraction of reference spectra of the buffer and/or DMSO, if applicable, and baseline correction.

The amide I region (1700 $cm^{-1}$ to 1600 $cm^{-1}$) was deconvolved using comparative Gaussian and Voigt peak fitting models. In addition, second derivative spectra were obtained to identify absorption peak locations of the secondary structure peaks in the silk-elastinlike matrix. The percentages of secondary structures (alpha helix, beta sheet, etc.) in each sample spectrum were calculated from peak integration.

Drug-loaded 9% SELP-815K gels were analyzed using ATR-FTIR methods to detect possible changes in protein secondary structure in the presence and absence of the two individual drugs and when both drugs are incorporated together in the SELP matrix. Further infrared (IR) analyses were also conducted on the two groups of drug-loaded SELP (i.e., wherein the drugs were dissolved in DMSO before incorporation or whether incorporation involved mechanically mixing powder into the SELP solutions). The amide I band (1705-1595 $cm^{-1}$) in the IR absorption spectrum arises from the carbonyl C=O stretching vibrations in the protein backbone. This vibrational mode is indicative of and most sensitive to the hydrogen bonding that forms secondary structures within the protein backbone. In particular, the region between 1640 and 1614 $cm^{-1}$ is assigned to beta sheets, from 1660 to 1640 $cm^{-1}$ to random/unordered coils and alpha helices, and the region between 1690 and 1660 $cm^{-1}$ to beta turn secondary structures. Smaller peaks between 1705 and 1690 $cm^{-1}$ can arise from additional beta sheet structures. IR absorption in the amide II region arises from the N—H bending and C—N stretching vibrational modes.

Absorbance spectra of the amide I region are shown in FIG. 6. FIG. 6A consists of spectra for gels with drug dissolved in DMSO and incorporated into SELP. Panel B shows the spectra for gels incorporating powder drug. These spectra were examined with digital algorithms such as Fourier self-deconvolution (FSD), second derivative spectra and peak fitting with Gaussian, Gaussian-Lorentzian, and Voigt band shapes to assess, qualitatively and quantitatively, different secondary structures of the silk-elastinlike matrix in the absence or presence of drug molecules or crystals. The second derivative of each spectrum was calculated to determine the locations of secondary structure peaks, which were confirmed with assignments in the literature.

Figure 6A:
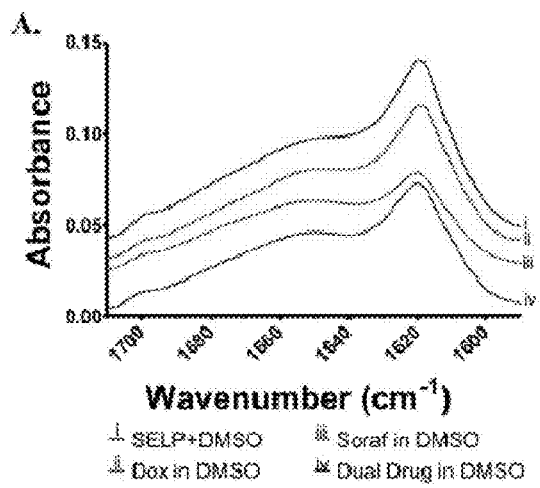
FIGS. 6A-6E show ATR-FTIR absorbance spectra of 9% SELP-815K gels loaded with base forms of doxorubicin, sorafenib, or both drugs (dual).
Figure 6B:
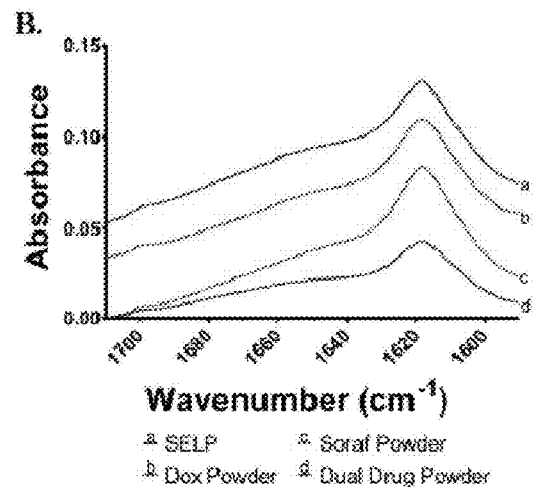
Figure 6C:
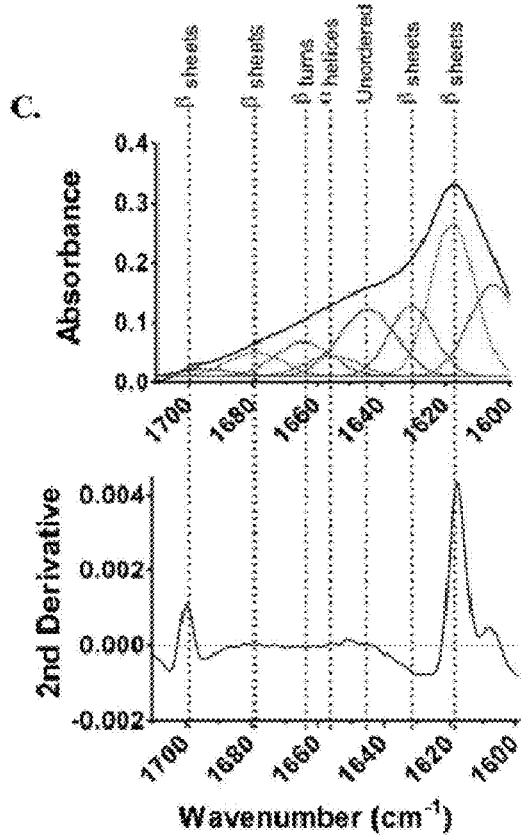
Figure 6D:
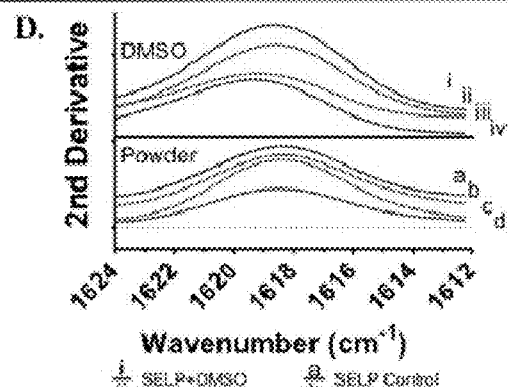

FIG. 6C displays the deconvolved spectra of a control 9% SELP-815K sample. Peaks associated with the following secondary structure elements were identified: beta sheets (1618, 1630, 1679, and 1694 $cm^{-1}$), random/unordered coils (1644 $cm^{-1}$), alpha helices (1656 $cm^{-1}$), and beta turns (1664 $cm^{-1}$). The beta sheets are the dominant structural component of the SELP matrix. Changes in relative amount of beta sheet absorption would be indicative of ultrastructural changes in the gel network due to molecular interaction of drug species. As identified in the second derivative traces (FIG. 6D), peak shifts in the primary beta sheet absorbance peak at 1618 $cm^{-1}$ revealed changes in secondary structure relative to the native SELP gel spectrum. An upshift of the peak, indicative of increased energy required for vibrational motion, was seen for gels loaded with sorafenib dissolved in DMSO (single drug and dual drug). No other gels showed obvious peak shifts. This observation suggests that dissolved sorafenib is interacting with the SELP network through hydrogen bonding.

Figure 6E:
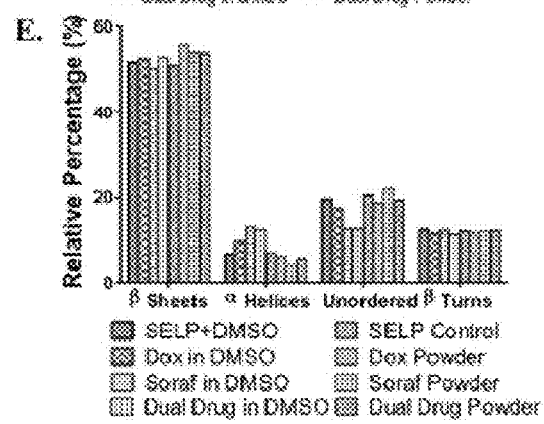

The relative percentage of secondary structures for each test group is shown in FIG. 6E. In the gels incorporating powder drug, an increase in total percentage of beta sheets was observed. The doxorubicin powder incorporated gel showed the greatest increase when compared to the SELP control. Additionally, this gel showed a decrease in the number of unordered coils. Percentage of alpha helices increased compared to the control with increasing content as follows: doxorubicin in DMSO<dual drug in DMSO<sorafenib in DMSO. Sorafenib in DMSO had a 1.97-fold increase over the control. In this same group, the relative number of unordered coils decreased compared to the control. Sorafenib in DMSO had the greatest decrease, at 1.5-fold. The dual drug in DMSO-loaded samples showed trends more similar to sorafenib alone versus doxorubicin alone, indicating that the presence of sorafenib had a greater effect on the protein secondary structures. Interestingly, the method of sorafenib incorporation resulted in opposite trends in the two groups. When dissolved in DMSO, the relative percentage of alpha helices increased and unordered coils decreased, while with the powder there was a decrease in the alpha helix content and increase in unordered coils. The presence of doxorubicin in the SELP gels increased the beta sheet content for both methods of incorporation. No change in beta turns was determined for any gels when compared to their respective controls.

Example 9

Rheological Characterization and Drug Release from 12% SELP-815K Gels

The information gained from the drug-loaded 9% SELP-815K gels indicated that drug release of doxorubicin, sorafenib, or both was sufficient to provide therapeutically effective local concentrations of the drugs for 14 days. While incorporation into SELP solution of either or both drugs dissolved in DMSO yielded a more uniform dispersion than incorporation of the powder drugs as indicated by SEM, it resulted in at least a 2-fold increase in viscosity of the SELP solution and exceeds the maximum viscosity for injectability through a microcatheter, whereas incorporation of either or both drugs as powders caused no change in viscosity. However, the 9% concentration of SELP used in these evaluations yielded gel stiffness that was below the targeted specification of $1\times10^5$ Pa. Hence, we repeated the drug incorporation and release studies with 12% SELP-815K, a liquid embolic formulation that was previously shown to occlude branches of the hepatic artery in vivo.

Figures 7A, 7B:
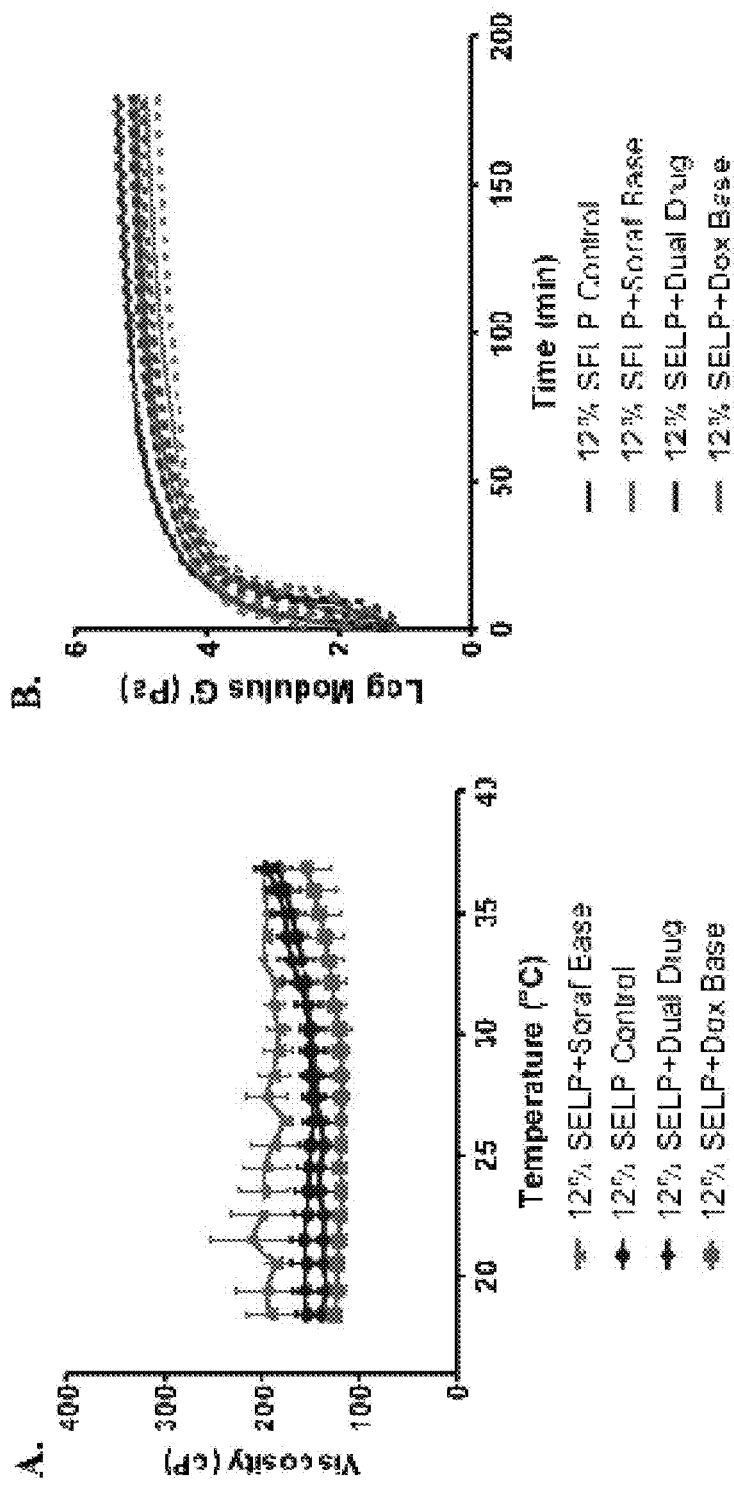
FIGS. 7A-7B show rheological characterization of 12% SELP-815K loaded with base forms of doxorubicin and/or sorafenib as powders at 25 mg/mL. In the dual drug gels, each drug was loaded at 25 mg/mL with final total drug loading of 50 mg/mL.

Based on the results obtained with the 9% SELP-815K gels, the incorporation of the base forms of each drug as powder in the 12% SELP-815K formulation was tested. In these studies, the dual drug group had a loading of 25 mg/mL of each drug, yielding a total drug loading of 50 mg/mL (twice the amount used in the 9% gels). Rheological characterization was conducted as before. FIG. 7A shows the viscosity curves for the 12% SELP-815K samples. When compared to the control with no drug, no significant differences in viscosity were observed at any temperature. Therefore, loading of the base forms of each drug up to 25 mg/mL or both drugs up to a combined 50 mg/mL total drug content had no effect on the injectability of the formulation. Measurements of the storage modulus, G' (FIG. 7B) shows that, while drug incorporation reduced the storage modulus compared to the control, the differences were not statistically significant and that all gels resulted in an average 180-minute modulus of $\geq 1\times10^5$ Pa.

Example 10

Single Agent In Vitro Toxicity

Growth inhibition by the base drugs used in this study was evaluated on three different hepatoma cell lines—two human HCC lines and one rat cell line—using a 2-(2-methoxy-4-nitrophenyl)-3-(4-nitrophenyl)-5-(2,4-disulfophenyl)-2H-tetrazolium monosodium salt (WST-8) cell viability assay (Dojindo Molecular Technologies, Inc., Rockville, Md.). Human cell lines Hep3B and HepG2 were obtained from ATCC (Manassas, Va.) and cultured in EMEM cell culture medium (ATCC) supplemented with 10% fetal bovine serum (FBS). The rat hepatoma line McA-RH7777 was generously donated by the Larson Lab (Northwestern University, IL). This line was cultured in DMEM cell culture medium (ATCC) supplemented with 10% FBS. All lines were grown at 37° C. in a humidified atmosphere of 5% $CO_2$.

To prevent precipitation of the drugs, media containing 0.5% DMSO was used throughout all the studies. Doubling times of the cell lines were similar; therefore, cells were plated at the same density of 7,000 cells per well in 96-well plates for 24 hours. Media was removed, cells were washed with PBS, and treatment was applied. Drug concentrations were varied to include data points ranging from non-toxic to highly toxic. Following 72 hours of incubation, the media was removed and cell viability was quantified using the WST-8 assay with a SpectraMax M2 spectrophotometer (Molecular Devices, Sunnyvale, Calif.).

Each experiment was performed with N=6, assessing viability at 10 different drug concentrations. Relative cell viability was calculated by normalizing against the UV absorbance of untreated cells. GraphPad Prism was used to plot relative cell viability as a function of log drug concentration with a non-linear least-squares regression analysis and calculation of $IC_{50}$ values. Results are presented in Table 5.

TABLE 5

Results from Single Drug Cytotoxicity Experiments: $IC_{50}$ Values of Each Drug per HCC Cell Line (μM)

|  | Sorafenib | Doxorubicin |
| --- | --- | --- |
| Hep3B | 3.47 ± 0.2 | 0.29 ± 0.04 |
| HepG2 | 1.72 ± 0.70 | 0.62 ± 0.41 |
| McA-RH7777 | 6.88 ± 0.83 | 0.48 ± 0.32 |

Example 11

Statistical Analysis

All rheological and drug release experiments were conducted in triplicate and data is presented as the mean±standard deviation (SD) unless otherwise specified. Significance between multiple groups was determined using a one-way analysis of variance (ANOVA) with a Tukey's posttest, and a two-tailed Student's t-test for comparing pairs of data. Statistical significance was reported as $p<0.05$, highly significant when $p<0.01$, and very highly significant when $p<0.001$.

Throughout this publication, various publications are referenced. The disclosures of these publications in their entireties are hereby incorporated by reference into this application in order to more fully describe the methods, compositions, and compounds herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed:

1. A method for treating cancer in a subject comprising administering a composition comprising a sheared silk-elastinlike protein into the tumor vasculature of the subject, wherein the composition creates an embolus in the tumor vasculature.

2. A method for reducing or inhibiting the growth of a tumor in a subject comprising administering a composition comprising a sheared silk-elastinlike protein into the tumor vasculature of the subject, wherein the composition creates an embolus in the tumor vasculature.

3. The method of claim 1, wherein the composition is a liquid prior to administration to a subject but converts to a hydrogel upon administration to the subject.

4. The method of claim 2, wherein the composition is a liquid prior to administration to a subject but converts to a hydrogel upon administration to the subject.

5. The method of claim 1, wherein the composition further comprises one or more anti-cancer agents forming a chemoembolic agent with the sheared silk-elastinlike protein.

6. The method of claim 5, wherein the sheared silk-elastinlike protein delivers the one or more anti-cancer agent to the tumor.

7. The method of claim 6, wherein the sheared silk-elastinlike protein releases the one or more anti-cancer agents at a controlled rate.

8. The method of claim 1, wherein the sheared silk-elastinlike protein has at least seven elastin like units.

9. The method of claim 1, wherein the sheared silk-elastinlike protein is SELP-47K, SELP-815K, SELP-27K, SELP-415K, SELP-pSE8Y, SELP-pS2E8Y, SELP-pS4E8Y, or any combination thereof.

10. The method of claim 1, wherein the sheared silk-elastinlike protein comprises one or more matrix metalloproteinase (MMP) cleavage sites.

11. The method of claim 5, wherein the anti-cancer agent is paclitaxel, docetaxel, gemcitabine, a platinate, doxorubicin, geldanamycin, epirubicin, 9-aminocamptothecin, sorafenib, or any combination thereof, and wherein the anti-cancer agent is a neutral compound or the pharmaceutically-acceptable salt thereof.

12. The method of claim 11, wherein the anti-cancer agent is the pharmaceutically-acceptable salt of doxorubicin and the pharmaceutically-acceptable salt of sorafenib.

13. The method of claim 5, wherein the anti-cancer agent is doxorubicin hydrochloride and sorafenib tosylate.

14. The method of claim 5, wherein the anti-cancer agent is admixed with a liquid composition of the sheared silk-elastinlike protein, wherein the sheared silk-elastinlike protein is from 2% to 20% w/w of the liquid composition.

15. The method of claim 14, wherein the sheared silk-elastinlike protein is from 5% to 15% w/w of the liquid composition.

16. The method of claim 14, wherein the anti-cancer agent is admixed with the liquid composition as a solution comprising a solvent, wherein the solvent comprises water, dimethylsulfoxide, or a combination thereof.

17. The method of claim 5, wherein the anti-cancer agent is from 1 mg/mL to 100 mg/mL of the chemoembolic agent.

18. The method of claim 5, wherein the sheared silk-elastinlike protein is SELP-815K, the sheared SELP is from 5% to 15% w/w of the chemoembolic agent, and the anticancer agent is the pharmaceutically-acceptable salt of doxorubicin and sorafenib.

19. The method of claim 18, wherein the anti-cancer drug is the pharmaceutically-acceptable salt of doxorubicin and the pharmaceutically-acceptable salt of sorafenib.

20. The method of claim 5, wherein the composition further comprises a contrast agent.

21. The method of claim 5, wherein the chemoembolic agent has a viscosity of less than equal to 700 cP at 18 to 23° C.

22. The method of claim 2, wherein the composition further comprises one or more anti-cancer agents forming a chemoembolic agent with the sheared silk-elastinlike protein.

* * * * *